United States Patent
Sakamoto et al.

(10) Patent No.: US 9,207,360 B2
(45) Date of Patent: Dec. 8, 2015

(54) POLYMERIZABLE COMPOUND, POLYMERIZABLE COMPOSITION, POLYMER, AND OPTICALLY ANISOTROPIC BODY

(75) Inventors: Kei Sakamoto, Tokyo (JP); Kumi Okuyama, Tokyo (JP)

(73) Assignee: ZENO CORPORATION, Tokyo (JP)

( * ) Notice: Subject to any disclaimer, the term of this patent is extended or adjusted under 35 U.S.C. 154(b) by 205 days.

(21) Appl. No.: 14/114,073

(22) PCT Filed: Apr. 27, 2012

(86) PCT No.: PCT/JP2012/061321
§ 371 (c)(1),
(2), (4) Date: Dec. 19, 2013

(87) PCT Pub. No.: WO2012/147904
PCT Pub. Date: Nov. 1, 2012

(65) Prior Publication Data
US 2014/0142266 A1 May 22, 2014

(30) Foreign Application Priority Data

Apr. 27, 2011 (JP) ................................ 2011-099525
Oct. 28, 2011 (JP) ................................ 2011-237993

(51) Int. Cl.
C07C 251/82 (2006.01)
C07C 251/86 (2006.01)
C07D 277/82 (2006.01)
G02B 1/08 (2006.01)
G02B 5/30 (2006.01)
C07D 215/38 (2006.01)
C07D 237/34 (2006.01)
C07D 263/58 (2006.01)
C08F 220/34 (2006.01)
C08F 222/10 (2006.01)

(52) U.S. Cl.
CPC ................ *G02B 1/08* (2013.01); *C07C 251/86* (2013.01); *C07D 215/38* (2013.01); *C07D 237/34* (2013.01); *C07D 263/58* (2013.01); *C07D 277/82* (2013.01); *C08F 220/34* (2013.01); *C08F 222/1006* (2013.01); *G02B 5/3083* (2013.01)

(58) Field of Classification Search
CPC .. C07C 252/82; C07C 252/86; C07D 277/82; G02B 1/08; G02B 5/30
See application file for complete search history.

(56) References Cited

U.S. PATENT DOCUMENTS

| 5,567,349 A | 10/1996 | Kelly et al. |
|---|---|---|
| 6,139,771 A | 10/2000 | Walba et al. |
| 6,203,724 B1 | 3/2001 | Reiffenrath et al. |
| 6,565,974 B1 | 5/2003 | Uchiyama et al. |
| 6,858,161 B2 * | 2/2005 | Abe et al. ............... 252/500 |
| 9,029,490 B2 * | 5/2015 | Sakamoto et al. ......... 526/312 |
| 2002/0159005 A1 | 10/2002 | Arakawa et al. |
| 2003/0102458 A1 | 6/2003 | Nishikawa et al. |
| 2007/0176145 A1 | 8/2007 | Nishikawa et al. |
| 2007/0298191 A1 | 12/2007 | Yamahara et al. |
| 2009/0072194 A1 | 3/2009 | Yamahara et al. |

(Continued)

FOREIGN PATENT DOCUMENTS

| EP | 2119698 A1 | 11/2009 |
|---|---|---|
| EP | 2143710 A1 | 1/2010 |

(Continued)

OTHER PUBLICATIONS

International Search Report for PCT/JP2012/061321 mailed on Jun. 5, 2012.
Extended European Search Report, dated Sep. 4, 2014, for European Application No. 12775984.3.

*Primary Examiner* — Shean C Wu
(74) *Attorney, Agent, or Firm* — Birch, Stewart, Kolasch & Birch, LLP

(57) ABSTRACT

The present invention relates to a polymerizable compound represented by a formula (I). The present invention provides a polymerizable compound, a polymerizable composition, a polymer, and an optically anisotropic article that are capable of obtaining an optical film having a low melting point, having excellent solubility, capable of being manufactured at low cost, and capable of uniform polarized light conversion across a broad wavelength region. [In formula: $Y^1$ to $Y^6$ are independently a chemical single bond, —O—, —O—C(=O)—, —C(=O)—O— etc.; $G^1$ and $G^2$ are independently a divalent C1-C20 aliphatic group etc.; $Z^1$ and $Z^2$ are independently C2-C10 alkenyl group that is substituted with a halogen atom etc.; $A^x$ is a C2-C30 organic group that includes at least one aromatic ring selected from a group consisting of an aromatic hydrocarbon ring and an aromatic hetero ring; $A^y$ is a hydrogen atom, a C1-C20 alkyl group, a C2-C20 alkenyl group, a C3-C12 cycloalkyl group etc.; $A^1$ is a trivalent aromatic group etc.; $A^2$ and $A^3$ are independently a divalent C6-C30 aromatic group etc.; and $Q^1$ is a hydrogen atom, or a C1-C6 alkyl group etc.]

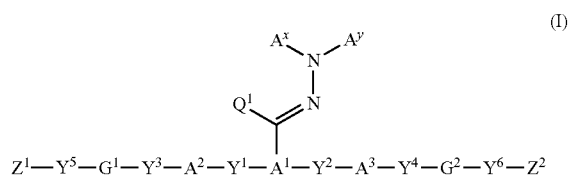

(I)

20 Claims, 2 Drawing Sheets

(56) References Cited

U.S. PATENT DOCUMENTS

| | | |
|---|---|---|
| 2009/0189120 A1 | 7/2009 | Takeuchi |
| 2010/0201920 A1 | 8/2010 | Adlem et al. |
| 2010/0258764 A1 | 10/2010 | Sakamoto et al. |
| 2010/0301271 A1 | 12/2010 | Adlem et al. |
| 2011/0233464 A1 | 9/2011 | Katoh et al. |
| 2012/0202084 A1 | 8/2012 | Tamura |
| 2015/0175564 A1* | 6/2015 | Sakamoto et al. ............ 526/257 |
| 2015/0183902 A1* | 7/2015 | Sakamoto et al. ............ 526/257 |

FOREIGN PATENT DOCUMENTS

| | | |
|---|---|---|
| JP | 10-68816 A | 3/1998 |
| JP | 10-90521 A | 4/1998 |
| JP | 11-52131 A | 2/1999 |
| JP | 2001-4837 A | 1/2001 |
| JP | 2001-234154 A | 8/2001 |
| JP | 2002-267838 A | 9/2002 |
| JP | 2005-208414 A | 8/2005 |
| JP | 2005-208415 A | 8/2005 |
| JP | 2005-208416 A | 8/2005 |
| JP | 2009-149754 A | 7/2009 |
| JP | 2010-31223 A | 2/2010 |
| JP | 2010-70505 A | 4/2010 |
| JP | 2010-138283 A | 6/2010 |
| JP | 2010-159324 A | 7/2010 |
| JP | 2011-6360 A | 1/2011 |
| JP | 2011-6361 A | 1/2011 |
| JP | 2011-42606 A | 3/2011 |
| WO | WO 2008/105538 A1 | 9/2008 |

* cited by examiner

US 9,207,360 B2

POLYMERIZABLE COMPOUND, POLYMERIZABLE COMPOSITION, POLYMER, AND OPTICALLY ANISOTROPIC BODY

TECHNICAL FIELD

The invention relates to a polymerizable compound, a polymerizable composition, and a polymer that may produce an optical film that achieves uniform conversion of polarized light over a wide wavelength band, and also relates to an optically anisotropic article.

A flat panel display (FPD) that utilizes an optical film (e.g., polarizer and retardation film) can achieve high-resolution display, and has been widely used as a display device (e.g., TV) that achieves high performance.

Examples of the retardation film include a quarter-wave plate that converts linearly polarized light into circularly polarized light, and a half-wave plate that converts the plane of vibration of linearly polarized light by 90°. Such a retardation film can achieve accurate conversion of specific monochromatic light so that ¼λ or ½λ retardation occurs.

However, a known retardation film has a problem in that polarized light that passes through the retardation film is converted into colored polarized light. Specifically, since a material that forms the retardation film has wavelength dispersion with regard to retardation, and a polarization state distribution corresponding to each wavelength occurs for white light that includes different light beams in the visible region, it is impossible to achieve accurate ¼λ or ½λ retardation over the entire wavelength band.

In order to solve the above problems, various wideband retardation films that can achieve uniform retardation for light over a wide wavelength band (i.e., retardation films having reverse wavelength dispersion) have been studied (see Patent Documents 1 to 6, for example).

It has been desired to reduce the thickness of the flat panel display as much as possible along with an improvement in performance and widespread use of mobile information terminals (e.g., mobile personal computer and mobile phone). Therefore, a reduction in thickness of the retardation film has also been desired.

It has been considered that it is most effective to produce a retardation film by applying a polymerizable composition that includes a low-molecular-weight polymerizable compound to a film substrate in order to reduce the thickness of the retardation film. Various low-molecular-weight polymerizable compounds having excellent wavelength dispersion, and various polymerizable compositions using such polymerizable compounds have been developed (see Patent Documents 7 to 24, for example).

However, the low-molecular-weight polymerizable compounds or the polymerizable compositions disclosed in Patent Documents 7 to 24 have a number of problems in that reverse wavelength dispersion may be insufficient, or it may be difficult to apply the low-molecular-weight polymerizable compounds or the polymerizable compositions to a film due to a high melting point that is not suitable for an industrial process, or the temperature range in which liquid crystallinity is obtained may be very narrow, or solubility in a solvent generally used for an industrial process may be low. Moreover, since the above low-molecular-weight polymerizable compounds and the like are synthesized by a plurality of steps using a synthesis method that utilizes an expensive reagent, the production cost increases.

RELATED-ART DOCUMENT

Patent Document

Patent Document 1: JP-A-10-68816
Patent Document 2: JP-A-10-90521
Patent Document 3: JP-A-11-52131
Patent Document 4: JP-A-2000-284126 (US20020159005A1)
Patent Document 5: JP-A-2001-4837
Patent Document 6: WO2000/026705
Patent Document 7: JP-A-2002-267838
Patent Document 8: JP-A-2003-160540 (US20030102458A1)
Patent Document 9: JP-A-2005-208414
Patent Document 10: JP-A-2005-208415
Patent Document 11: JP-A-2005-208416
Patent Document 12: JP-A-2005-289980 (US20070176145A1)
Patent Document 13: JP-A-2006-330710 (US20090072194A1)
Patent Document 14: JP-A-2009-179563 (US20090189120A1)
Patent Document 15: JP-A-2010-31223
Patent Document 16: JP-A-2011-6360
Patent Document 17: JP-A-2011-6361
Patent Document 18: JP-A-2011-42606
Patent Document 19: JP-T-2010-537954 (US20100201920A1)
Patent Document 20: JP-T-2010-537955 (US20100301271A1)
Patent Document 21: WO2006/052001 (US20070298191A1)
Patent Document 22: U.S. Pat. No. 6,139,771
Patent Document 23: U.S. Pat. No. 6,203,724
Patent Document 24: U.S. Pat. No. 5,567,349

SUMMARY OF THE INVENTION

Technical Problem

The invention was conceived in view of the above situation. An object of the invention is to provide a polymerizable compound, a polymerizable composition, and a polymer that have a practical low melting point, exhibit excellent solubility in a general-purpose solvent, can be produced at low cost, and can produce an optical film that achieves uniform conversion of polarized light over a wide wavelength band, and an optically anisotropic article.

Solution to Problem

The inventors of the invention conducted extensive studies in order to achieve the above object. As a result, the inventors found that an optical film that achieves uniform conversion of polarized light over a wide wavelength band, and shows satisfactory performance can be produced at low cost by utilizing an optically anisotropic article produced using a polymer obtained by polymerizing a polymerizable compound represented by the following formula (I), or a polymerizable composition that includes the polymerizable compound and an initiator. This finding has led to the completion of the invention.

Several aspects of the invention provide the following polymerizable compound (see (1) to (9)), polymerizable composition (see (10) and (11)), polymer (see (12) and (13)), and optically anisotropic article (see (14)).

(1) A polymerizable compound represented by the following formula (I),

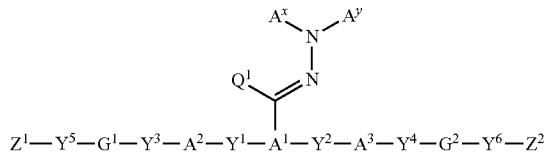

(I)

wherein $Y^1$ to $Y^6$ are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, $R^1$ is a hydrogen atom or an alkyl group having 1 to 6 carbon atoms, $G^1$ and $G^2$ are independently a substituted or unsubstituted divalent aliphatic group having 1 to 20 carbon atoms that optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)—, provided that a case where the aliphatic group includes two or more adjacent —O— or —S— is excluded, $R^2$ is a hydrogen atom or an alkyl group having 1 to 6 carbon atoms, $Z^1$ and $Z^2$ are independently an alkenyl group having 2 to 10 carbon atoms that is substituted with a halogen atom, or unsubstituted, $A^x$ is an organic group having 2 to 30 carbon atoms that includes at least one aromatic ring selected from a group consisting of an aromatic hydrocarbon ring and an aromatic hetero ring, $A^y$ is a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, —C(=O)—R$^3$, —SO$_2$—R$^6$, or an organic group having 2 to 30 carbon atoms that includes at least one aromatic ring selected from a group consisting of an aromatic hydrocarbon ring and an aromatic hetero ring, provided that the aromatic ring included in $A^x$ and $A^y$ is substituted or unsubstituted, and $A^x$ and $A^y$ optionally bond to each other to form a ring, $R^3$ is a substituted or unsubstituted alkyl group having 1 to 20 carbon atoms, a substituted or unsubstituted alkenyl group having 2 to 20 carbon atoms, or a substituted or unsubstituted cycloalkyl group having 3 to 12 carbon atoms, $R^6$ is an alkyl group having 1 to 20 carbon atoms, an alkenyl group having 2 to 20 carbon atoms, a phenyl group, or a 4-methylphenyl group, $A^1$ is a substituted or unsubstituted trivalent aromatic group, $A^2$ and $A^3$ are independently a substituted or unsubstituted divalent aromatic group having 6 to 30 carbon atoms, and $Q^1$ is a hydrogen atom, or a substituted or unsubstituted alkyl group having 1 to 6 carbon atoms.

(2) The polymerizable compound according to (1), wherein the total number of π electrons included in $A^x$ and $A^y$ is 4 to 24.

(3) The polymerizable compound according to (1) or (2), wherein $A^x$ is a substituted or unsubstituted group among groups represented by the following structural formulas,

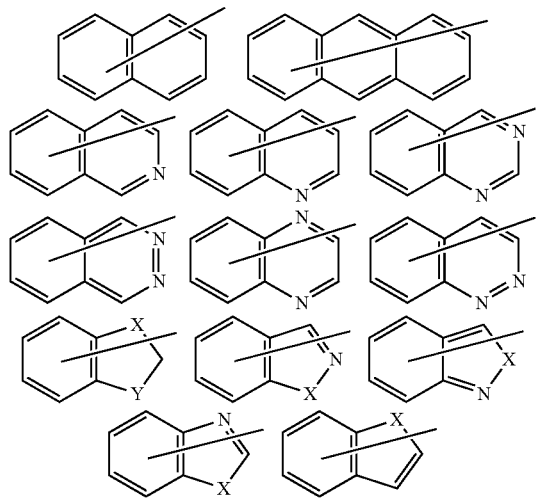

wherein X is NR$^5$, an oxygen atom, a sulfur atom, —SO—, or —SO$_2$—, provided that a case where oxygen atoms, sulfur atoms, —SO—, or —SO$_2$— are situated at adjacent positions is excluded, and $R^5$ is a hydrogen atom or an alkyl group having 1 to 6 carbon atoms.

(4) The polymerizable compound according to any one of (1) to (3), wherein $A^y$ is a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, a group represented by —C(=O)—R$^3$ (wherein R$^3$ is a substituted or unsubstituted alkyl group having 1 to 12 carbon atoms, a substituted or unsubstituted alkenyl group having 2 to 12 carbon atoms, or a substituted or unsubstituted cycloalkyl group having 3 to 12 carbon atoms), or a group represented by —SO$_2$—R$^6$ (wherein R$^6$ is an alkyl group having 1 to 12 carbon atoms, an alkenyl group having 2 to 12 carbon atoms, a phenyl group, or a 4-methylphenyl group).

(5) The polymerizable compound according to any one of (1) to (4), wherein $A^1$ is a substituted or unsubstituted trivalent benzene ring group, or a substituted or unsubstituted trivalent naphthalene ring group, and $A^2$ and $A^3$ are independently a substituted or unsubstituted phenylene group, or a substituted or unsubstituted naphthylene group.

(6) The polymerizable compound according to any one of (1) to (5), wherein $Y^1$ to $Y^6$ are independently a chemical single bond, —O—, —O—C(=O)—, —C(=O)—O—, or —O—C(=O)—O—.

(7) The polymerizable compound according to any one of (1) to (6), wherein $Z^1$ and $Z^2$ are independently CH$_2$=CH—, CH$_2$=C(CH$_3$)—, or CH$_2$=C(Cl)—.

(8) The polymerizable compound according to any one of (1) to (7), wherein $G^1$ and $G^2$ are independently a substituted or unsubstituted divalent aliphatic group having 1 to 12 carbon atoms that optionally includes —O—, —O—C(=O)—, —C(=O)—O—, or —C(=O)—, provided that a case where the aliphatic group includes two or more adjacent —O— is excluded.

(9) The polymerizable compound according to any one of (1) to (8), wherein $G^1$ and $G^2$ are independently a divalent alkylene group having 1 to 12 carbon atoms.

(10) A polymerizable composition including at least one type of the polymerizable compound according to any one of (1) to (9).

(11) A polymerizable composition including the polymerizable compound according to any one of (1) to (9), and an initiator.
(12) A polymer obtained by polymerizing the polymerizable compound according to any one of (1) to (9), or the polymerizable composition according to (10) or (11).
(13) The polymer according to (12), the polymer being a liquid crystalline polymer.
(14) An optically anisotropic article including the polymer according to (13).

Advantageous Effects of the Invention

The polymerizable compound, the polymerizable composition, and the polymer according to the aspects of the invention make it possible to inexpensively obtain an optically anisotropic article that achieves uniform conversion of polarized light over a wide wavelength band, and shows satisfactory performance.

Since the optically anisotropic article according to the aspect of the invention is produced using the polymer according to the aspect of the invention, the optically anisotropic article can be produced at low cost, achieves uniform conversion of polarized light over a wide wavelength band, and shows satisfactory performance.

For example, an antireflective film may be produced by combining the film-shaped optically anisotropic article according to the aspect of the invention with a polarizer. The antireflective film may suitably be used to prevent reflection from a touch panel, an organic electroluminescent device, and the like.

DESCRIPTION OF EMBODIMENTS

Figure 1:
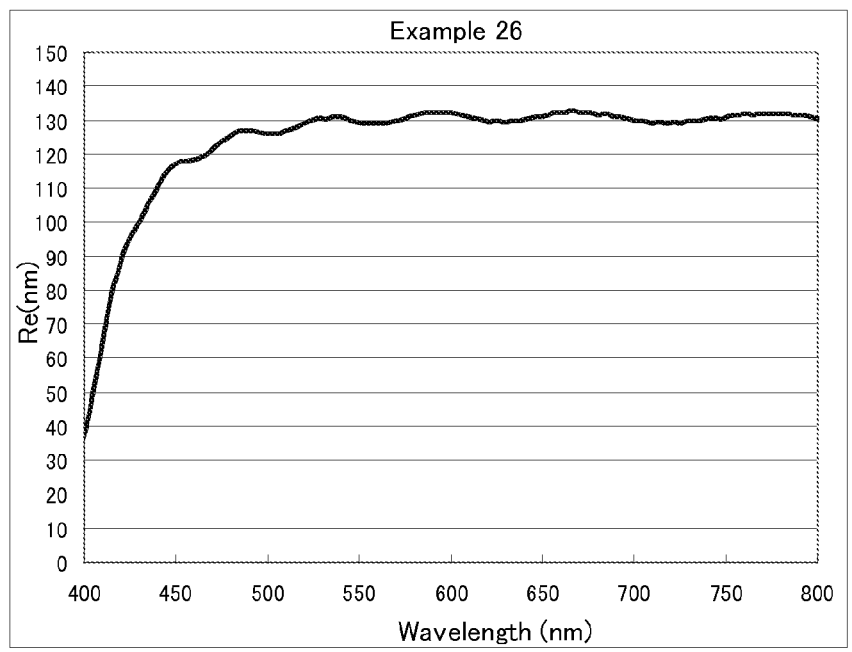
FIG. 1 is a view showing the wavelength dispersion of the liquid crystalline polymer film obtained by polymerizing the polymerizable composition 6 of Example 26.

A polymerizable compound, a polymerizable composition, a polymer, and an optically anisotropic article according to the embodiments of the invention are described in detail below.
1) Polymerizable Compound
A polymerizable compound according to one embodiment of the invention is a compound represented by the formula (I).

In the formula (I), $Y^1$ to $Y^6$ are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—.

$R^1$ is a hydrogen atom or an alkyl group having 1 to 6 carbon atoms.

Examples of the alkyl group having 1 to 6 carbon atoms represented by $R^1$ include a methyl group, an ethyl group, an n-propyl group, an isopropyl group, an n-butyl group, a sec-butyl group, a t-butyl group, an n-pentyl group, an n-hexyl group, and the like.

$R^1$ is preferably a hydrogen atom or an alkyl group having 1 to 4 carbon atoms.

It is preferable that $Y^1$ to $Y^6$ are independently a chemical single bond, —O—, —O—C(=O)—, —C(=O)—O—, or —O—C(=O)—O—.

$G^1$ and $G^2$ are independently a substituted or unsubstituted divalent aliphatic group having 1 to 20 carbon atoms.

Examples of the divalent aliphatic group having 1 to 20 carbon atoms include divalent aliphatic groups having a chain-like structure; divalent aliphatic groups having an alicyclic structure such as a saturated cyclic hydrocarbon (cycloalkane) structure or an unsaturated cyclic hydrocarbon (cycloolefin) structure; and the like.

Examples of a substituent that may substitute the divalent aliphatic group represented by $G^1$ and $G^2$ include halogen atoms such as a fluorine atom, a chlorine atom, a bromine atom, and an iodine atom; alkoxy groups having 1 to 6 carbon atoms, such as a methoxy group, an ethoxy group, an n-propoxy group, an isopropoxy group, an n-butoxy group, a sec-butoxy group, a t-butoxy group, an n-pentyloxy group, and an n-hexyloxy group; and the like. Among these, a fluorine atom, a methoxy group, and an ethoxy group are preferable.

The aliphatic group optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)— (provided that a case where the aliphatic group includes two or more adjacent —O— or —S— is excluded).

$R^2$ is a hydrogen atom or an alkyl group having 1 to 6 carbon atoms similar to that represented by $R^1$, and is preferably a hydrogen atom or a methyl group.

—O—, —O—C(=O)—, —C(=O)—O—, and —C(=O)— are preferable as the group that is optionally included in the aliphatic group.

Specific examples of the aliphatic group that includes the above group include —CH$_2$—CH$_2$—O—CH$_2$—CH$_2$—, —CH$_2$—CH$_2$—S—CH$_2$—CH$_2$—, —CH$_2$—CH$_2$—O—C(=O)—CH$_2$—CH$_2$—, —CH$_2$—CH$_2$—C(=O)—O—CH$_2$—CH$_2$—, —CH$_2$—CH$_2$—C(=O)—O—CH$_2$—, —CH$_2$—O—C(=O)—O—CH$_2$—CH$_2$—, —CH$_2$—CH$_2$—NR$^2$—C(=O)—CH$_2$—CH$_2$—, —CH$_2$—CH$_2$—C(=O)—NR$^2$—CH$_2$—, —CH$_2$—NR$^2$—CH$_2$—CH$_2$—, —CH$_2$—C(=O)—CH$_2$—, and the like.

It is preferable that $G^1$ and $G^2$ are independently a divalent aliphatic group having a chain-like structure (e.g., an alkylene group having 1 to 20 carbon atoms or an alkenylene group having 2 to 20 carbon atoms), more preferably an alkylene group having 1 to 12 carbon atoms (e.g., methylene group, ethylene group, trimethylene group, propylene group, tetramethylene group, pentamethylene group, hexamethylene group, or octamethylene group), and particularly preferably a tetramethylene group (—(CH$_2$)$_4$—) or a hexamethylene group (—(CH$_2$)$_6$—), in order to ensure that the intended effects of the invention can be more advantageously achieved.

$Z^1$ and $Z^2$ are independently an alkenyl group having 2 to 10 carbon atoms that is substituted with a halogen atom, or unsubstituted.

The number of carbon atoms of the alkenyl group is preferably 2 to 6. Examples of the halogen atom that may substitute the alkenyl group represented by $Z^1$ and $Z^2$ include a fluorine atom, a chlorine atom, a bromine atom, and the like. Among these, a chlorine atom is preferable.

Specific examples of the alkenyl group having 2 to 10 carbon atoms represented by $Z^1$ and $Z^2$ include CH$_2$=CH—, CH$_2$=C(CH$_3$)—, CH$_2$=CH—CH$_2$—, CH$_3$—CH=CH—, CH$_2$=CH—CH$_2$—CH$_2$—, CH$_2$=C(CH$_3$)—CH$_2$—CH$_2$—, (CH$_3$)$_2$C=CH—CH$_2$—, (CH$_3$)$_2$ C=CH—CH$_2$—CH$_2$—, CH$_2$=C(Cl)—, CH$_2$=C(CH$_3$)—CH$_2$—, CH$_3$—CH=CH—CH$_2$—, and the like.

It is preferable that $Z^1$ and $Z^2$ be independently CH$_2$=CH—, CH$_2$=C(CH$_3$)—, CH$_2$=C(Cl)—, CH$_2$=CH—CH$_2$—, CH$_2$=C(CH$_3$)—CH$_2$—, or CH$_2$=C(CH$_3$)—CH$_2$—CH$_2$—, more preferably CH$_2$=CH—, CH$_2$=C(CH$_3$)—, or CH$_2$=C(Cl)—, and particularly preferably CH$_2$=CH—, in order to ensure that the intended effects of the invention can be more advantageously achieved.

$A^x$ is an organic group having 2 to 30 carbon atoms that includes at least one aromatic ring selected from the group consisting of an aromatic hydrocarbon ring and an aromatic hetero ring.

The term "aromatic ring" used herein refers to a cyclic structure that exhibits aromaticity in a broad sense according to Huckel's rule (i.e., a cyclic conjugated structure that includes (4n+2)π electrons, and a structure that exhibits aromaticity in which lone pairs of heteroatoms (e.g., sulfur, oxygen, or nitrogen) are involved in the π electron system (e.g., thiophene, furan, and benzothiazole).

The organic group having 2 to 30 carbon atoms represented by $A^x$ that includes at least one aromatic ring selected from the group consisting of an aromatic hydrocarbon ring and an aromatic hetero ring, may include a plurality of aromatic rings, and may include an aromatic hydrocarbon ring and an aromatic hetero ring.

Examples of the aromatic hydrocarbon ring include a benzene ring, a naphthalene ring, an anthracene ring, and the like. Examples of the aromatic hetero ring include monocyclic aromatic hetero rings such as a pyrrole ring, a furan ring, a thiophene ring, a pyridine ring, a pyridazine ring, a pyrimidine ring, a pyrazine ring, a pyrazole ring, an imidazole ring, an oxazole ring, and a thiazole ring; fused aromatic hetero rings such as a benzothiazole ring, a benzoxazole ring, a quinoline ring, a phthalazine ring, a benzimidazole ring, a benzopyrazole ring, a benzofuran ring, and a benzothiophene ring; and the like.

The aromatic ring included in $A^x$ may be substituted with a substituent. Examples of the substituent include halogen atoms such as a fluorine atom and a chlorine atom; a cyano group; alkyl groups having 1 to 6 carbon atoms such as a methyl group, an ethyl group, and a propyl group; alkenyl groups having 2 to 6 carbon atoms such as a vinyl group and an allyl group; alkyl halide groups having 1 to 6 carbon atoms such as a trifluoromethyl group; substituted amino groups such as a dimethylamino group; alkoxy groups having 1 to 6 carbon atoms such as a methoxy group, an ethoxy group, and an isopropoxy group; a nitro group; aryl groups such as a phenyl group and a naphthyl group; —C(=O)—R$^4$; —C(=O)—OR$^4$; —SO$_2$R$^4$; and the like. R$^4$ is an alkyl group having 1 to 6 carbon atoms or an aryl group having 6 to 14 carbon atoms.

The aromatic ring included in $A^x$ may be substituted with a plurality of identical or different substituents, and two adjacent substituents may bond to each other to form a ring. The ring formed by two adjacent substituents may be a monocyclic ring, or may be a fused polycyclic ring.

Note that the number of carbon atoms (i.e., 2 to 30) of the organic group represented by $A^x$ refers to the total number of carbon atoms of the organic group excluding the number of carbon atoms of a substituent. This also applies to the number of carbon atoms of the organic group represented by $A^y$.

Examples of the organic group having 2 to 30 carbon atoms represented by $A^x$ that includes at least one aromatic ring selected from the group consisting of an aromatic hydrocarbon ring and an aromatic hetero ring include aromatic cyclic hydrocarbon groups; aromatic heterocyclic groups; alkyl groups having 3 to 30 carbon atoms that include at least one aromatic ring selected from the group consisting of an aromatic hydrocarbon ring and an aromatic hetero ring; alkenyl groups having 4 to 30 carbon atoms that include at least one aromatic ring selected from the group consisting of an aromatic hydrocarbon ring and an aromatic hetero ring; alkynyl groups having 4 to 30 carbon atoms that include at least one aromatic ring selected from the group consisting of an aromatic hydrocarbon ring and an aromatic hetero ring; and the like.

$A^y$ is a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, —C(=O)—R$^3$, —SO$_2$—R$^6$, or an organic group having 2 to 30 carbon atoms that includes at least one aromatic ring selected from the group consisting of an aromatic hydrocarbon ring and an aromatic hetero ring, preferably a hydrogen atom, a substituted or unsubstituted alkyl group having 1 to 12 carbon atoms, a substituted or unsubstituted alkenyl group having 2 to 12 carbon atoms, a substituted or unsubstituted cycloalkyl group having 3 to 12 carbon atoms, —C(=O)—R$^3$, —SO$_2$—R$^6$, or an organic group having 2 to 30 carbon atoms that includes at least one aromatic ring selected from the group consisting of an aromatic hydrocarbon ring and an aromatic hetero ring, and more preferably a hydrogen atom, a substituted or unsubstituted alkyl group having 1 to 6 carbon atoms, or an organic group having 2 to 30 carbon atoms that includes at least one aromatic ring selected from the group consisting of an aromatic hydrocarbon ring and an aromatic hetero ring.

Examples of the alkyl group having 1 to 20 carbon atoms represented by $A^y$ include a methyl group, an ethyl group, an n-propyl group, an isopropyl group, an n-butyl group, a sec-butyl group, a t-butyl group, an n-pentyl group, an isopentyl group, a neopentyl group, an n-hexyl group, an isohexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-icosyl group, and the like. The number of carbon atoms of the substituted or unsubstituted alkyl group having 1 to 20 carbon atoms is preferably 1 to 12, and more preferably 1 to 6.

Examples of a substituent that may substitute the substituted or unsubstituted alkyl group having 1 to 20 carbon atoms represented by $A^y$ include halogen atoms such as a fluorine atom and a chlorine atom; a cyano group; substituted amino groups such as a dimethylamino group; alkoxy groups having 1 to 6 carbon atoms such as a methoxy group, an ethoxy group, and an isopropoxy group; alkoxy groups having 1 to 6 carbon atoms that are substituted with an alkoxy group having 1 to 6 carbon atoms, such as a methoxymethoxy group and a methoxyethoxy group; a nitro group; aryl groups such as a phenyl group and a naphthyl group; cycloalkyl groups having 3 to 8 carbon atoms such as a cyclopropyl group, a cyclopentyl group, and a cyclohexyl group; —C(=O)—R$^4$; —C(=O)—OR$^4$; —SO$_2$R$^4$; a hydroxyl group; and the like. Note that R$^4$ is the same as defined above.

Examples of the alkenyl group having 2 to 20 carbon atoms represented by $A^y$ include a vinyl group, a propenyl group, an isopropenyl group, a butenyl group, a pentenyl group, a hexenyl group, a heptenyl group, an octenyl group, a decenyl group, an undecenyl group, a dodecenyl group, a tridecenyl group, a tetradecenyl group, a pentadecenyl group, a hexadecenyl group, a heptadecenyl group, an octadecenyl group, a nonadecenyl group, an icosenyl group, and the like.

The number of carbon atoms of the substituted or unsubstituted alkenyl group having 2 to 20 carbon atoms is preferably 2 to 12.

Examples of the cycloalkyl group having 3 to 12 carbon atoms represented by $A^y$ include a cyclopropyl group, a cyclobutyl group, a cyclopentyl group, a cyclohexyl group, a cyclooctyl group, and the like.

Examples of a substituent that may substitute the substituted or unsubstituted alkenyl group having 2 to 20 carbon atoms and the substituted or unsubstituted cycloalkyl group having 3 to 12 carbon atoms represented by $A^y$ include halogen atoms such as a fluorine atom and a chlorine atom; a cyano group; substituted amino groups such as a dimethylamino group; alkoxy groups having 1 to 6 carbon atoms such as a methoxy group, an ethoxy group, and an isopropoxy group; a nitro group; aryl groups such as a phenyl group and a naphthyl group; cycloalkyl groups having 3 to 8 carbon atoms such as a cyclopropyl group, a cyclopentyl group, and a cyclohexyl group; —C(=O)—R$^4$; —C(=O)—OR$^4$; —SO$_2$R$^4$; a hydroxyl group; and the like. Note that R$^4$ is the same as defined above.

$R^3$ in —C(=O)—$R^3$ represented by $A^y$ is a substituted or unsubstituted alkyl group having 1 to 20 carbon atoms, a substituted or unsubstituted alkenyl group having 2 to 20 carbon atoms, or a substituted or unsubstituted cycloalkyl group having 3 to 12 carbon atoms. Specific examples of these groups include those mentioned above in connection with the substituted or unsubstituted alkyl group having 1 to 20 carbon atoms, the substituted or unsubstituted alkenyl group having 2 to 20 carbon atoms, and the substituted or unsubstituted cycloalkyl group having 3 to 12 carbon atoms represented by $A^y$.

$R^6$ in —SO$_2$—$R^6$ represented by $A^y$ is an alkyl group having 1 to 20 carbon atoms, an alkenyl group having 2 to 20 carbon atoms, a phenyl group, or a 4-methylphenyl group.

Specific examples of the alkyl group having 1 to 20 carbon atoms and the alkenyl group having 2 to 20 carbon atoms represented by $R^6$ include those mentioned above in connection with the alkyl group having 1 to 20 carbon atoms and the alkenyl group having 2 to 20 carbon atoms represented by $A^y$.

Examples of the organic group having 2 to 30 carbon atoms represented by $A^y$ that includes at least one aromatic ring selected from the group consisting of an aromatic hydrocarbon ring and an aromatic hetero ring, include those mentioned above in connection with $A^x$.

The aromatic ring included in $A^y$ may be substituted with a substituent at an arbitrary position. Examples of the substituent include those mentioned above in connection with a substituent that may substitute the aromatic ring included in $A^x$.

Specific examples of the aromatic ring that may be included in $A^x$ and $A^y$ are shown below. Note that the aromatic ring that may be included in $A^x$ and $A^y$ is not limited thereto. "—" in the following formulas is a bonding hand of the aromatic ring (hereinafter the same).

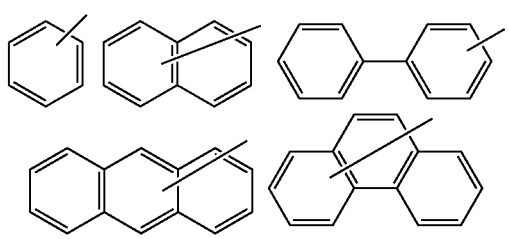

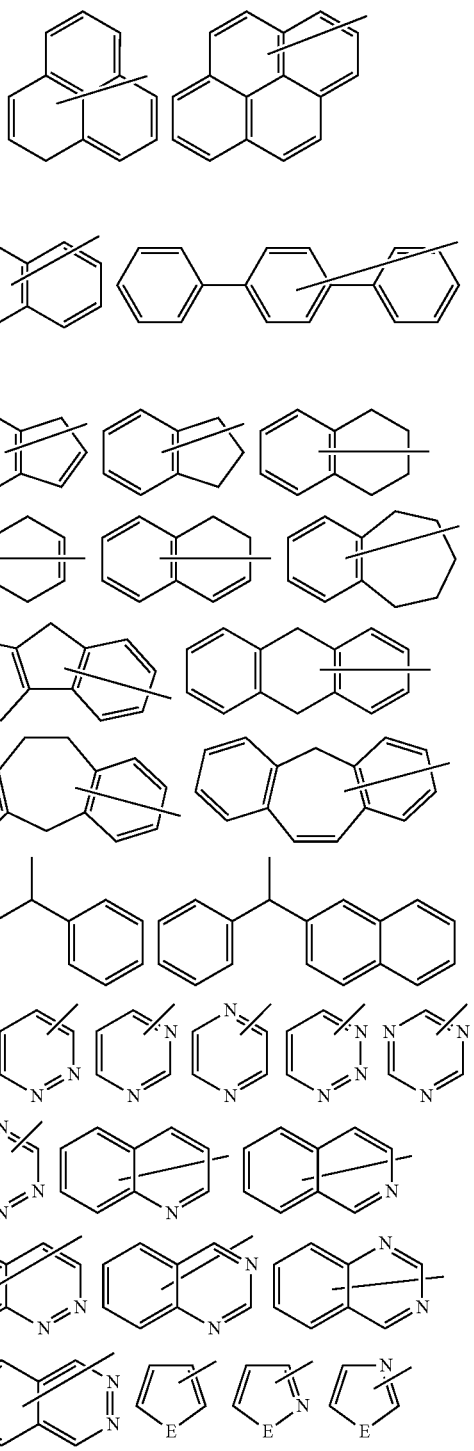

wherein E is NR$^5$, an oxygen atom, or a sulfur atom, and R$^5$ is a hydrogen atom or an alkyl group having 1 to 6 carbon atoms.

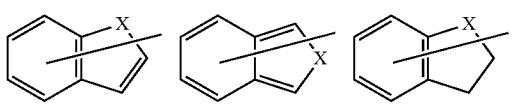

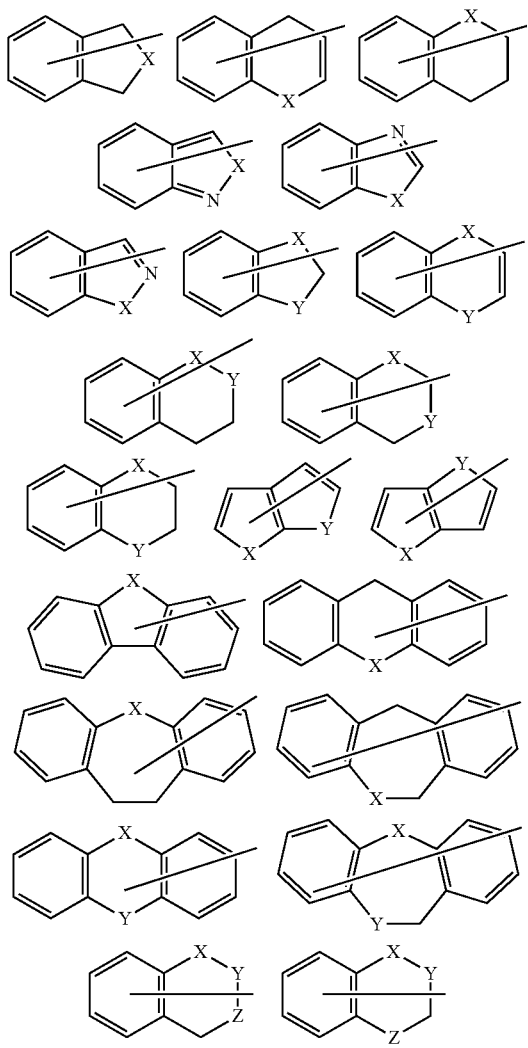

wherein X, Y, and Z are independently NR⁵, an oxygen atom, a sulfur atom, —SO—, or —SO₂—(provided that a case where two or more oxygen atoms, sulfur atoms, —SO—, or —SO₂— are situated at adjacent positions is excluded), and R⁵ is the same as defined above.

Among these, the following aromatic rings are preferable.

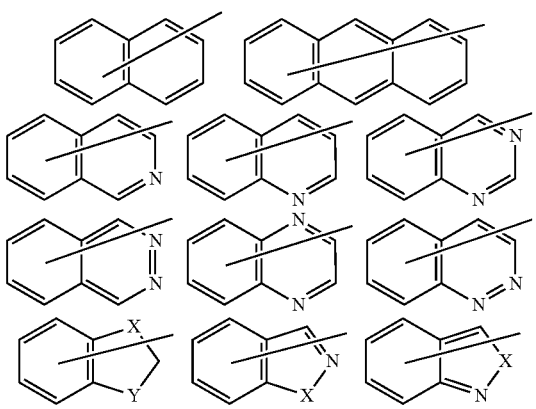

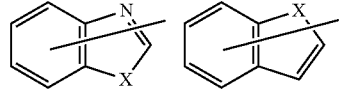

wherein X is NR⁵, an oxygen atom, a sulfur atom, —SO—, or —SO₂—, and R⁵ is a hydrogen atom or an alkyl group having 1 to 6 carbon atoms. Among these, the following aromatic rings are more preferable.

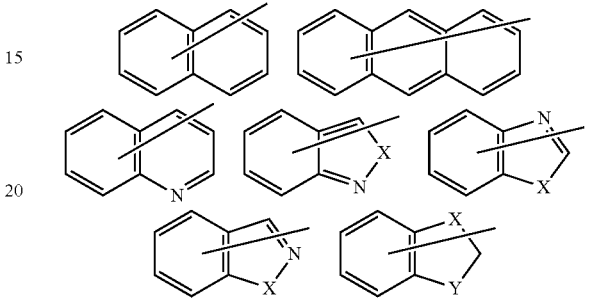

wherein X and Y are the same as defined above. Among these, the following aromatic rings are particularly preferable.

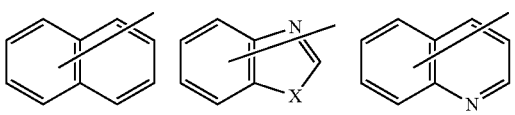

wherein X is the same as defined above.

These groups may be substituted with a substituent at an arbitrary position. Examples of the substituent include those mentioned above in connection with a substituent that may substitute the aromatic ring included in $A^x$.

$A^y$ is preferably a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, —C(=O)—R³, or —SO₂—R⁶. Note that R³ and R⁶ are the same as defined above.

$A^x$ and $A^y$ optionally bond to each other to form a ring. In this case, it is preferable that $A^x$ and $A^y$ bond to each other to form a substituted or unsubstituted unsaturated hetero ring having 4 to 30 carbon atoms, or a substituted or unsubstituted unsaturated carbon ring having 6 to 30 carbon atoms.

The unsaturated hetero ring having 4 to 30 carbon atoms and the unsaturated carbon ring having 6 to 30 carbon atoms are not particularly limited, and may or may not exhibit aromaticity. Examples of the unsaturated hetero ring having 4 to 30 carbon atoms and the unsaturated carbon ring having 6 to 30 carbon atoms are shown below.

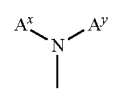

Note that the following rings indicate the above part of the formula (I).

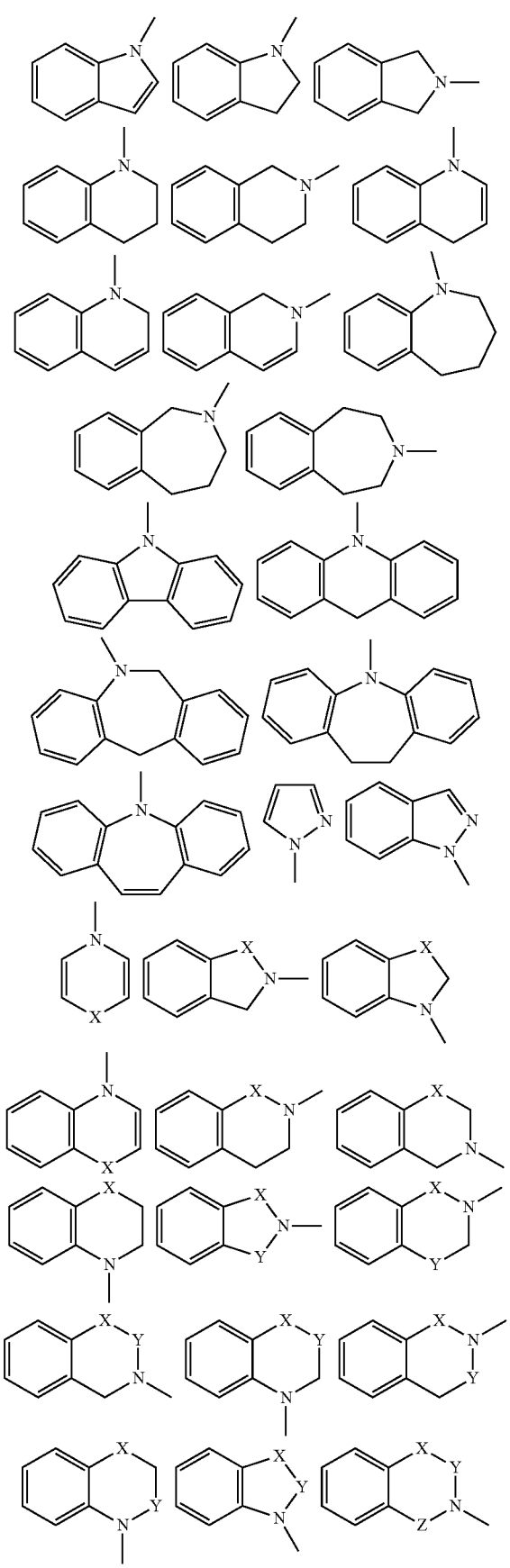
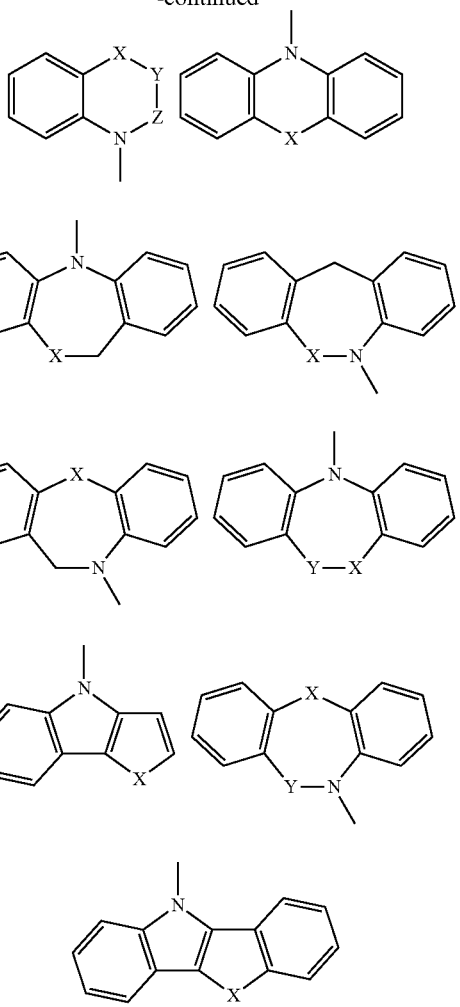

wherein X, Y, and Z are the same as defined above.

The above rings may be substituted with a substituent.

Examples of the substituent include halogen atoms, a cyano group, alkyl groups having 1 to 6 carbon atoms, alkoxy groups having 1 to 6 carbon atoms, a nitro group, —C(=O)—R$^4$, —C(=O)—OR$^4$, —SO$_2$R$^4$, and the like. Note that R$^4$ is the same as defined above.

The total number of π electrons included in A$^x$ and A$^y$ is preferably 4 to 24, and more preferably 6 to 18, in order to ensure that the intended effects of the invention can be more advantageously achieved.

It is preferable that A$^x$ is an aromatic group having 4 to 30 carbon atoms, and A$^y$ be a hydrogen atom, a cycloalkyl group having 3 to 8 carbon atoms, or an alkyl group having 1 to 20 carbon atoms that is optionally substituted with a halogen atom, a cyano group, an alkoxy group having 1 to 6 carbon atoms, or a cycloalkyl group having 3 to 8 carbon atoms, or A$^x$ and A$^y$ bond to each other to form an unsaturated hetero ring or an unsaturated carbon ring.

It is more preferable that A$^x$ be a group among the groups represented by the following formulas, and A$^y$ be a hydrogen atom, a cycloalkyl group having 3 to 8 carbon atoms, or an alkyl group having 1 to 20 carbon atoms that is optionally substituted with a halogen atom, a cyano group, an alkoxy group having 1 to 6 carbon atoms, or a cycloalkyl group having 3 to 8 carbon atoms.

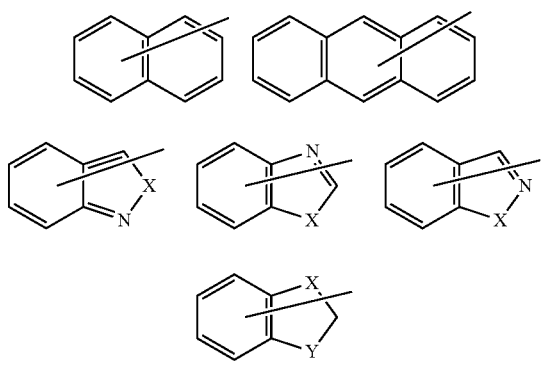

wherein X and Y are the same as defined above.

It is particularly preferable that $A^x$ is a group among the groups represented by the following formulas, and $A^y$ is a hydrogen atom, a cycloalkyl group having 3 to 8 carbon atoms, or an alkyl group having 1 to 12 carbon atoms that is optionally substituted with a halogen atom, a cyano group, an alkoxy group having 1 to 6 carbon atoms, or a cycloalkyl group having 3 to 8 carbon atoms.

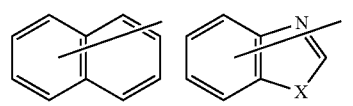

wherein X is the same as defined above.

$A^1$ is a substituted or unsubstituted trivalent aromatic group. The trivalent aromatic group may be a trivalent carbocyclic aromatic group, or may be a trivalent heterocyclic aromatic group. It is preferable that the trivalent aromatic group is a trivalent carbocyclic aromatic group, more preferably a trivalent benzene ring group or a trivalent naphthalene ring group, and still more preferably a trivalent benzene ring group or a trivalent naphthalene ring group represented by the following formulas.

Note that the substituents $Y^1$ and $Y^2$ are also shown in the following formulas so that the bonding state can be easily understood ($Y^1$ and $Y^2$ are the same as defined above; hereinafter the same).

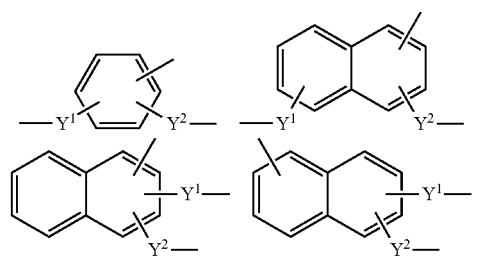

$A^1$ is more preferably a group among the groups represented by the following formulas (A11) to (A25), still more preferably a group among the groups represented by the formulas (A11), (A13), (A15), (A19), and (A23), and particularly preferably the group represented by the formula (A11) or (A23).

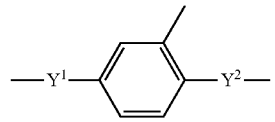
(A11)

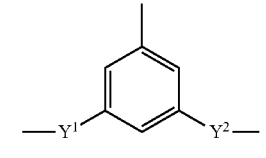
(A12)

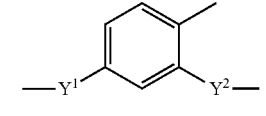
(A13)

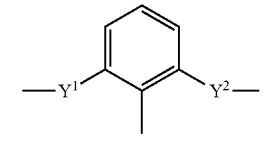
(A14)

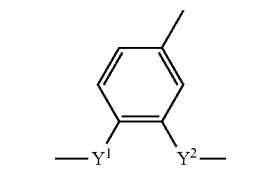
(A15)

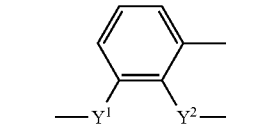
(A16)

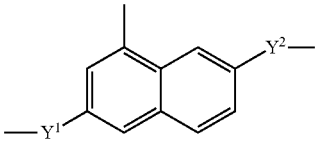
(A17)

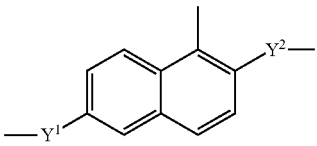
(A18)

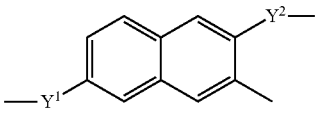
(A19)

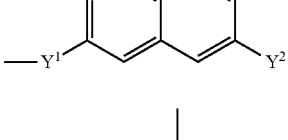
(A20)

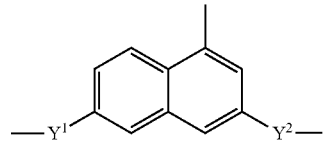
(A21)

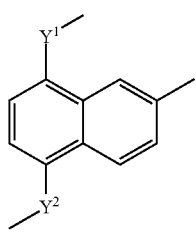
(A22)

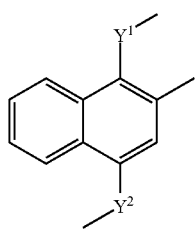
(A23)

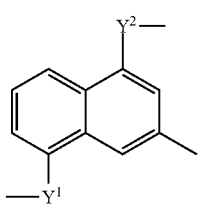
(A24)

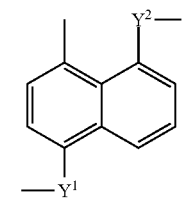
(A25)

Examples of a substituent that may substitute the trivalent aromatic group represented by $A^1$ include those mentioned above in connection with a substituent that may substitute the aromatic ring included in $A^x$. It is preferable that $A^1$ is unsubstituted.

$A^2$ and $A^3$ are independently a substituted or unsubstituted divalent aromatic group having 6 to 30 carbon atoms.

The aromatic group represented by $A^2$ and $A^3$ may be a monocyclic aromatic group, or may be a polycyclic aromatic group.

Specific examples of the aromatic group represented by $A^2$ and $A^3$ include the following groups.

The aromatic group represented by $A^2$ and $A^3$ may be substituted with a substituent at an arbitrary position. Examples of the substituent include halogen atoms, a cyano group, a hydroxyl group, alkyl groups having 1 to 6 carbon atoms, alkoxy groups having 1 to 6 carbon atoms, a nitro group, a —C(=O)—OR group, and the like. Note that R is an alkyl group having 1 to 6 carbon atoms. The substituent is preferably a halogen atom, an alkyl group having 1 to 6 carbon atoms, or an alkoxy group having 1 to 6 carbon atoms. A fluorine atom is preferable as the halogen atom, a methyl group, an ethyl group, and a propyl group are preferable as the alkyl group having 1 to 6 carbon atoms, and a methoxy group and an ethoxy group are preferable as the alkoxy group having 1 to 6 carbon atoms.

It is preferable that $A^2$ and $A^3$ are independently the group represented by the following formula (A31), (A32), or (A33) that may be substituted with a substituent, and more preferably the group represented by the formula (A31) that may be substituted with a substituent.

(A31)

(A32)

(A33)

$Q^1$ is a hydrogen atom, or a substituted or unsubstituted alkyl group having 1 to 6 carbon atoms.

Examples of the substituted or unsubstituted alkyl group having 1 to 6 carbon atoms include those mentioned above in connection with $A^x$.

$Q^1$ is preferably a hydrogen atom or an alkyl group having 1 to 6 carbon atoms, and more preferably a hydrogen atom or a methyl group.

The polymerizable compound according to one embodiment of the invention may be produced by the following reaction, for example.

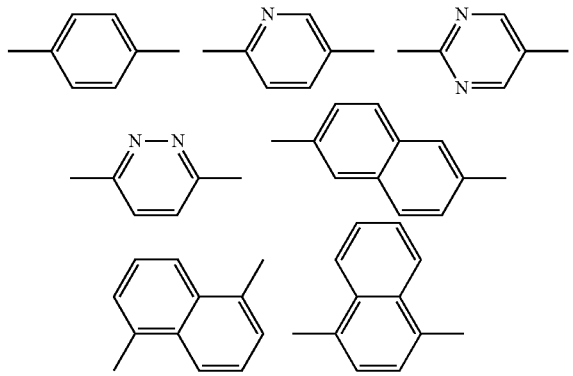

wherein $Y^1$ to $Y^6$, $G^1$, $G^2$, $Z^1$, $Z^2$, $A^x$, $A^y$, $A^1$ to $A^3$, and $Q^1$ are the same as defined above.

Specifically, the hydrazine compound represented by the formula (3) (hydrazine compound (3)) is reacted with the carbonyl compound represented by the formula (4) (carbonyl compound (4)) in a molar ratio (hydrazine compound (3): carbonyl compound (4)) of 1:2 to 2:1 (preferably 1:1.5 to 1.5:1) to produce the polymerizable compound represented by the formula (I) with high selectivity in high yield.

The above reaction may be effected in the presence of an acid catalyst such as an organic acid (e.g., (±)-10-camphorsulfonic acid or p-toluenesulfonic acid) or an inorganic acid (e.g., hydrochloric acid or sulfuric acid). The reaction time may be shortened, and the yield may be improved as a result of adding the acid catalyst. The acid catalyst is normally added in an amount of 0.001 to 1 mol based on 1 mol of the carbonyl compound (4). The acid catalyst may be added directly, or may be added in the form of a solution prepared by dissolving the acid catalyst in an appropriate solvent.

The solvent used for the above reaction is not particularly limited as long as the solvent is inert to the reaction. Examples of the solvent include alcohol-based solvents such as methyl alcohol, ethyl alcohol, n-propyl alcohol, isopropyl alcohol, n-butyl alcohol, isobutyl alcohol, sec-butyl alcohol, and t-butyl alcohol; ether-based solvents such as diethyl ether, tetrahydrofuran, 1,2-dimethoxyethane, 1,4-dioxane, and cyclopentyl methyl ether; ester-based solvents such as ethyl acetate, propyl acetate, and methyl propionate; aromatic hydrocarbon-based solvents such as benzene, toluene, and xylene; aliphatic hydrocarbon-based solvents such as n-pentane, n-hexane, and n-heptane; amide-based solvents such as N,N-dimethylformamide, N-methylpyrrolidone, and hexamethylphosphoric triamide; sulfur-containing solvents such as dimethyl sulfoxide and sulfolane; mixed solvents including two or more solvents among these solvents; and the like.

Among these, alcohol-based solvents, ether-based solvents, and mixed solvents of an alcohol-based solvent and an ether-based solvent are preferable.

The solvent may be used in an appropriate amount taking account of the type of each compound, the reaction scale, and the like. The solvent is normally used in an amount of 1 to 100 g per gram of the hydrazine compound (3).

The reaction proceeds smoothly when the reaction temperature is within the range from −10° C. to the boiling point of the solvent. The reaction time is determined taking account of the reaction scale, and is normally several minutes to several hours.

The hydrazine compound (3) may be produced as described below.

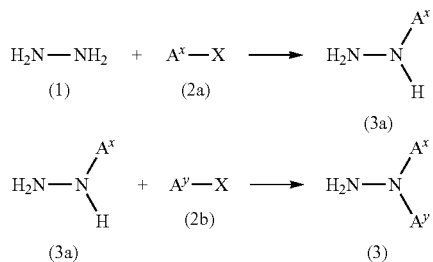

wherein $A^x$ and $A^y$ are the same as defined above, and X is a leaving group (e.g., halogen atom, methanesulfonyloxy group, or p-toluenesulfonyloxy group).

Specifically, the compound represented by the formula (2a) is reacted with the hydrazine (1) in an appropriate solvent in a molar ratio (compound (2a):hydrazine (1)) of 1:1 to 1:20 (preferably 1:2 to 1:10) to obtain the corresponding hydrazine compound (3a), and the hydrazine compound (3a) is reacted with the compound represented by the formula (2b) to obtain the hydrazine compound (3).

Hydrazine monohydrate is normally used as the hydrazine (1). A commercially available product may be used directly as the hydrazine (1).

The solvent used for the above reaction is not particularly limited as long as the solvent is inert to the reaction. Examples of the solvent include alcohol-based solvents such as methyl alcohol, ethyl alcohol, n-propyl alcohol, isopropyl alcohol, n-butyl alcohol, isobutyl alcohol, sec-butyl alcohol, and t-butyl alcohol; ether-based solvents such as diethyl ether, tetrahydrofuran, 1,2-dimethoxyethane, 1,4-dioxane, and cyclopentyl methyl ether; aromatic hydrocarbon-based solvents such as benzene, toluene, and xylene; aliphatic hydrocarbon-based solvents such as n-pentane, n-hexane, and n-heptane; amide-based solvents such as N,N-dimethylformamide, N-methylpyrrolidone, and hexamethylphosphoric triamide; sulfur-containing solvents such as dimethyl sulfoxide and sulfolane; mixed solvents including two or more solvents among these solvents; and the like.

Among these, alcohol-based solvents, ether-based solvents, and mixed solvents of an alcohol-based solvent and an ether-based solvent are preferable.

The solvent may be used in an appropriate amount taking account of the type of each compound, the reaction scale, and the like. The solvent is normally used in an amount of 1 to 100 g per gram of hydrazine.

The reaction proceeds smoothly when the reaction temperature is within the range from −10° C. to the boiling point of the solvent. The reaction time is determined taking account of the reaction scale, and is normally several minutes to several hours.

The hydrazine compound (3) may also be produced by reducing the diazonium salt (5) (see below) using a known method.

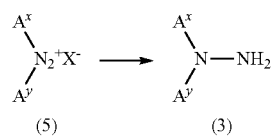

wherein $A^x$ and $A^y$ are the same as defined above, and $X^-$ is an anion that is a counter ion for diazonium. Examples of the anion represented by $X^-$ include inorganic anions such as a hexafluorophosphoric acid ion, a fluoroboric acid ion, a chloride ion, and a sulfuric acid ion; organic anions such as a polyfluoroalkylcarboxylic acid ion, a polyfluoroalkylsulfonic acid ion, a tetraphenylboric acid ion, an aromatic carboxylic acid ion, and an aromatic sulfonic acid ion; and the like.

Examples of a reducing agent used for the above reaction include a metal salt reducing agent.

The term "metal salt reducing agent" normally refers to a compound that includes a metal having a small valence, or a compound that includes a metal ion and a hydrido source (see "*Yuki Gosei Jikkenhou Handbook* (Handbook of Organic Synthesis Experiments)", 1990, edited by The Society of Synthetic Organic Chemistry, Japan, published by Maruzen Co., Ltd., p. 810).

Examples of the metal salt reducing agent include $NaAlH_4$, $NaAlH_p(Or)_q$ (wherein p and q are independently an integer from 1 to 3, provided that p+q=4, and r is an alkyl group having 1 to 6 carbon atoms), LiAlH$_4$, iBu$_2$AlH, LiBH$_4$, NaBH$_4$, SnCl$_2$, CrCl$_2$, TiCl$_3$, and the like.

The reduction reaction may be effected under known reaction conditions. For example, the reduction reaction may be effected under the reaction conditions described in JP-A-2005-336103, "Shin-Jikken Kagaku Koza (New Experimental Chemistry Course)", 1978, Vol. 14, published by Maruzen Co., Ltd., "Jikken Kagaku Koza (Experimental Chemistry Course)", 1992, Vol. 20, published by Maruzen Co., Ltd., or the like.

The diazonium salt (5) may be produced from aniline or the like using a known method.

The carbonyl compound (4) may be produced by appropriately bonding and modifying a plurality of known compounds having a desired structure by arbitrarily combining an ether linkage (—O—)-forming reaction, an ester linkage (—C(=O)—O— or —O—C(=O)—)-forming reaction, a carbonate linkage (—O—C(=O)—O—)-forming reaction, and an amide linkage (—C(=O)NH— or —NHC(=O)—)-forming reaction.

An ether linkage may be formed as described below.
(i) A compound represented by D1-hal (wherein hal is a halogen atom; hereinafter the same) and a compound represented by D2-OMet (wherein Met is an alkali metal (mainly sodium; hereinafter the same)) are mixed and condensed (Williamson synthesis). Note that D1 and D2 are an arbitrary organic group (hereinafter the same).
(ii) A compound represented by D1-hal and a compound represented by D2-OH are mixed and condensed in the presence of a base (e.g., sodium hydroxide or potassium hydroxide).
(iii) A compound represented by D1-J (wherein J is an epoxy group) and a compound represented by D2-OH are mixed and condensed in the presence of a base (e.g., sodium hydroxide or potassium hydroxide).
(iv) A compound represented by D1-OFN (wherein OFN is a group that includes an unsaturated bond) and a compound represented by D2-OMet are mixed and subjected to an addition reaction in the presence of a base (e.g., sodium hydroxide or potassium hydroxide).
(v) A compound represented by D1-hal and a compound represented by D2-OMet are mixed and condensed in the presence of copper or cuprous chloride (Ullmann condensation).

An ester linkage and an amide linkage may be formed as described below.
(vi) A compound represented by D1-COOH and a compound represented by D2-OH or D2-NH$_2$ are subjected to dehydration and condensation in the presence of a dehydration-condensation agent (e.g., N,N-dicyclohexylcarbodiimide).
(vii) A compound represented by D1-COOH is reacted with a halogenating agent to obtain a compound represented by D1-CO-hal, and the compound represented by D1-CO-hal is reacted with a compound represented by D2-OH or D2-NH$_2$ in the presence of a base.
(viii) A compound represented by D1-COOH is reacted with an acid anhydride to obtain a mixed acid anhydride, and the mixed acid anhydride is reacted with a compound represented by D2-OH or D2-NH$_2$.
(ix) A compound represented by D1-COOH and a compound represented by D2-OH or D2-NH$_2$ are subjected to dehydration and condensation in the presence of an acid catalyst or a base catalyst.

The carbonyl compound (4) represented by the formula (4) wherein the group represented by Z$^2$—Y$^6$-G$^2$-Y$^4$-A$^3$-Y$^2$— is identical with the group represented by Z$^1$—Y$^5$-G$^1$-Y$^3$-A$^2$-Y$^1$—, and Y$^1$ is a group represented by Y$^{11}$—C(=O)—O— (hereinafter referred to as "compound (4')") may be produced by the following reaction.

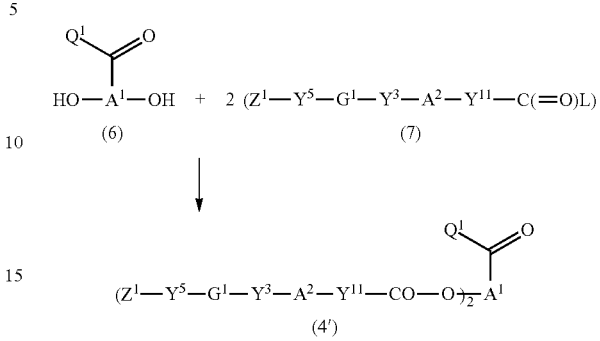

wherein Y$^3$, Y$^5$, G$^1$, A$^1$, A$^2$, and Q$^1$ are the same as defined above, Y$^{11}$ is a group whereby Y$^1$ is Y$^{11}$—C(=O)—O—, Y$^1$ is the same as defined above, and L is a leaving group (e.g., hydroxyl group, halogen atom, methanesulfonyloxy group, or p-toluenesulfonyloxy group).

Specifically, the dihydroxy compound represented by the formula (6) (compound (6)) is reacted with the compound represented by the formula (7) (compound (6)) in a molar ratio (compound (6):compound (7)) of 1:2 to 1:4 (preferably 1:2 to 1:3) to produce the target compound (4') with high selectivity in high yield.

When the compound (7) is a compound (carboxylic acid) represented by the formula (7) wherein L is a hydroxyl group, the target product may be obtained by effecting the reaction in the presence of a dehydration-condensation agent (e.g., 1-ethyl-3-(3-dimethylaminopropyl)carbodiimide hydrochloride or dicyclohexylcarbodiimide).

The dehydration-condensation agent is normally used in an amount of 1 to 3 mol based on 1 mol of the compound (7).

When the compound (7) is a compound (acid halide) represented by the formula (7) wherein L is a halogen atom, the target product may be obtained by effecting the reaction in the presence of a base.

Examples of the base include organic bases such as triethylamine and pyridine, and inorganic bases such as sodium hydroxide, sodium carbonate, and sodium hydrogen carbonate.

The base is normally used in an amount of 1 to 3 mol based on 1 mol of the compound (7).

When the compound (7) is a compound (mixed acid anhydride) represented by the formula (7) wherein L is a methanesulfonyloxy group or a p-toluenesulfonyloxy group, the target product may be obtained in the same manner as in the case where L is a halogen atom.

Examples of the solvent used in the step 2 include chlorine-based solvents such as chloroform and methylene chloride; amide-based solvents such as N-methylpyrrolidone, N,N-dimethylformamide, N,N-dimethylacetamide, and hexamethylphosphoric triamide; ether-based solvents such as 1,4-dioxane, cyclopentyl methyl ether, tetrahydrofuran, tetrahydropyran, and 1,3-dioxolane; sulfur-containing solvents such as dimethyl sulfoxide and sulfolane; aromatic hydrocarbon-based solvents such as benzene, toluene, and xylene; aliphatic hydrocarbon-based solvents such as n-pentane, n-hexane, and n-octane; alicyclic hydrocarbon-based solvents such as cyclopentane and cyclohexane; mixed solvents including two or more solvents among these solvents; and the like.

The solvent may be used in an appropriate amount taking account of the type of each compound, the reaction scale, and the like. The solvent is normally used in an amount of 1 to 50 g per gram of the hydroxy compound (6).

Most of the compounds (7) are known compounds. The carbonyl compound (7) may be produced by appropriately bonding and modifying a plurality of known compounds having a desired structure by arbitrarily combining an ether linkage (—O—)-forming reaction, an ester linkage (—C(=O)—O— or —O—C(=O)—)-forming reaction, a carbonate linkage (—O—C(=O)—O—)-forming reaction, and an amide linkage (—C(=O)NH— or —NHC(=O)—)-forming reaction.

The target product may be isolated by performing a post-treatment operation normally employed in organic chemistry after completion of the reaction, optionally followed by a known purification/separation means such as column chromatography, recrystallization, or distillation.

The structure of the target product may be identified by measurement (e.g., NMR spectrometry, IR spectrometry, or mass spectrometry), elementary analysis, or the like.

2) Polymerizable Composition

A polymerizable composition according to one embodiment of the invention includes the polymerizable compound according to one embodiment of the invention, and an initiator. The initiator is used to more efficiently polymerize the polymerizable composition according to one embodiment of the invention.

The initiator may be appropriately selected depending on the type of the polymerizable group included in the polymerizable compound. For example, a radical initiator may be used when the polymerizable group is a radically polymerizable group. An anionic initiator may be used when the polymerizable group is an anionically polymerizable group. A cationic initiator may be used when the polymerizable group is a cationically polymerizable group.

Examples of the radical initiator include a thermal radical generator that is a compound that generates active species that initiate polymerization of the polymerizable compound upon heating, and a photo-radical generator that is a compound that generates active species that initiate polymerization of the polymerizable compound upon exposure to exposure light (e.g., visible rays, ultraviolet rays (e.g., i-line), deep ultraviolet rays, electron beams, or X-rays). It is preferable to use the photo-radical generator.

Examples of the photo-radical generator include acetophenone-based compounds, biimidazole-based compounds, triazine-based compounds, O-acyloxime-based compounds, onium salt-based compounds, benzoin-based compounds, benzophenone-based compounds, α-diketone-based compounds, polynuclear quinone-based compounds, xanthone-based compounds, diazo-based compounds, imide sulfonate-based compounds, and the like. These compounds generate active radicals and/or an active acid upon exposure. These photo-radical generators may be used either alone or in combination.

Specific examples of the acetophenone-based compounds include 2-hydroxy-2-methyl-1-phenylpropan-1-one, 2-methyl-1-[4-(methylthio)phenyl]-2-morpholinopropan-1-one, 2-benzyl-2-dimethylamino-1-(4-morpholinophenyl)butan-1-one, 1-hydroxycyclohexyl phenyl ketone, 2,2-dimethoxy-1,2-diphenylethan-1-one, 1,2-octanedione, 2-benzyl-2-dimethylamino-4'-morpholinobutyrophenone, and the like.

Specific examples of the biimidazole-based compounds include 2,2'-bis(2-chlorophenyl)-4,4',5,5'-tetrakis(4-ethoxycarbonylphenyl)-1,2'-biimidazole, 2,2'-bis(2-bromophenyl)-4,4',5,5'-tetrakis(4-ethoxycarbonylphenyl)-1,2'-biimidazole, 2,2'-bis(2-chlorophenyl)-4,4',5,5'-tetraphenyl-1,2'-biimidazole, 2,2'-bis(2,4-dichlorophenyl)-4,4',5,5'-tetraphenyl-1,2'-biimidazole, 2,2'-bis(2,4,6-trichlorophenyl)-4,4',5,5'-tetraphenyl-1,2'-biimidazole, 2,2'-bis(2-bromophenyl)-4,4',5,5'-tetraphenyl-1,2'-biimidazole, 2,2'-bis(2,4-dibromophenyl)-4,4',5,5'-tetraphenyl-1,2'-biimidazole, 2,2'-bis(2,4,6-tribromophenyl)-4,4',5,5'-tetraphenyl-1,2'-biimidazole, and the like.

When using a biimidazole-based compound as a photoinitiator, it is preferable to use a hydrogen donor in combination with the biimidazole-based compound since sensitivity can be further improved.

The term "hydrogen donor" used herein refers to a compound that can donate a hydrogen atom to radicals generated by the biimidazole-based compound upon exposure. A mercaptan-based compound, an amine-based compound, and the like are preferable as the hydrogen donor.

Examples of the mercaptan-based compound include 2-mercaptobenzothiazole, 2-mercaptobenzoxazole, 2-mercaptobenzimidazole, 2,5-dimercapto-1,3,4-thiadiazole, 2-mercapto-2,5-dimethylaminopyridine, and the like. Examples of the amine-based compound include 4,4'-bis(dimethylamino)benzophenone, 4,4'-bis(diethylamino)benzophenone, 4-dimethylaminoacetophenone, 4-dimethylaminopropiophenone, ethyl-4-dimethylaminobenzoate, 4-dimethylaminobenzoic acid, 4-dimethylaminobenzonitrile, and the like.

Specific examples of the triazine-based compounds include triazine-based compounds that include a halomethyl group, such as 2,4,6-tris(trichloromethyl)-s-triazine, 2-methyl-4,6-bis(trichloromethyl)-s-triazine, 2-[2-(5-methylfuran-2-yl)ethenyl]-4,6-bis(trichloromethyl)-s-triazine, 2-[2-(furan-2-yl)ethenyl]-4,6-bis(trichloromethyl)-s-triazine, 2-[2-(4-diethylamino-2-methylphenyl)ethenyl]-4,6-bis(trichloromethyl)-s-triazine, 2-[2-(3,4-dimethoxyphenyl)ethenyl]-4,6-bis(trichloromethyl)-s-triazine, 2-(4-methoxyphenyl)-4,6-bis(trichloromethyl)-s-triazine, 2-(4-ethoxystyryl)-4,6-bis(trichloromethyl)-s-triazine, and 2-(4-n-butoxyphenyl)-4,6-bis(trichloromethyl)-s-triazine.

Specific examples of the O-acyloxime-based compounds include 1-[4-(phenylthio)phenyl]-heptane-1,2-dione-2-(O-benzoyloxime), 1-[4-(phenylthio)phenyl]-octane-1,2-dione-2-(O-benzoyloxime), 1-[4-(benzoyl)phenyl]-octane-1,2-dione-2-(O-benzoyloxime), 1-[9-ethyl-6-(2-methylbenzoyl)-9H-carbazol-3-yl]-ethanone-1-(O-acetyloxime), 1-[9-ethyl-6-(3-methylbenzoyl)-9H-carbazol-3-yl]-ethanone-1-(O-acetyloxime), 1-(9-ethyl-6-benzoyl-9H-carbazol-3-yl)-ethanone-1-(O-acetyloxime), ethanone-1-[9-ethyl-6-(2-methyl-4-tetrahydrofuranylbenzoyl)-9H-carbazol-3-yl]-1-(O-acetyloxime), ethanone-1-[9-ethyl-6-(2-methyl-4-tetrahydropyranylbenzoyl)-9H-carbazol-3-yl]-1-(O-acetyloxime), ethanone-1-[9-ethyl-6-(2-methyl-5-tetrahydrofuranylbenzoyl)-9H-carbazol-3-yl]-1-(O-acetyloxime), ethanone-1-[9-ethyl-6-(2-methyl-5-tetrahydropyranylbenzoyl)-9H-carbazol-3-yl]-1-(O-acetyloxime), ethanone-1-[9-ethyl-6-{2-methyl-4-(2,2-dimethyl-1,3-dioxolanyl)benzoyl}-9H-carbazol-3-yl]-1-(O-acetyloxime), ethanone-1-[9-ethyl-6-(2-methyl-4-tetrahydrofuranylmethoxybenzoyl)-9H-carbazol-3-yl]-1-(O-acetyloxime), ethanone-1-[9-ethyl-6-(2-methyl-4-tetrahydropyranylmethoxybenzoyl)-9H-carbazol-3-yl]-1-(O-acetyloxime), ethanone-1-[9-ethyl-6-(2-methyl-5-tetrahydrofuranylmethoxybenzoyl)-9H-carbazol-3-yl]-1-(O-acetyloxime), ethanone-1-[9-ethyl-6-(2-methylbenzoyl)-9H-carbazol-3-yl]-1-(O-acetyloxime), ethanone-1-[9-ethyl-6-(2-methyl-5-tetrahydropyranylmethoxybenzoyl)-9H-carbazol-3-yl]-1-(O-acetyloxime), ethanone-1-[9-ethyl-6-

{2-methyl-4-(2,2-dimethyl-1,3-dioxolanyl)
methoxybenzoyl}-9H-carbazol-3-yl]-1-(O-acetyloxime),
and the like.

A commercially available photo-radical generator may be used directly. Specific examples of a commercially available photo-radical generator include Irgacure 907, Irgacure 184, Irgacure 369, Irgacure 651, Irgacure 819, Irgacure 907, Irgacure OXE02 (manufactured by BASF); Adekaoptomer N1919 (manufactured by Adeka Corporation); and the like.

Examples of the anionic initiator include alkyllithium compounds; monolithium salts or monosodium salts of biphenyl, naphthalene, pyrene, and the like; polyfunctional initiators such as dilithiums and trilithium salts; and the like.

Examples of the cationic initiator include proton acids such as sulfuric acid, phosphoric acid, perchloric acid, and trifluoromethanesulfonic acid; Lewis acids such as boron trifluoride, aluminum chloride, titanium tetrachloride, and tin tetrachloride; an aromatic onium salt or a combination of an aromatic onium salt and a reducing agent; and the like.

These initiators may be used either alone or in combination.

The initiator is normally added to the polymerizable composition according to one embodiment of the invention in an amount of 0.1 to 30 parts by weight, and preferably 0.5 to 10 parts by weight, based on 100 parts by weight of the polymerizable compound.

It is preferable to add a surfactant to the polymerizable composition according to one embodiment of the invention in order to adjust surface tension. The surfactant is not particularly limited, but is preferably a nonionic surfactant. Examples of the nonionic surfactant include an oligomer having a molecular weight of about several thousand, such as KH-40 (manufactured by AGC Seimi Chemical Co., Ltd.). The surfactant is normally added to the polymerizable composition according to one embodiment of the invention in an amount of 0.01 to 10 parts by weight, and preferably 0.1 to 2 parts by weight, based on 100 parts by weight of the polymerizable compound.

The polymerizable composition according to one embodiment of the invention may further include an additional additive such as an additional copolymerizable monomer, a metal, a metal complex, a dye, a pigment, a fluorescent material, a phosphorescent material, a leveling agent, a thixotropic agent, a gelling agent, a polysaccharide, a UV absorber, an IR (infrared) absorber, an antioxidant, an ion-exchange resin, or a metal oxide (e.g., titanium oxide). Each additive is normally added to the polymerizable composition according to one embodiment of the invention in an amount of 0.1 to 20 parts by weight based on 100 parts by weight of the polymerizable compound.

The polymerizable composition according to one embodiment of the invention may be prepared by mixing and dissolving given amounts of the polymerizable compound according to one embodiment of the invention, the initiator, and an optional additive in an appropriate solvent.

Examples of the solvent include ketones such as cyclopentanone, cyclohexanone, and methyl ethyl ketone; acetates such as butyl acetate and amyl acetate; halogenated hydrocarbons such as chloroform, dichloromethane, and dichloroethane; ethers such as 1,4-dioxane, cyclopentyl methyl ether, tetrahydrofuran, tetrahydropyran, and 1,3-dioxolane; and the like.

The polymerizable composition thus obtained is useful as a raw material for producing a polymer or an optically anisotropic article according to the embodiments of the invention (described below).

3) Polymer

A polymer according to one embodiment of the invention is (1) a polymer obtained by polymerizing the polymerizable compound according to one embodiment of the invention, or (2) a polymer obtained by polymerizing the polymerizable composition according to one embodiment of the invention.

The term "polymerization" used herein refers to a chemical reaction in a broad sense including a normal polymerization reaction and a crosslinking reaction.

(1) Polymer Obtained by Polymerizing Polymerizable Compound

The polymer obtained by polymerizing the polymerizable compound according to one embodiment of the invention may be a homopolymer of the polymerizable compound according to one embodiment of the invention, a copolymer of two or more types of the polymerizable compound according to one embodiment of the invention, or a copolymer of the polymerizable compound according to one embodiment of the invention and an additional copolymerizable monomer.

Examples of the additional copolymerizable monomer include, but are not limited to, 4'-methoxyphenyl 4-(2-methacryloyloxyethyloxy)benzoate, biphenyl 4-(6-methacryloyloxyhexyloxy)benzoate, 4'-cyanobiphenyl 4-(2-acryloyloxyethyloxy)benzoate, 4'-cyanobiphenyl 4-(2-methacryloyloxyethyloxy)benzoate, 3',4'-difluorophenyl 4-(2-methacryloyloxyethyloxy)benzoate, naphthyl 4-(2-methacryloyloxyethyloxy)benzoate, 4-acryloyloxy-4'-decylbiphenyl, 4-acryloyloxy-4'-cyanobiphenyl, 4-(2-acryloyloxyethyloxy)-4'-cyanobiphenyl, 4-(2-methacryloyloxyethyloxy)-4'-methoxybiphenyl, 4-(2-methacryloyloxyethyloxy)-4'-(4"-fluorobenzyloxy)biphenyl, 4-acryloyloxy-4'-propylcyclohexylphenyl, 4-methacryloyl-4'-butylbicyclohexyl, 4-acryloyl-4'-amyltolan, 4-acryloyl-4'-(3,4-difluorophenyl)bicyclohexyl, (4-amylphenyl) 4-(2-acryloyloxyethyl)benzoate, (4-(4'-propylcyclohexyl)phenyl) 4-(2-acryloyloxyethyl)benzoate, and the like.

Examples of a commercially available product of the additional copolymerizable monomer include LC-242 (manufactured by BASF) and the like. The compounds disclosed in JP-A-2007-002208, JP-A-2009-173893, JP-A-2009-274984, JP-A-2010-030979, JP-A-2010-031223, JP-A-2011-006360, and the like may be used as the additional copolymerizable monomer.

A polyfunctional monomer that includes a plurality of polymerizable unsaturated groups (e.g., acryloyl group, methacryloyl group, vinyl group, and allyl group) may also be used as the additional copolymerizable monomer.

Examples of the polyfunctional monomer include alkanediol diacrylates such as 1,2-butanediol diacrylate, 1,3-butanediol diacrylate, 1,4-butanediol diacrylate, neopentanediol diacrylate, and 1,6-hexanediol diacrylate, alkanediol dimethacrylates such as 1,2-butanediol dimethacrylate, 1,3-butanediol dimethacrylate, 1,4-butanediol dimethacrylate, neopentanediol dimethacrylate, and 1,6-hexanediol dimethacrylate, polyethylene glycol diacrylates such as ethylene glycol diacrylate, diethylene glycol diacrylate, triethylene glycol diacrylate, and tetraethylene glycol diacrylate, polypropylene glycol diacrylates such as propylene glycol diacrylate, dipropylene glycol diacrylate, tripropylene glycol diacrylate, and tetrapropylene glycol diacrylate, polyethylene glycol dimethacrylates such as ethylene glycol dimethacrylate, diethylene glycol dimethacrylate, triethylene glycol dimethacrylate, and tetraethylene glycol dimethacrylate, polypropylene glycol dimethacrylates such as propylene glycol dimethacrylate, dipropylene glycol dimethacrylate, tripropylene glycol dimethacrylate, and tetrapropylene glycol dimethacrylate, polyethylene glycol divinyl ethers such as ethylene glycol divinyl ether, diethylene glycol divinyl ether, triethylene glycol divinyl ether, and tetraethylene glycol divinyl ether, polyethylene glycol diallyl ethers such as ethylene glycol diallyl ether, diethylene glycol diallyl ether, triethylene glycol diallyl ether, and tetraethylene glycol diallyl ether; bisphenol F ethoxylate diacrylate; bisphenol F ethoxylate dimethacrylate; bisphenol A ethoxylate diacrylate; bisphenol A ethoxylate dimethacrylate; trimethylolpropane triacrylate; trimethylolpropane trimethacrylate; trimethylolpropane ethoxylate triacrylate; trimethylolpropane ethoxylate trimethacrylate; trimethylolpropane propoxylate triacrylate; trimethylolpropane propoxylate trimethacrylate; isocyanuric acid ethoxylate triacrylate; glycerol ethoxylate triacrylate; glycerol propoxylate triacrylate; pentaerythritol ethoxylate tetraacrylate; ditrimethylolpropane ethoxylate tetraacrylate; dipentaerythritol ethoxylate hexacrylate, and the like.

The polymerizable compound according to one embodiment of the invention may be (co)polymerized optionally together with the additional copolymerizable monomer in the presence of an appropriate initiator. The initiator is used in an amount similar to that of the initiator included in the polymerizable composition.

When the polymer according to one embodiment of the invention is a copolymer of the polymerizable compound according to one embodiment of the invention and the additional copolymerizable monomer, the content of constituent units derived from the polymerizable compound according to one embodiment of the invention is not particularly limited, but is preferably 50 wt % or more, and more preferably 70 wt % or more, based on the amount of the total constituent units. When the content of constituent units derived from the polymerizable compound is within the above range, a polymer that has a high glass transition temperature (Tg) and high hardness can be obtained.

The polymer (1) may be produced by (A) (co)polymerizing the polymerizable compound optionally together with the additional copolymerizable monomer in an appropriate organic solvent in the presence of an appropriate initiator, isolating the target polymer, dissolving the polymer in an appropriate organic solvent to prepare a solution, applying the solution to an appropriate substrate to obtain a film, and drying the film, followed by optional heating, or (B) applying a solution prepared by dissolving the polymerizable compound in an organic solvent optionally together with the additional copolymerizable monomer to a substrate by a known coating method, removing the solvent, and effecting polymerization by applying heat or activated energy rays, for example.

Examples of the initiator include those mentioned above in connection with the initiator included in the polymerizable composition.

The organic solvent used for the method (A) (i.e., used for polymerization) is not particularly limited as long as the organic solvent is inert. Examples of the organic solvent include aromatic hydrocarbons such as toluene, xylene, and mesitylene; ketones such as cyclohexanone, cyclopentanone, and methyl ethyl ketone; acetates such as butyl acetate and amyl acetate; halogenated hydrocarbons such as chloroform, dichloromethane, and dichloroethane; ethers such as cyclopentyl methyl ether, tetrahydrofuran, and tetrahydropyran; and the like. Among these, it is preferable to use a compound having a boiling point of 60 to 250° C., and more preferably 60 to 150° C., from the viewpoint of handling capability.

Examples of the organic solvent used to dissolve the polymer in the method (A) and the organic solvent used for the method (B) include ketones such as acetone, methyl ethyl ketone, methyl isobutyl ketone, cyclopentanone, and cyclohexanone; esters such as butyl acetate and amyl acetate; halogenated hydrocarbons such as dichloromethane, chloroform, and dichloroethane; ethers such as tetrahydrofuran, tetrahydropyran, 1,2-dimethoxyethane, 1,4-dioxane, cyclopentyl methyl ether, 1,3-dioxolane; aprotic polar solvents such as N,N-dimethylformamide, N,N-dimethylacetamide, dimethyl sulfoxide, γ-butyrolactone, and N-methylpyrrolidone; and the like. Among these, it is preferable to use a compound having a boiling point of 60 to 200° C. from the viewpoint of handling capability. These solvents may be used either alone or in combination.

A substrate formed of a known organic or inorganic material may be used as the substrate. Examples of the organic material include polycycloolefins (e.g., Zeonex, Zeonor (registered trademark; manufactured by Zeon Corporation), Arton (registered trademark; manufactured by JSR Corporation), and Apel (registered trademark; manufactured by Mitsui Chemicals Inc.)), polyethylene terephthalate, polycarbonate, polyimide, polyamide, polymethyl methacrylate, polystyrene, polyvinyl chloride, polytetrafluoroethylene, cellulose, cellulose triacetate, polyethersulfone, and the like. Examples of the inorganic material include silicon, glass, calcite, and the like. It is preferable to use an organic material.

The substrate may be a single-layer substrate, or may be a laminate.

The substrate is preferably a substrate formed of an organic material, and more preferably a resin film formed of an organic material.

The polymer solution (method (A)) or the solution subjected to polymerization (method (B)) may be applied to the substrate by a known coating method. Examples of the coating method include a curtain coating method, an extrusion coating method, a roll coating method, a spin coating method, a dip coating method, a bar coating method, a spray coating method, a slide coating method, a print coating method, and the like.

(2) Polymer Obtained by Polymerizing Polymerizable Composition

The polymer according to one embodiment of the invention can be easily obtained by polymerizing the polymerizable composition according to one embodiment of the invention. It is preferable to use a polymerizable composition that includes the above initiator (particularly a photoinitiator) in order to ensure efficient polymerization.

It is preferable to produce the polymer according to one embodiment of the invention by applying the polymerizable composition according to one embodiment of the invention to a substrate, and polymerizing the applied polymerizable composition (i.e., method (B)). Examples of the substrate include a substrate used to produce an optically anisotropic article (described later).

The polymerizable composition according to one embodiment of the invention may be applied to the substrate by a known coating method (e.g., bar coating method, spin coating method, roll coating method, gravure coating method, spray coating method, die coating method, cap coating method, or dipping method). A known organic solvent may be added to the polymerizable composition in order to improve the applicability of the polymerizable composition. In this case, it is preferable to remove the organic solvent by air-drying, drying by heating, drying under reduced pressure, drying by heating under reduced pressure, or the like after applying the polymerizable composition to the substrate.

The polymerizable compound or the polymerizable composition according to the embodiments of the invention may be polymerized by applying activated energy rays, applying a thermal polymerization method, or the like. It is preferable to polymerize the polymerizable compound or the polymerizable composition by applying activated energy rays since heating is unnecessary (i.e., the reaction can be effected at room temperature). It is preferable to apply light (e.g., ultraviolet rays) from the viewpoint of convenience.

The temperature during application of activated energy rays is preferably 30° C. or less. The dose is normally 1 W/m² to 10 kW/m², and preferably 5 W/m² to 2 kW/m².

A polymer obtained by polymerizing the polymerizable compound or the polymerizable composition according to the embodiments of the invention may be independently used after removing the polymer from the substrate, or may be used directly as an optical film organic material or the like without removing the polymer from the substrate.

The number average molecular weight of the polymer according to one embodiment of the invention thus obtained is preferably 500 to 500,000, and more preferably 5000 to 300,000. When the number average molecular weight of the polymer is within the above range, the resulting film exhibits high hardness and an excellent handling capability. The number average molecular weight of the polymer may be determined by gel permeation chromatography (GPC) using monodisperse polystyrene as a standard (eluant: tetrahydrofuran).

It is considered that the polymer according to one embodiment of the invention has a structure in which crosslinking points are uniformly present in the molecule, and exhibits high crosslinking efficiency and excellent hardness.

The polymer according to one embodiment of the invention makes it possible to inexpensively obtain an optical film that achieves uniform conversion of polarized light over a wide wavelength band.

4) Optically Anisotropic Article

An optically anisotropic article according to one embodiment of the invention includes the polymer according to one embodiment of the invention.

The optically anisotropic article according to one embodiment of the invention may be obtained by forming an alignment film on a substrate, and forming a liquid crystal layer on the alignment film using the polymer according to one embodiment of the invention.

The alignment film is formed on the surface of the substrate in order to achieve in-plane alignment of an organic semiconductor compound in one direction.

The alignment film may be obtained by applying a solution (alignment film composition) that includes a polymer (e.g., polyimide, polyvinyl alcohol, polyester, polyallylate, polyamideimide, or polyetherimide) to the substrate to form a film, drying the film, and subjecting the film to a rubbing treatment in one direction, for example.

The thickness of the alignment film is preferably 0.001 to 5 µm, and more preferably 0.001 to 1 µm.

The rubbing treatment may be performed on the alignment film or the substrate. The rubbing treatment may be implemented by an arbitrary method. For example, the alignment film may be rubbed in a given direction using a roll around which a cloth or felt formed of synthetic fibers (e.g., nylon) or natural fibers (e.g., cotton) is wound. It is preferable to wash the alignment film with isopropyl alcohol or the like after the rubbing treatment in order to remove fine powder (foreign substances) formed during the rubbing treatment to clean the surface of the alignment film.

The alignment film may be provided with a function of achieving in-plane alignment of a cholesteric liquid crystal layer by applying polarized UV rays to the surface of the alignment film.

The liquid crystal layer may be formed on the alignment film using the polymer according to one embodiment of the invention using the method described above in connection with the polymer according to one embodiment of the invention.

Since the optically anisotropic article according to one embodiment of the invention is produced using the polymer according to one embodiment of the invention, the optically anisotropic article can be produced at low cost, achieves uniform conversion of polarized light over a wide wavelength band, and shows satisfactory performance.

Examples of the optically anisotropic article according to one embodiment of the invention include a retardation film, an alignment film for liquid crystal display elements, a polarizer, a viewing angle enhancement film, a color filter, a low-pass filter, an optical polarization prism, an optical filter, and the like.

EXAMPLES

The invention is further described below by way of examples. Note that the invention is not limited to the following examples.

Example 1

Synthesis of Compound 1

Compound 1

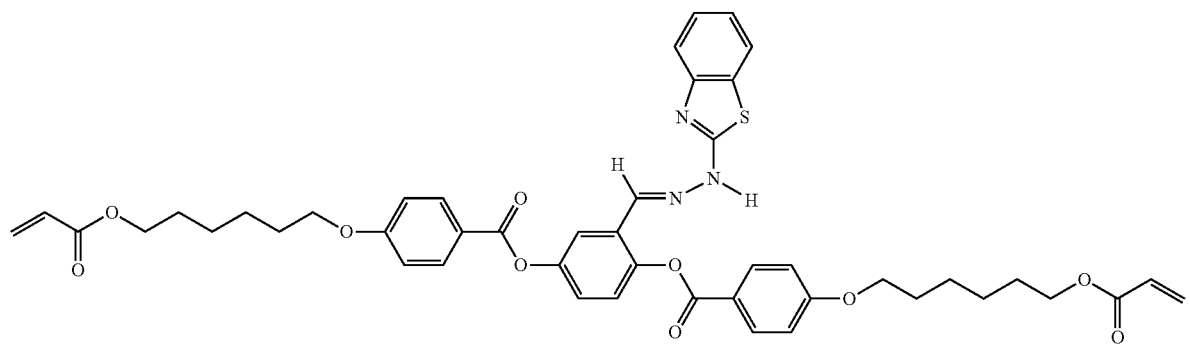

Step 1: Synthesis of Intermediate A

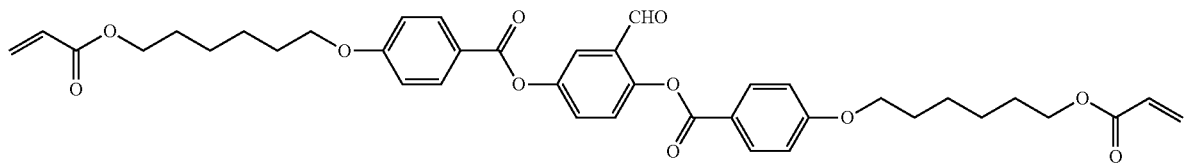

Intermediate A

A four-necked reactor equipped with a thermometer was charged with 20 g (144.8 mmol) of 2,5-dihydroxybenzaldehyde, 105.8 g (362.0 mmol) of 4-(6-acryloylhex-1-yloxy) benzoic acid (manufactured by DKSH Japan K.K.), 5.3 g (43.4 mmol) of 4-(dimethylamino)pyridine, and 200 ml of N-methylpyrrolidone under a nitrogen stream to prepare a homogeneous solution. After the addition of 83.3 g (434.4 mmol) of 1-ethyl-3-(3-dimethylaminopropyl)carbodiimide hydrochloride (WSC) to the solution, the mixture was stirred at 25° C. for 12 hours. After completion of the reaction, the reaction mixture was added to 1.5 l of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=9:1 (volume ratio)) to obtain 75 g of an intermediate A as a white solid (yield: 75.4%).

The structure of the target product was identified by $^1$H-NMR.

$^1$H-NMR (400 MHz, CDCl$_3$, TMS, δ ppm): 10.20 (s, 1H), 8.18-8.12 (m, 4H), 7.78 (d, 1H, J=2.8 Hz), 7.52 (dd, 1H, J=2.8 Hz, 8.7 Hz), 7.38 (d, 1H, J=8.7 Hz), 7.00-6.96 (m, 4H), 6.40 (dd, 2H, J=1.4 Hz, 17.4 Hz), 6.12 (dd, 2H, J=10.6 Hz, 17.4 Hz), 5.82 (dd, 2H, J=1.4 Hz, 10.6 Hz), 4.18 (t, 4H, J=6.4 Hz), 4.08-4.04 (m, 4H), 1.88-1.81 (m, 4H), 1.76-1.69 (m, 4H), 1.58-1.42 (m, 8H).

Step 2: Synthesis of Compound 1

A four-necked reactor equipped with a thermometer was charged with 10.5 g (15.3 mmol) of the intermediate A synthesized by the step 1, 3.0 g (18.3 mmol) of 2-hydrazinobenzothiazole, and 80 ml of tetrahydrofuran (THF) under a nitrogen stream to prepare a homogeneous solution. After the addition of 18 mg (0.08 mmol) of (±)-10-camphorsulfonic acid to the solution, the mixture was stirred at 25° C. for 3 hours. After completion of the reaction, the reaction mixture was added to 800 ml of 10% sodium bicarbonate water, and extracted twice with 100 ml of ethyl acetate. The ethyl acetate layer was collected, and dried over anhydrous sodium sulfate, and sodium sulfate was filtered off Ethyl acetate was evaporated from the filtrate under reduced pressure using a rotary evaporator to obtain a light yellow solid. The light yellow solid was purified by silica gel column chromatography (toluene:ethyl acetate=8:2 (volume ratio)) to obtain 8.0 g of a compound 1 as a light yellow solid (yield: 62.7%).

The structure of the target product was identified by $^1$H-NMR and mass spectroscopy.

$^1$H-NMR (500 MHz, DMSO-d$_6$, TMS, δ ppm): 12.30 (br, 1H), 8.19 (s, 1H), 8.17-8.12 (m, 4H), 7.76 (d, 1H, J=3.0 Hz), 7.68 (d, 1H, J=7.5 Hz), 7.45-7.39 (m, 3H), 7.28 (t, 1H, J=8.0 Hz), 7.18-7.14 (m, 4H), 7.09 (t, 1H, J=8.0 Hz), 6.33 (dd, 2H, J=1.5 Hz, 17.5 Hz), 6.18 (dd, 2H, J=10.5 Hz, 17.5 Hz), 5.944 (dd, 1H, J=1.5 Hz, 10.5 Hz), 5.941 (dd, 1H, J=1.5 Hz, 10.5 Hz), 4.14-4.10 (m, 8H), 1.80-1.75 (m, 4H), 1.69-1.63 (m, 4H), 1.53-1.38 (m, 8H).

LCMS (APCI): calcd for $C_{46}H_{47}N_3O_{10}S$: 833 [M$^+$]; Found: 833.

Example 2

Synthesis of Compound 2

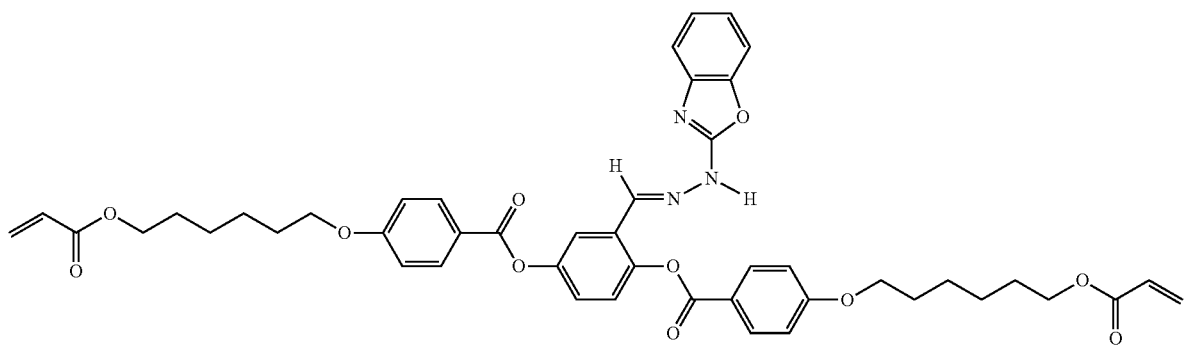

Compound 2

Step 1: Synthesis of Intermediate B

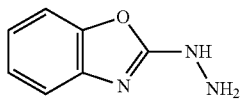

Intermediate B

A four-necked reactor equipped with a thermometer was charged with 4.9 g (97.9 mmol) of hydrazine monohydrate and 20 ml of ethanol under a nitrogen stream to prepare a homogeneous solution. The solution was heated to 50° C. After the addition of 3.0 g (19.54 mmol) of 2-chlorobenzoxazole dissolved in ethanol, the mixture was stirred at 50° C. for 1 hour. After completion of the reaction, the reaction mixture was added to 500 ml of 10% sodium bicarbonate water, and extracted with 200 ml of chloroform. The chloroform layer was washed with 500 ml of 10% sodium bicarbonate water, and dried over anhydrous sodium sulfate, and sodium sulfate was filtered off. Chloroform was evaporated from the filtrate under reduced pressure using a rotary evaporator to obtain 1.8 g of an intermediate B as a white solid. The intermediate B was used directly for the subsequent reaction without purification.

Step 2: Synthesis of Compound 2

A four-necked reactor equipped with a thermometer was charged with 15 g (21.8 mmol) of the intermediate A synthesized by the step 1 in the section "Synthesis of compound 1", 4.89 g (32.8 mmol) of the intermediate B synthesized by the step 1, and 100 ml of THF under a nitrogen stream to prepare a homogeneous solution. After the addition of 25.4 mg (0.11 mmol) of (±)-10-camphorsulfonic acid to the solution, the mixture was stirred at 25° C. for 3 hours. After completion of the reaction, the reaction mixture was added to 800 ml of 10% sodium bicarbonate water, and extracted twice with 150 ml of ethyl acetate. The ethyl acetate layer was collected, and dried over anhydrous sodium sulfate, and sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=8:2 (volume ratio)) to obtain 9.2 g of a compound 2 as a white solid (yield: 51.6%).

The structure of the target product was identified by $^1$H-NMR and mass spectroscopy.

$^1$H-NMR (500 MHz, DMSO-$d_6$, TMS, δ ppm): 12.20 (br, 1H), 8.28 (s, 1H), 8.17-8.12 (m, 4H), 7.82 (br, 1H), 7.46-7.40 (m, 3H), 7.32 (br, 1H), 7.20-7.14 (m, 5H), 7.08 (t, 1H, J=8.0 Hz), 6.33 (dd, 2H, J=1.5 Hz, 17.5 Hz), 6.18 (dd, 2H, J=10.5 Hz, 17.5 Hz), 5.94 (d, 2H, J=10.5 Hz), 4.14-4.10 (m, 8H), 1.80-1.75 (m, 4H), 1.69-1.63 (m, 4H), 1.51-1.38 (m, 8H).

LCMS (APCI): calcd for $C_{46}H_{47}N_3O_{11}$: 817 [M$^+$]; Found: 817.

Example 3

Synthesis of Compound 3

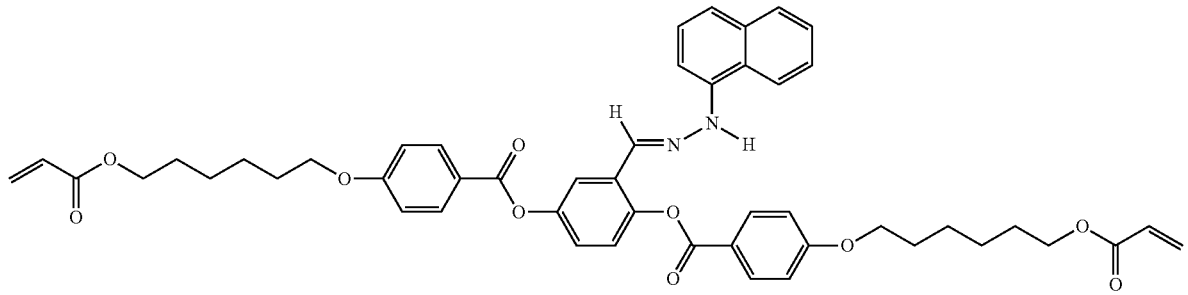

Compound 3

A four-necked reactor equipped with a thermometer was charged with 2.00 g (2.91 mmol) of the intermediate A synthesized by the step 1 in the section "Synthesis of compound 1", 850 mg (4.37 mmol) of 1-naphthylhydrazine hydrochloride, 30 ml of THF, and 10 ml of ethanol under a nitrogen stream to prepare a homogeneous solution. The solution was heated to 50° C., and reacted at 50° C. for 1 hour with stirring. After completion of the reaction, the solvent was evaporated from the reaction mixture under reduced pressure using a rotary evaporator to obtain a reddish brown solid. The reddish brown solid was purified by silica gel column chromatography (n-hexane:ethyl acetate=85:15 (volume ratio)) to obtain 1.04 g of a compound 3 as an orange solid (yield: 43.0%).

The structure of the target product was identified by $^1$H-NMR and mass spectroscopy.

$^1$H-NMR (400 MHz, CDCl$_3$, TMS, δ ppm): 8.35 (s, 1H), 8.20 (d, 2H, J=7.0 Hz), 8.18 (d, 2H, J=7.0 Hz), 7.95-7.96 (m, 2H), 7.79 (t, 2H, J=7.3 Hz), 7.32-7.53 (m, 5H), 7.17-7.24 (m, 2H), 7.00 (d, 2H, J=7.0 Hz), 7.98 (d, 2H, J=7.0 Hz), 6.41 (dd, 2H, J=0.9 Hz, 17.4 Hz), 6.13 (dd, 2H, J=10.5 Hz, 17.4 Hz), 5.82 (dd, 2H, J=0.9 Hz, 10.5 Hz), 4.19 (t, 4H, J=6.6 Hz), 4.05-4.08 (m, 4H), 1.79-1.89 (m, 4H), 1.65-1.77 (m, 4H), 1.46-1.59 (m, 8H).

LCMS (APCI): calcd for $C_{49}H_{50}N_2O_{10}$: 826 [M$^+$]; Found: 826.

Example 4

Synthesis of Compound 4

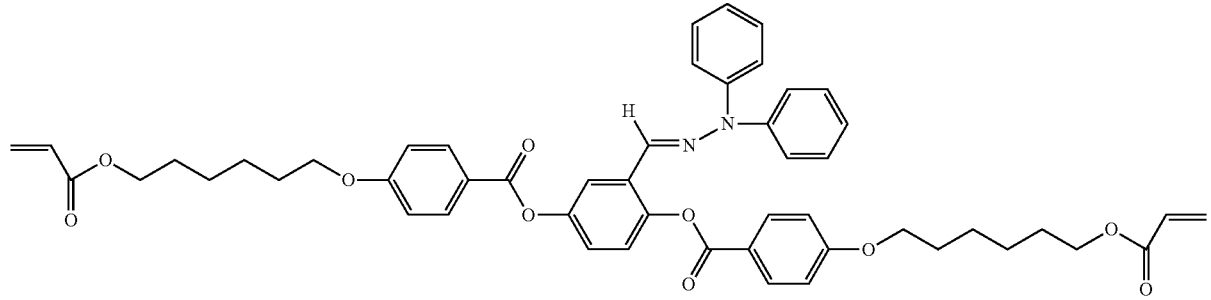

Compound 4

A four-necked reactor equipped with a thermometer was charged with 1.50 g (2.18 mmol) of the intermediate A synthesized by the step 1 in the section "Synthesis of compound 1", 578 mg (2.62 mmol) of 1,1-diphenylhydrazine, 5 ml of THF, and 10 ml of ethanol under a nitrogen stream to prepare a homogeneous solution. The solution was reacted at 50° C. for 3.5 hours. After completion of the reaction, the reaction mixture was added to 50 ml of water, and extracted with 100 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=75:25 (volume ratio)) to obtain 1.43 g of a compound 4 as a light yellow solid (yield: 76.9%).

The structure of the target product was identified by $^1$H-NMR.

$^1$H-NMR (400 MHz, CDCl$_3$, TMS, δ ppm): 8.18 (d, 2H, J=8.7 Hz), 7.90 (d, 1H, J=2.7 Hz), 7.82 (d, 2H, J=8.7 Hz), 7.21-7.29 (m, 6H), 7.10-7.15 (m, 5H), 7.05 (t, 2H, J=7.3 Hz), 6.99 (d, 2H, J=9.2 Hz), 6.88 (d, 2H, J=9.2 Hz), 6.41 (dd, 2H, J=1.8 Hz, 17.4 Hz), 6.13 (dd, 2H, J=10.5 Hz, 17.4 Hz), 5.82 (dd, 2H, J=1.8 Hz, 10.5 Hz), 4.20 (t, 2H, J=6.4 Hz), 4.19 (t, 2H, J=6.4 Hz), 4.07 (t, 2H, J=6.4 Hz), 4.06 (t, 2H, J=6.4 Hz), 1.82-1.92 (m, 4H), 1.70-1.79 (m, 4H), 1.44-1.61 (m, 8H).

Example 5

Synthesis of Compound 5

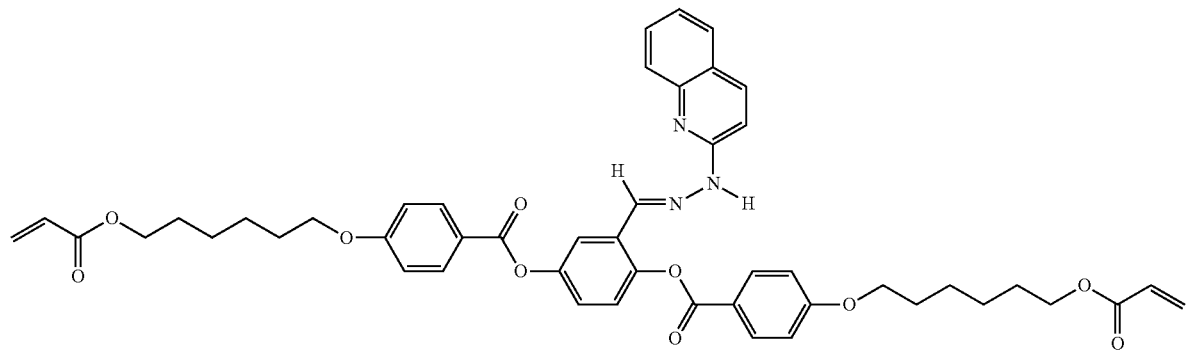

Compound 5

A four-necked reactor equipped with a thermometer was charged with 1.50 g (2.18 mmol) of the intermediate A synthesized by the step 1 in the section "Synthesis of compound 1", 417 mg (2.62 mmol) of 2-hydrazinoquinoline, 5 ml of THF, and 10 ml of ethanol under a nitrogen stream. The mixture was stirred at 50° C. for 2.5 hours. After completion of the reaction, the solvent was evaporated from the reaction mixture under reduced pressure using a rotary evaporator to obtain an orange solid. The orange solid was purified by silica gel column chromatography (chloroform:ethyl acetate=9:1 (volume ratio)) to obtain 1.31 g of a compound 5 as a yellow solid (yield: 72.6%).

The structure of the target product was identified by $^1$H-NMR.

$^1$H-NMR (500 MHz, DMSO-$d_6$, TMS, δ ppm): 11.5 (s, 1H), 8.23 (s, 1H), 8.16 (d, 2H, J=9.0 Hz), 8.13 (d, 2H, J=9.0 Hz), 8.05 (d, 1H, J=9.0 Hz), 7.91 (d, 1H, J=2.5 Hz), 7.75 (d, 1H, J=8.0 Hz), 7.53-7.59 (m, 3H), 7.40 (d, 1H, J=9.0 Hz), 7.33 (ddd, 1H, J=2.0 Hz, 6.0 Hz, 8.0 Hz), 7.40 (d, 1H, J=9.0 Hz), 7.17 (d, 2H, J=9.0 Hz), 7.14 (d, 2H, J=9.0 Hz), 6.33 (dd, 2H, J=1.0 Hz, 17.3 Hz), 6.19 (dd, 2H, J=10.5 Hz, 17.3 Hz), 5.94 (dd, 2H, J=1.0 Hz, 10.5 Hz), 4.09-4.14 (m, 8H), 1.75-1.81 (m, 4H), 1.63-1.69 (m, 4H), 1.38-1.51 (m, 8H).

Example 6

Synthesis of Compound 6

Step 1: Synthesis of Intermediate C

Intermediate C

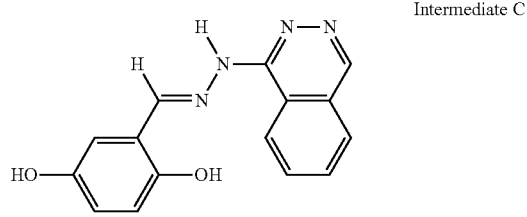 [SMILES: Oc1ccc(O)c(/C=N/Nc2nncc3ccccc23)c1]

A four-necked reactor equipped with a thermometer was charged with 394 mg (2.85 mmol) of 2,5-dihydroxybenzaldehyde, 562 mg (2.86 mmol) of 1-hydrazinophthalazine hydrochloride, 65 mg (0.28 mmol) of (±)-10-camphorsulfonic acid, and 20 ml of ethanol under a nitrogen stream. The mixture was stirred at 25° C. for 3 hours. After completion of the reaction, a solid that had precipitated was filtered off. The solid was washed with ethanol, and dried using a vacuum dryer to obtain 610 mg of an intermediate C as a yellow solid (yield: 76.4%).

The structure of the target product was identified by $^1$H-NMR.

$^1$H-NMR (500 MHz, DMSO-$d_6$, TMS, δ ppm): 14.486 (br, 1H), 14.150 (br, 1H), 9.77 (s, 1H), 9.30 (s, 1H), 9.20 (d, 1H, J=8.0 Hz), 9.06 (s, 1H), 8.27-8.14 (m, 3H), 7.76 (d, 1H, J=2.5 Hz), 6.89 (dd, 1H, J=3.0 Hz, 8.5 Hz), 6.84 (d, 1H, J=8.5 Hz).

Step 2: Synthesis of Compound 6

A four-necked reactor equipped with a thermometer was charged with 600 mg (2.14 mmol) of the intermediate C, 1.56 g (5.35 mmol) of 4-(6-acryloylhex-1-yloxy)benzoic acid (manufactured by DKSH Japan K.K.), 39 mg (0.32 mmol) of 4-(dimethylamino)pyridine, and 40 ml of N-methylpyrrolidone under a nitrogen stream to prepare a homogeneous solution. After the addition of 1.23 g (6.42 mmol) of WSC to the solution, the mixture was stirred at 25° C. for 15 hours. After completion of the reaction, the reaction mixture was added to 500 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=9:1 (volume ratio)) to obtain 1.08 g of a polymerizable compound 6 as a yellow solid (yield: 60.9%).

The structure of the target product was identified by $^1$H-NMR.

$^1$H-NMR (500 MHz, CDCl$_3$, TMS, δ ppm): 10.56 (s, 1H), 8.65 (s, 1H), 8.34 (d, 1H, J=7.5 Hz), 8.21 (d, 2H, J=9.0 Hz), 8.19 (d, 2H, J=9.0 Hz), 8.01 (d, 1H, J=2.5 Hz), 7.85 (s, 1H), 7.66 (dd, 1H, J=7.5 Hz, 7.5 Hz), 7.62 (dd, 1H, J=7.5 Hz, 7.5 Hz), 7.51 (d, 1H, J=7.5 Hz), 7.32 (dd, 1H, J=2.5 Hz, 8.5 Hz), 7.28 (d, 1H, J=8.5 Hz), 7.00 (d, 2H, J=9.0 Hz), 6.99 (d, 2H, J=9.0 Hz), 6.41 (dd, 2H, J=1.5 Hz, 17.5 Hz), 6.13 (dd, 2H, J=10.5 Hz, 17.5 Hz), 5.83 (dd, 2H, J=1.5 Hz, 10.5 Hz), 4.20 (t, 2H, J=6.5 Hz), 4.19 (t, 2H, J=7.0 Hz), 4.08 (t, 2H, J=6.5 Hz), 4.07 (t, 2H, J=6.5 Hz), 1.83-1.89 (m, 4H), 1.71-1.77 (m, 4H), 1.45-1.59 (m, 8H).

Compound 6

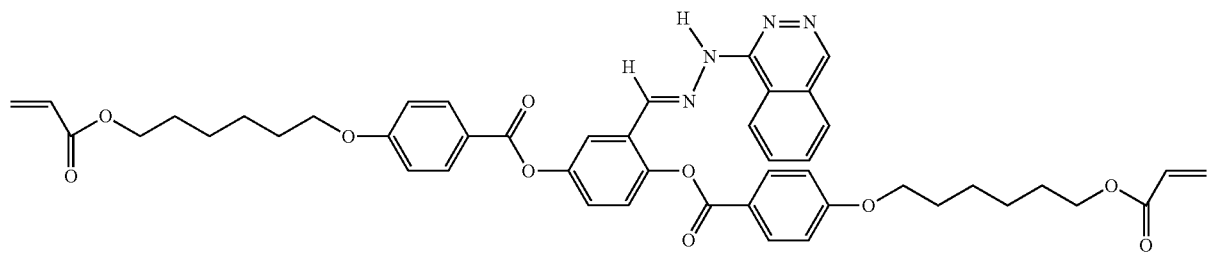

Example 7

Synthesis of Compound 7

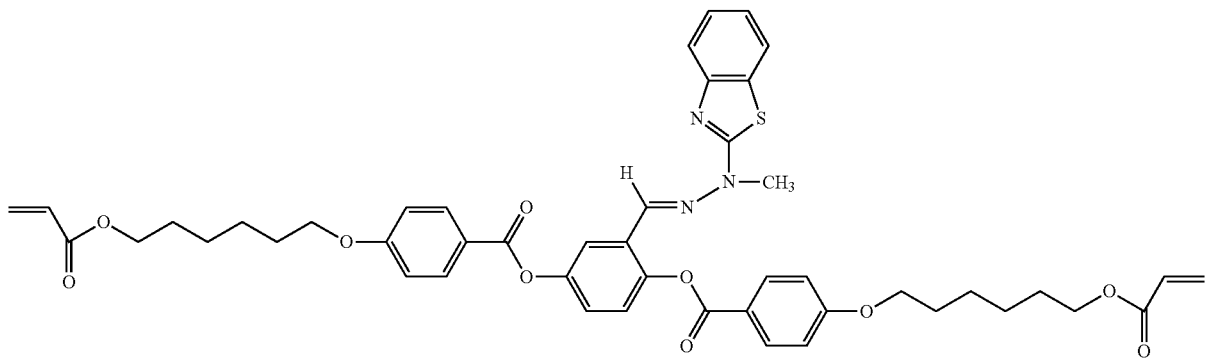

Compound 7

Step 1: Synthesis of Intermediate D

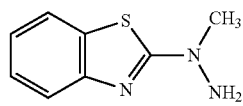

Intermediate D

A four-necked reactor equipped with a thermometer was charged with 1.00 g (6.05 mmol) of 2-hydrazinobenzothiazole and 15 ml of THF under a nitrogen stream to prepare a homogeneous solution. 4.5 ml (7.26 mmol) of lithium hexamethyldisilazane (26% THF solution) was slowly added dropwise to the solution. The mixture was stirred at 0° C. for 30 minutes. After the addition of 0.46 ml (7.26 mmol) of methyl iodide, the mixture was stirred at 25° C. for 3 hours. After completion of the reaction, the reaction mixture was added to 100 ml of water, and extracted with 100 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=70:30 (volume ratio)) to obtain 693 mg of an intermediate D as a light yellow solid (yield: 63.9%).

The structure of the target product was identified by $^1$H-NMR.

$^1$H-NMR (500 MHz, CDCl$_3$, TMS, δ ppm): 7.61 (dd, 1H, J=1.0 Hz, 8.0 Hz), 7.55 (dd, 1H, J=1.0 Hz, 7.5 Hz), 7.29 (ddd, 1H, J=1.0 Hz, 7.5 Hz, 8.0 Hz), 7.08 (ddd, 1H, J=1.0 Hz, 7.5 Hz, 7.5 Hz), 4.31 (s, 2H), 3.45 (s, 3H).

Step 2: Synthesis of Intermediate E

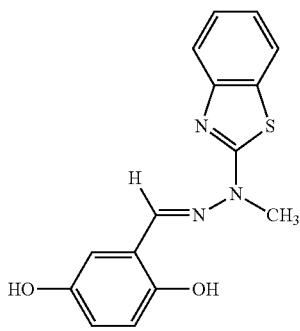

Intermediate E

A four-necked reactor equipped with a thermometer was charged with 380 mg (2.75 mmol) of 2,5-dihydroxybenzaldehyde, 493 mg (2.75 mmol) of the intermediate D, and 10 ml of 1-propanol under a nitrogen stream. The mixture was stirred at 80° C. for 1 hour. After completion of the reaction, the reaction mixture was cooled to 20° C., and a solid that had precipitated was filtered off. The solid was washed with 1-propanol, and dried using a vacuum dryer to obtain 599 mg of an intermediate E as a light yellow solid (yield: 72.7%).

The structure of the target product was identified by $^1$H-NMR.

$^1$H-NMR (400 MHz, DMSO-d$_6$, TMS, δ ppm): 9.42 (s, 1H), 8.97 (s, 1H), 8.08 (s, 1H), 7.84 (dd, 1H, J=1.0 Hz, 8.0 Hz), 7.60 (dd, 1H, J=1.0 Hz, 8.0 Hz), 7.38 (ddd, 1H, J=1.0 Hz, 7.5 Hz, 8.0 Hz), 7.19 (d, 1H, J=3.0 Hz), 7.16 (ddd, 1H, J=1.0 Hz, 7.5 Hz, 8.0 Hz), 6.77 (d, 1H, J=9.0 Hz), 6.70 (dd, 1H, J=9.0 Hz), 3.70 (s, 3H).

Step 3: Synthesis of Compound 7

A four-necked reactor equipped with a thermometer was charged with 500 mg (1.67 mmol) of the intermediate E, 1.22 g (4.18 mmol) of 4-(6-acryloylhex-1-yloxy)benzoic acid (manufactured by DKSH Japan K.K.), 102 mg (835 μmol) of 4-(dimethylamino)pyridine, and 20 ml of N-methylpyrrolidone under a nitrogen stream to prepare a homogeneous solution. After the addition of 960 mg (5.01 mmol) of WSC to the solution, the mixture was stirred at 25° C. for 15 hours. After completion of the reaction, the reaction mixture was added to 300 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=9:1 (volume ratio)) to obtain 1.03 g of a compound 7 as a light yellow solid (yield: 72.4%).

The structure of the target product was identified by $^1$H-NMR.

$^1$H-NMR (500 MHz, CDCl$_3$, TMS, δ ppm): 8.201 (d, 2H, J=9.0 Hz), 8.196 (d, 2H, J=9.0 Hz), 7.91 (s, 1H), 7.73 (s, 1H), 7.61-7.64 (m, 2H), 7.32 (ddd, 1H, J=1.0 Hz, 7.5 Hz, 7.5 Hz), 7.23-7.28 (m, 1H), 7.11-7.18 (m, 2H), 7.02 (d, 2H, J=9.0 Hz), 7.01 (d, 2H, J=9.0 Hz), 6.41 (dd, 2H, J=1.5 Hz, 17.5 Hz), 6.14 (dd, 2H, J=10.5 Hz, 17.5 Hz), 5.83 (dd, 2H, J=1.5 Hz, 10.5 Hz), 4.194 (t, 2H, J=6.5 Hz), 4.192 (t, 2H, J=6.5 Hz), 4.08 (t, 4H, J=6.5 Hz), 3.63 (s, 3H), 1.84-1.89 (m, 4H), 1.71-1.77 (m, 4H), 1.46-1.59 (m, 8H).

Example 8

Synthesis of Compound 8

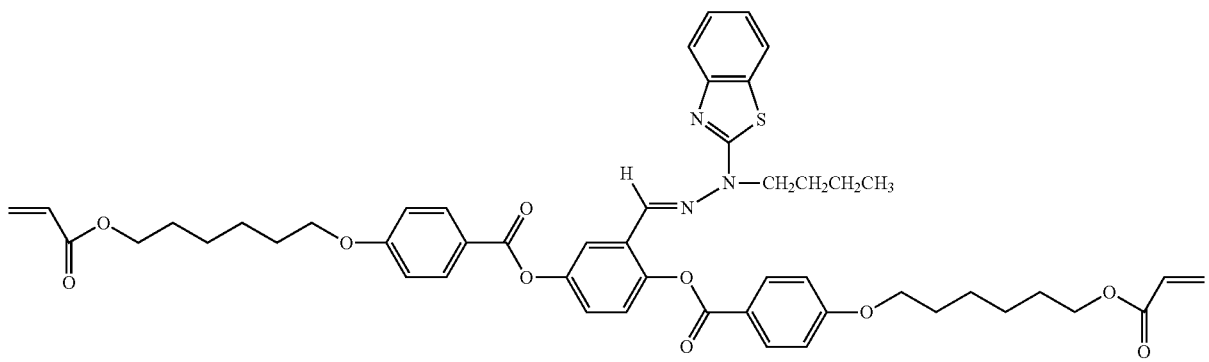

Compound 8

Step 1: Synthesis of Intermediate F

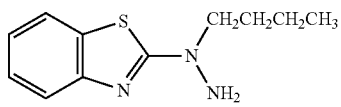

Intermediate F

A four-necked reactor equipped with a thermometer was charged with 2.00 g (12.1 mmol) of 2-hydrazinobenzothiazole and 20 ml of N,N-dimethylformamide (DMF) under a nitrogen stream to prepare a homogeneous solution. After the addition of 8.36 g (60.5 mmol) of potassium carbonate and 2.67 g (14.5 mmol) of 1-iodobutane to the solution, the mixture was stirred at 50° C. for 7 hours. After completion of the reaction, the reaction mixture was cooled to 20° C., added to 200 ml of water, and extracted with 300 ml of ethyl acetate. After drying the ethyl acetate layer over anhydrous sodium sulfate, sodium sulfate was filtered off Ethyl acetate was evaporated from the filtrate under reduced pressure using a rotary evaporator to obtain a yellow solid. The yellow solid was purified by silica gel column chromatography (n-hexane:ethyl acetate=75:25 (volume ratio)) to obtain 2.34 g of an intermediate F as a white solid (yield: 87.4%).

The structure of the target product was identified by $^1$H-NMR.

$^1$H-NMR (400 MHz, CDCl$_3$, TMS, δ ppm): 7.59 (d, 1H, J=7.8 Hz), 7.52 (d, 1H, J=7.8 Hz), 7.27 (dd, 1H, J=7.3 Hz, 7.8 Hz), 7.05 (dd, 1H, J=7.3 Hz, 7.8 Hz), 4.21 (s, 2H), 3.75 (t, 2H, J=7.3 Hz), 1.68-1.75 (m, 2H), 1.37-1.46 (m, 2H), 0.97 (t, 3H, J=7.3 Hz).

Step 2: Synthesis of Intermediate G

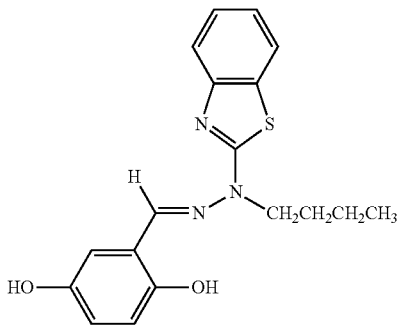

Intermediate G

A four-necked reactor equipped with a thermometer was charged with 763 mg (5.52 mmol) of 2,5-dihydroxybenzaldehyde and 1.34 g (6.07 mmol) of the intermediate F under a nitrogen stream. The mixture was stirred at 80° C. for 1.5 hours. After completion of the reaction, the reaction mixture was cooled to 20° C., and a solid that had precipitated was filtered off. The solid was washed with 1-propanol, and dried using a vacuum dryer to obtain 1.76 g of an intermediate G as a light yellow solid (yield: 84.9%).

The structure of the target product was identified by $^1$H-NMR.

$^1$H-NMR (500 MHz, DMSO-d$_6$, TMS, δ ppm): 9.39 (s, 1H), 8.97 (s, 1H), 8.15 (s, 1H), 7.83 (d, 1H, J=7.5 Hz), 7.60 (d, 1H, J=7.5 Hz), 7.33 (dd, 1H, J=7.5 Hz, 7.5 Hz), 7.18 (d, 1H, J=3.0 Hz), 7.16 (dd, 1H, J=7.5 Hz, 7.5 Hz), 6.76 (d, 1H, J=8.5 Hz), 6.70 (dd, 1H, J=3.0 Hz, 8.5 Hz), 4.33 (t, 2H, J=7.5 Hz), 1.66 (tt, 2H, J=7.5 Hz, 7.5 Hz), 1.39 (tq, 2H, J=7.5 Hz, 7.0 Hz), 0.95 (t, 3H, J=7.0 Hz).

Step 3: Synthesis of Compound 8

A four-necked reactor equipped with a thermometer was charged with 1.00 g (2.93 mmol) of the intermediate G, 2.14 g (7.32 mmol) of 4-(6-acryloylhex-1-yloxy)benzoic acid (manufactured by DKSH Japan K.K.), 179 mg (1.47 mmol) of 4-(dimethylamino)pyridine, and 30 ml of N-methylpyrrolidone under a nitrogen stream to prepare a homogeneous solution. After the addition of 1.69 g (8.79 mmol) of WSC to the solution, the mixture was stirred at 25° C. for 18 hours. After completion of the reaction, the reaction mixture was added to 500 ml of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=9:1 (volume ratio)) to obtain 2.11 g of a compound 8 as a white solid (yield: 80.9%).

The structure of the target product was identified by $^1$H-NMR.

$^1$H-NMR (500 MHz, CDCl$_3$, TMS, δ ppm): 8.20 (d, 2H, J=8.5 Hz), 8.19 (d, 2H, J=8.5 Hz), 7.90 (d, 1H, J=2.0 Hz), 7.76 (s, 1H), 7.61-7.64 (m, 2H), 7.25-7.32 (m, 3H), 7.12 (dd, 1H, J=7.5 Hz, 7.5 Hz), 7.01 (d, 4H, J=8.5 Hz), 6.41 (dd, 2H, J=1.5 Hz, 17.0 Hz), 6.14 (dd, 2H, J=10.5 Hz, 17.0 Hz), 5.83 (dd, 2H, J=1.5 Hz, 10.5 Hz), 4.17-4.21 (m, 6H), 4.08 (t, 2H, J=6.5 Hz), 4.07 (t, 2H, J=6.5 Hz), 1.84-1.91 (m, 4H), 1.71-1.77 (m, 4H), 1.46-1.61 (m, 10H), 1.19-1.28 (m, 2H), 0.77 (t, 3H, J=7.5 Hz).

Example 9

Synthesis of Compound 9

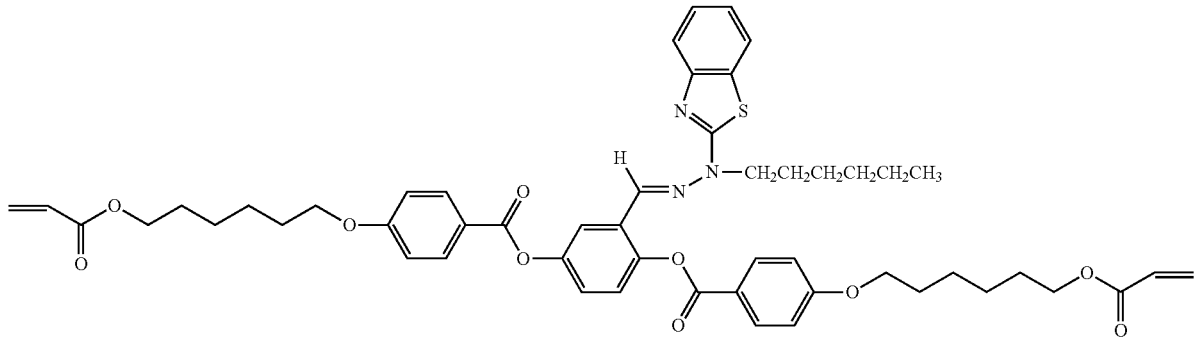

Compound 9

Step 1: Synthesis of Intermediate H

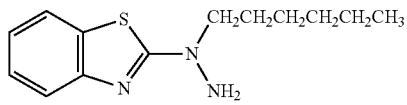

Intermediate H

A four-necked reactor equipped with a thermometer was charged with 2.00 g (12.1 mmol) of 2-hydrazinobenzothiazole and 20 ml of DMF under a nitrogen stream to prepare a homogeneous solution. After the addition of 8.36 g (60.5 mmol) of potassium carbonate and 3.08 g (14.5 mmol) of 1-iodohexane, the mixture was stirred at 50° C. for 7 hours. After completion of the reaction, the reaction mixture was cooled to 20° C., added to 200 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=75:25 (volume ratio)) to obtain 2.10 g of an intermediate H as a white solid (yield: 69.6%).

The structure of the target product was identified by $^1$H-NMR.

$^1$H-NMR (500 MHz, CDCl$_3$, TMS, δ ppm): 7.60 (dd, 1H, J=1.0 Hz, 8.0 Hz), 7.53 (dd, 1H, J=1.0 Hz, 8.0 Hz), 7.27 (ddd, 1H, J=1.0 Hz, 8.0 Hz, 8.0 Hz), 7.06 (ddd, 1H, J=1.0 Hz, 8.0 Hz, 8.0 Hz), 4.22 (s, 2H), 3.74 (t, 2H, J=7.5 Hz), 1.69-1.76 (m, 2H), 1.29-1.42 (m, 6H), 0.89 (t, 3H, J=7.0 Hz).

Step 2: Synthesis of Intermediate I

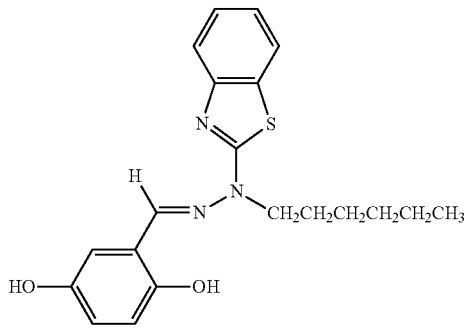

Intermediate I

A four-necked reactor equipped with a thermometer was charged with 504 mg (3.65 mmol) of 2,5-dihydroxybenzaldehyde, 1.00 g (4.01 mmol) of the intermediate H, and 10 ml of 1-propanol under a nitrogen stream. The mixture was stirred at 80° C. for 3 hours. After completion of the reaction, the reaction mixture was cooled to 20° C., and a solid that had precipitated was filtered off. The solid was washed with 1-propanol, and dried using a vacuum dryer to obtain 1.20 g of an intermediate I as a light yellow solid (yield: 88.8%).

The structure of the target product was identified by $^1$H-NMR.

$^1$H-NMR (500 MHz, DMSO-d$_6$, TMS, δ ppm): 9.39 (s, 1H), 8.97 (s, 1H), 8.15 (s, 1H), 7.83 (dd, 1H, J=1.0 Hz, 8.0 Hz), 7.60 (dd, 1H, J=1.0 Hz, 8.0 Hz), 7.33 (ddd, 1H, J=1.0 Hz, 7.5 Hz, 8.0 Hz), 7.18 (d, 1H, J=3.0 Hz), 7.16 (ddd, 1H, J=1.0 Hz, 7.5 Hz, 8.0 Hz), 6.76 (d, 1H, J=8.5 Hz), 6.70 (dd, 1H, J=3.0 Hz, 8.5 Hz), 4.32 (t, 2H, J=7.0 Hz), 1.64-1.70 (m, 2H), 1.25-1.39 (m, 6H), 0.86 (t, 3H, J=7.5 Hz).

Step 3: Synthesis of Compound 9

A four-necked reactor equipped with a thermometer was charged with 1.20 g (3.24 mmol) of the intermediate I, 2.37 g (8.10 mmol) of 4-(6-acryloylhex-1-yloxy)benzoic acid (manufactured by DKSH Japan K.K.), 198 mg (1.62 mmol) of 4-(dimethylamino)pyridine, and 20 ml of N-methylpyrrolidone under a nitrogen stream to prepare a homogeneous solution. After the addition of 1.86 g (9.72 mmol) of WSC to the solution, the mixture was stirred at 25° C. for 15 hours. After completion of the reaction, the reaction mixture was added to 300 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=9:1 (volume ratio)) to obtain 1.13 g of a compound 9 as a light yellow solid (yield: 37.9%).

The structure of the target product was identified by $^1$H-NMR.

$^1$H-NMR (500 MHz, CDCl$_3$, TMS, δ ppm): 8.20 (d, 2H, J=9.0 Hz), 8.19 (d, 2H, J=9.0 Hz), 7.90 (d, 1H, J=2.0 Hz), 7.76 (s, 1H), 7.63 (dd, 1H, J=1.0 Hz, 8.0 Hz), 7.62 (dd, 1H, J=1.0 Hz, 8.0 Hz), 7.25-7.34 (m, 3H), 7.12 (ddd, 1H, J=1.0 Hz, 7.5 Hz, 8.0 Hz), 7.01 (d, 2H, J=9.0 Hz), 7.00 (d, 2H, J=9.0 Hz), 6.42 (dd, 2H, J=1.5 Hz, 17.5 Hz), 6.14 (dd, 2H, J=10.0 Hz, 17.5 Hz), 5.83 (dd, 2H, J=1.5 Hz, 10.0 Hz), 6.16-4.21 (m, 6H), 4.08 (t, 2H, J=6.5 Hz), 4.06 (t, 2H, J=6.5 Hz), 1.84-1.89 (m, 4H), 1.71-1.77 (m, 4H), 1.46-1.63 (m, 10H), 1.07-1.21 (m, 6H), 0.79 (t, 3H, J=6.5 Hz).

Example 10

Synthesis of Compound 10

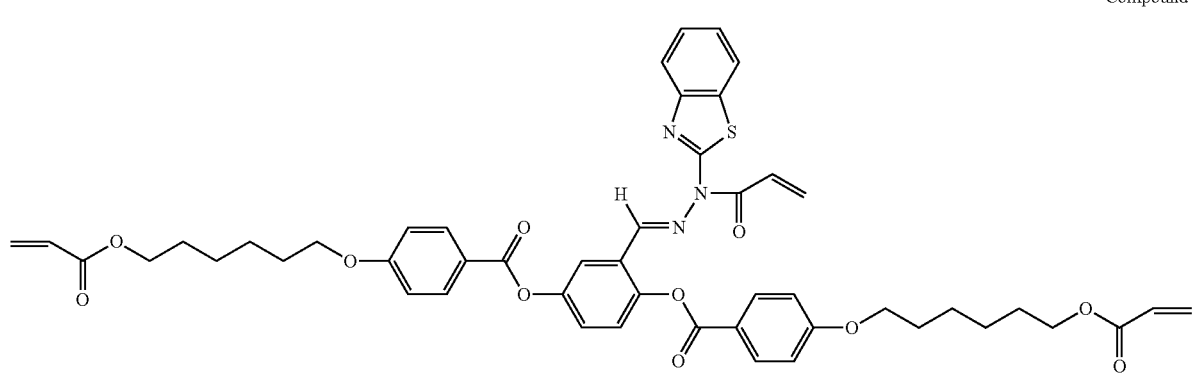

Compound 10

A four-necked reactor equipped with a thermometer was charged with 5.0 g (5.98 mmol) of the polymerizable compound 1 synthesized in Example 1 and 100 ml of THF under a nitrogen stream to prepare a homogeneous solution. After the addition of 10.0 ml (71.7 mmol) of triethylamine and 812 mg (8.97 mmol) of acryloyl chloride to the solution, the mixture was stirred at 25° C. for 2 hours. After completion of the reaction, the reaction mixture was added to 200 ml of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=9:1 (volume ratio)) to obtain 1.21 g of a polymerizable compound 10 as a light yellow solid (yield: 22.8%).

The structure of the target product was identified by $^1$H-NMR.

$^1$H-NMR (500 MHz, CDCl$_3$, TMS, δ ppm): 9.64 (s, 1H), 8.18 (d, 2H, J=9.0 Hz), 8.06 (d, 2H, J=9.0 Hz), 7.95 (s, 1H), 7.77-7.81 (m, 1H), 7.44 (dd, 1H, J=10.5, 17.0 Hz), 7.36-7.39 (m, 3H), 7.32 (ddd, 1H, J=1.5 Hz, 7.0 Hz, 7.5 Hz), 7.29 (ddd, 1H, J=1.5 Hz, 7.0 Hz, 7.0 Hz), 6.99 (d, 2H, J=9.0 Hz), 6.84 (d, 2H, J=9.0 Hz), 6.64 (dd, 1H, J=1.5 Hz, 17.0 Hz), 6.41 (dd, 2H, J=1.5 Hz, 17.5 Hz), 6.13 (dd, 2H, J=10.0 Hz, 17.5 Hz), 5.95 (dd, 1H, J=1.5 Hz, 10.5 Hz), 5.82 (dd, 2H, J=1.5 Hz, 10.0 Hz), 4.20 (t, 2H, J=6.5 Hz), 4.19 (t, 2H, J=6.5 Hz), 4.06 (t, 2H, J=6.5 Hz), 4.01 (t, 2H, J=6.5 Hz), 1.83-1.88 (m, 4H), 1.70-1.77 (m, 4H), 1.44-1.59 (m, 8H).

Example 11

Synthesis of Compound 11

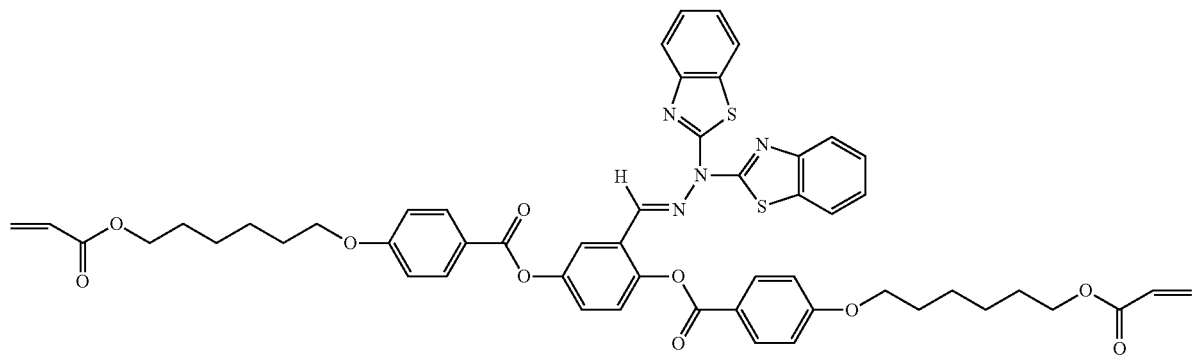

Compound 11

Step 1: Synthesis of Intermediate J

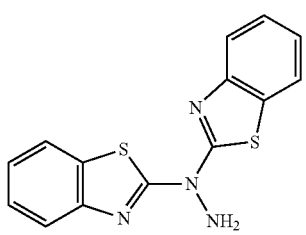

Intermediate J

A four-necked reactor equipped with a thermometer was charged with 2.00 g (12.1 mmol) of 2-hydrazinobenzothiazole and 30 ml of THF under a nitrogen stream to prepare a homogeneous solution. 9.0 ml (14.52 mmol) of lithium hexamethyldisilazane (26% THF solution) was slowly added dropwise to the solution at 0° C. The mixture was stirred at 0° C. for 30 minutes. After the addition of 2.46 g (14.52 mmol) of 2-chlorobenzothiazole, the mixture was stirred at 25° C. for 3 hours. After completion of the reaction, the reaction mixture was added to 200 ml of water, and extracted with 200 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=75:25 (volume ratio)) to obtain 1.02 mg of an intermediate J as a light yellow solid (yield: 28.3%).

The structure of the target product was identified by $^1$H-NMR.

$^1$H-NMR (400 MHz, DMSO-$d_6$, TMS, δ ppm): 7.97 (d, 2H, J=7.5 Hz), 7.74 (d, 2H, J=8.0 Hz), 7.42 (dd, 2H, J=7.8 Hz, 8.0 Hz), 7.27 (dd, 2H, J=7.5 Hz, 7.8 Hz), 6.55 (s, 2H).

Step 2: Synthesis of Intermediate K

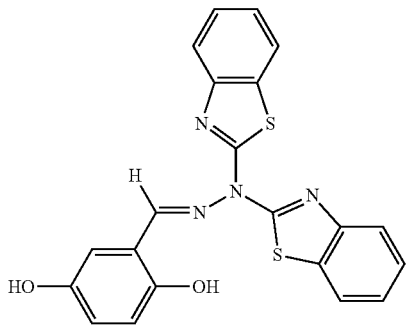

Intermediate K

A four-necked reactor equipped with a thermometer was charged with 394 mg (2.86 mmol) of 2,5-dihydroxybenzaldehyde, 1.02 mg (3.42 mmol) of the intermediate J, 65 mg (0.28 mmol) of (±)-10-camphorsulfonic acid, and 20 ml of 1-propanol under a nitrogen stream. The mixture was stirred at 80° C. for 2.5 hours. After completion of the reaction, the reaction mixture was cooled to 20° C., and a solid that had precipitated was filtered off. The solid was washed with 1-propanol, and dried using a vacuum dryer to obtain 802 mg of an intermediate K as a light yellow solid (yield: 66.9%).

The structure of the target product was identified by $^1$H-NMR.

$^1$H-NMR (500 MHz, THF-$d_8$, TMS, δ ppm): 8.39 (s, 1H), 7.40 (s, 1H), 6.31 (s, 1H), 6.19 (dd, 2H, J=1.0 Hz, 8.0 Hz), 6.12 (dd, 2H, J=1.0 Hz, 8.0 Hz), 5.71 (ddd, 2H, J=1.0 Hz, 7.5 Hz, 8.0 Hz), 5.59 (ddd, 2H, J=1.0 Hz, 7.5 Hz, 8.0 Hz), 5.47 (d, 1H, J=3.0 Hz), 5.12 (dd, 1H, J=3.0 Hz, 9.0 Hz), 5.08 (d, 1H, J=9.0 Hz).

Step 3: Synthesis of Compound 11

A four-necked reactor equipped with a thermometer was charged with 800 mg (1.91 mmol) of the intermediate K, 1.4 g (4.78 mmol) of 4-(6-acryloylhex-1-yloxy)benzoic acid (manufactured by DKSH Japan K.K.), 117 mg (14.3 mmol) of 4-(dimethylamino)pyridine, and 30 ml of N-methylpyrrolidone under a nitrogen stream to prepare a homogeneous solution. After the addition of 1.1 g (5.74 mmol) of WSC to the solution, the mixture was stirred at 25° C. for 18 hours. After completion of the reaction, the reaction mixture was added to 600 ml of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=9:1 (volume ratio)) to obtain 12.8 g of a compound 11 as a white solid (yield: 68.8%).

The structure of the target product was identified by $^1$H-NMR.

$^1$H-NMR (400 MHz, THF-$d_8$, TMS, δ ppm): 10.84 (s, 1H), 8.24 (d, 2H, J=9.2 Hz), 8.17 (d, 2H, J=8.7 Hz), 8.06 (s, 1H), 7.85 (d, 2H, J=7.9 Hz), 7.44 (s, 2H), 7.39 (d, 2H, J=8.2 Hz), 7.23-7.31 (m, 4H), 7.07 (d, 2H, J=9.2 Hz), 7.06 (d, 2H, J=8.7 Hz), 6.32 (d, 2H, J=17.4 Hz), 6.10 (dd, 2H, J=10.1 Hz, 17.4 Hz), 5.77 (d, 2H, J=10.1 Hz), 4.08-4.16 (m, 8H), 1.80-1.90 (m, 4H), 1.66-1.75 (m, 4H), 1.43-1.61 (m, 8H).

Example 12

Synthesis of Compound 12

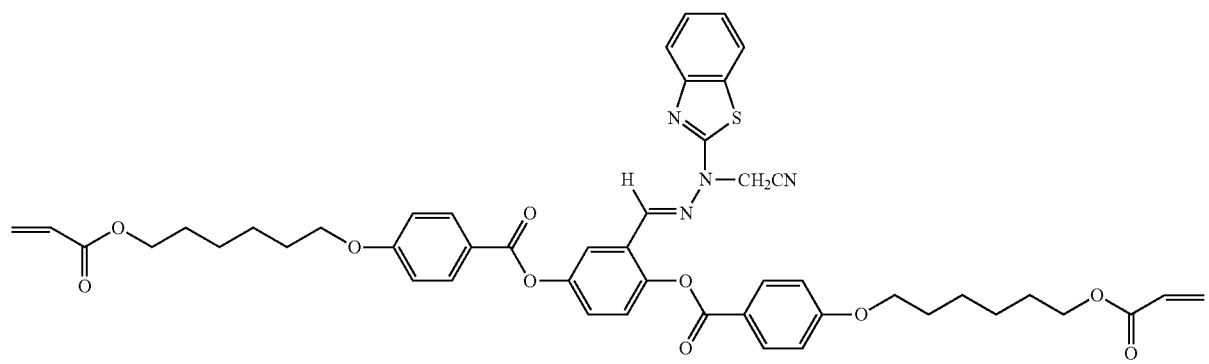

Compound 12

Step 1: Synthesis of Intermediate L

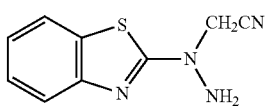
Intermediate L

A four-necked reactor equipped with a thermometer was charged with 2.00 g (12.1 mmol) of 2-hydrazinobenzothiazole and 20 ml of DMF under a nitrogen stream to prepare a homogeneous solution. After the addition of 8.36 g (60.5 mmol) of potassium carbonate and 959 mg (12.7 mmol) of chloromethyl cyanide to the solution, the mixture was stirred at 60° C. for 6 hours. After completion of the reaction, the reaction mixture was cooled to 20° C., added to 200 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=60:40 (volume ratio)) to obtain 1.20 g of an intermediate L as a white solid (yield: 48.6%).

The structure of the target product was identified by $^1$H-NMR and mass spectroscopy.

$^1$H-NMR (500 MHz, CDCl$_3$, TMS, δ ppm): 7.67 (dd, 1H, J=1.0 Hz, 8.0 Hz), 7.62 (dd, 1H, J=1.0 Hz, 8.0 Hz), 7.35 (ddd, 1H, J=1.0 Hz, 7.5 Hz, 8.0 Hz), 7.18 (ddd, 1H, J=1.0 Hz, 7.5 Hz, 8.0 Hz), 4.76 (s, 2H), 4.43 (s, 2H).

GCMS (EI-MS) calcd for C$_9$H$_8$N$_4$S: 204 [M$^+$]; Found m/z: 204.

Step 2: Synthesis of Intermediate M

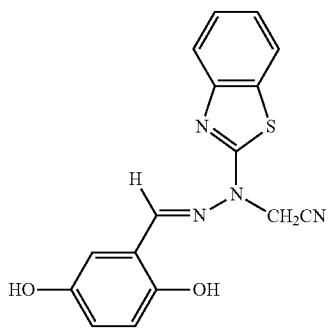
Intermediate M

A four-necked reactor equipped with a thermometer was charged with 395 mg (2.86 mmol) of 2,5-dihydroxybenzaldehyde, 700 mg (3.43 mmol) of the intermediate L, 67.4 mg (0.29 mmol) of (±)-10-camphorsulfonic acid, and 10 ml of 1-propanol under a nitrogen stream. The mixture was stirred at 80° C. for 1 hour. After completion of the reaction, the reaction mixture was cooled to 20° C., and a solid that had precipitated was filtered off. The solid was washed with 1-propanol, and dried using a vacuum dryer to obtain 788 mg of an intermediate M as a white solid (yield: 85.0%).

The structure of the target product was identified by $^1$H-NMR and mass spectroscopy.

$^1$H-NMR (400 MHz, DMSO-d$_6$, TMS, δ ppm): 9.45 (s, 1H), 8.97 (s, 1H), 8.27 (s, 1H), 7.89 (d, 1H, J=7.8 Hz), 7.66 (d, 1H, J=8.2 Hz), 7.37 (dd, 1H, J=7.3 Hz, 8.2 Hz), 7.21 (dd, 1H, J=7.3 Hz, 7.8 Hz), 7.17 (d, 1H, J=2.8 Hz), 6.76 (d, 1H, J=8.7 Hz), 6.71 (dd, 1H, J=2.8 Hz, 8.7 Hz), 5.55 (s, 2H).

LCMS (APCI) calcd for C$_{16}$H$_{12}$N$_4$O$_2$S: 324 [M$^+$]; Found m/z: 324

Step 3: Synthesis of Compound 12

A four-necked reactor equipped with a thermometer was charged with 650 mg (2.00 mmol) of the intermediate M, 1.46 g (5.00 mmol) of 4-(6-acryloylhex-1-yloxy)benzoic acid (manufactured by DKSH Japan K.K.), 122 mg (1.00 mmol) of 4-(dimethylamino)pyridine, and 15 ml of N-methylpyrrolidone under a nitrogen stream to prepare a homogeneous solution. After the addition of 1.15 g (6.00 mmol) of WSC to the solution, the mixture was stirred at 25° C. for 18 hours. After completion of the reaction, the reaction mixture was added to 300 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a white solid. The white solid was purified by silica gel column chromatography (toluene: ethyl acetate=95:5 (volume ratio)) to obtain 907 mg of a compound 12 as a white solid (yield: 51.8%).

The structure of the target product was identified by $^1$H-NMR and mass spectroscopy.

$^1$H-NMR (500 MHz, CDCl$_3$, TMS, δ ppm): 8.22 (d, 2H, J=9.0 Hz), 8.19 (d, 2H, J=9.0 Hz), 7.98 (s, 1H), 7.89 (d, 1H, J=3.0 Hz), 7.64-7.68 (m, 2H), 7.35-7.38 (m, 2H), 7.33 (dd, 1H, J=3.0 Hz, 9.0 Hz), 7.20 (ddd, 1H, J=1.0 Hz, 7.5 Hz, 8.0 Hz), 7.02 (d, 2H, J=9.0 Hz), 7.01 (d, 2H, J=9.0 Hz), 6.41 (dd, 2H, J=1.5 Hz, 17.5 Hz), 6.14 (dd, 2H, J=10.5 Hz, 17.5 Hz), 5.38 (dd, 2H, J=1.5 Hz, 10.5 Hz), 5.22 (s, 2H), 4.194 (t, 2H, J=6.5 Hz), 4.191 (t, 2H, J=6.5 Hz), 4.08 (t, 2H, J=6.5 Hz), 4.07 (t, 2H, J=6.5 Hz), 1.81-1.87 (m, 4H), 1.71-1.77 (m, 4H), 1.47-1.58 (m, 8H).

LCMS (APCI) calcd for C$_{48}$H$_{48}$N$_4$O$_{10}$S: 872 [M$^+$]; Found m/z: 872

Example 13

Synthesis of Compound 13

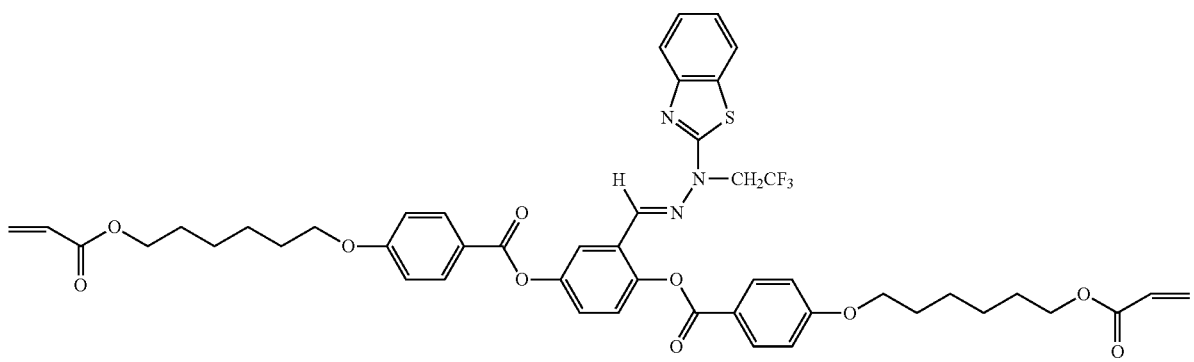
Compound 13

Step 1: Synthesis of Intermediate N

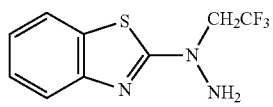

Intermediate N

A four-necked reactor equipped with a thermometer was charged with 2.00 g (12.1 mmol) of 2-hydrazinobenzothiazole and 20 ml of DMF under a nitrogen stream to prepare a homogeneous solution. After the addition of 8.36 g (60.5 mmol) of potassium carbonate and 3.05 g (14.5 mmol) of 1,1,1-trifluoro-2-iodoethane to the solution, the mixture was stirred at 50° C. for 6 hours. After completion of the reaction, the reaction mixture was cooled to 20° C., added to 200 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=75:25 (volume ratio)) to obtain 1.83 g of an intermediate N as a white solid (yield: 61.1%).

The structure of the target product was identified by $^1$H-NMR and mass spectroscopy.

$^1$H-NMR (500 MHz, CDCl$_3$, TMS, δ ppm): 7.62 (d, 1H, J=8.0 Hz), 7.58 (d, 1H, J=8.0 Hz), 7.31 (dd, 1H, J=8.0 Hz, 8.5 Hz), 7.11 (dd, 1H, J=8.0 Hz, 8.5 Hz), 4.52 (s, 2H), 4.43 (d, 1H, J=8.5 Hz), 4.40 (d, 1H, J=8.5 Hz).

GCMS (EI-MS) calcd for C$_{16}$H$_{12}$F$_3$N$_3$O$_2$S: 367 [M$^+$]; Found m/z: 367.

Step 2: Synthesis of Intermediate O

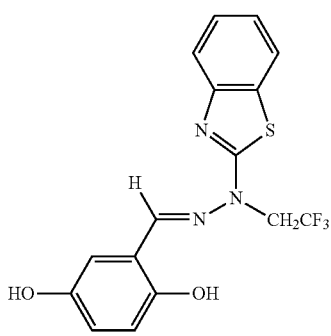

Intermediate O

A four-necked reactor equipped with a thermometer was charged with 1.02 g (7.40 mmol) of 2,5-dihydroxybenzaldehyde, 1.83 g (7.40 mmol) of the intermediate N, and 20 ml of 1-propanol under a nitrogen stream. The mixture was stirred at 80° C. for 3 hours. After completion of the reaction, the reaction mixture was cooled to 20° C., and a solid that had precipitated was filtered off. The solid was washed with 1-propanol, and dried using a vacuum dryer to obtain 1.96 g of an intermediate O as a white solid (yield: 71.9%).

The structure of the target product was identified by $^1$H-NMR and mass spectroscopy.

$^1$H-NMR (500 MHz, DMSO-d$_6$, TMS, δ ppm): 9.43 (s, 1H), 9.00 (s, 1H), 8.36 (s, 1H), 7.90 (dd, 1H, J=1.0 Hz, 8.0 Hz), 7.67 (dd, 1H, J=1.0 Hz, 7.5 Hz), 7.38 (ddd, 1H, J=1.0 Hz, 7.5 Hz, 8.0 Hz), 7.23 (ddd, 1H, J=1.0 Hz, 8.0 Hz, 8.0 Hz), 7.19 (d, 1H, J=3.0 Hz), 6.77 (d, 1H, J=8.8 Hz), 6.73 (dd, 1H, J=3.0 Hz, 8.8 Hz), 5.33 (d, 1H, J=9.0 Hz), 5.29 (d, 1H, J=9.0 Hz).

Step 3: Synthesis of Compound 13

A four-necked reactor equipped with a thermometer was charged with 1.85 g (4.85 mmol) of the intermediate O, 3.54 g (12.1 mmol) of 4-(6-acryloylhex-1-yloxy)benzoic acid (manufactured by DKSH Japan K.K.), 296 mg (2.43 mmol) of 4-(dimethylamino)pyridine, and 40 ml of N-methylpyrrolidone under a nitrogen stream to prepare a homogeneous solution. After the addition of 2.80 g (14.6 mmol) of WSC to the solution, the mixture was stirred at 25° C. for 12 hours. After completion of the reaction, the reaction mixture was added to 300 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a white solid. The white solid was purified by silica gel column chromatography (toluene:ethyl acetate=95:5 (volume ratio)) to obtain 3.31 g of a compound 13 as a white solid (yield: 74.5%).

The structure of the target product was identified by $^1$H-NMR and mass spectroscopy.

$^1$H-NMR (500 MHz, CDCl$_3$, TMS, δ ppm): 8.20 (d, 2H, J=9.0 Hz), 8.17 (d, 2H, J=9.0 Hz), 8.01 (s, 1H), 7.89 (d, 1H, J=2.5 Hz), 7.65-7.70 (m, 2H), 7.33-7.36 (m, 2H), 7.31 (dd, 1H, J=2.5 Hz, 6.5 Hz), 7.18 (ddd, 1H, J=1.0 Hz, 7.3 Hz, 8.0 Hz), 7.01 (d, 4H, J=9.0 Hz), 6.41 (dd, 2H, J=1.0 Hz, 17.5 Hz), 6.14 (dd, 2H, J=10.5 Hz, 17.5 Hz), 5.83 (dd, 2H, J=1.0 Hz, 10.5 Hz), 4.92 (d, 1H, J=8.0 Hz), 4.88 (d, 1H, J=8.0 Hz), 4.19 (t, 4H, J=7.0 Hz), 4.08 (t, 4H, J=6.5 Hz), 1.84-1.89 (m, 4H), 1.71-1.77 (m, 4H), 1.46-1.56 (m, 8H).

LCMS (APCI) calcd for C$_{48}$H$_{48}$F$_3$N$_3$O$_{10}$S: 915 [M$^+$]; Found m/z: 915.

Example 14

Synthesis of Compound 14

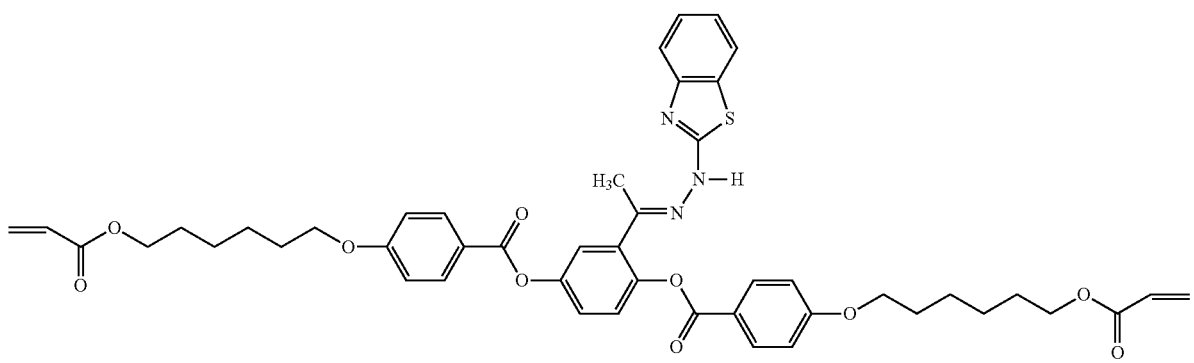

Compound 14

Step 1: Synthesis of Intermediate P

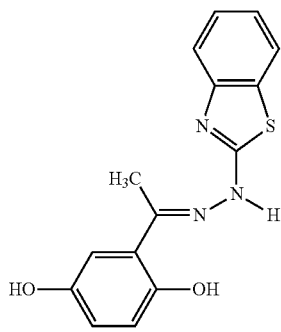

Intermediate P

A four-necked reactor equipped with a thermometer was charged with 3.0 g (19.7 mmol) of 2,5-dihydroxyacetophenone, 3.91 g (23.7 mmol) of 2-hydrazinobenzothiazole, and 50 ml of 1-propanol under a nitrogen stream. The mixture was stirred at 80° C. for 9 hours. After completion of the reaction, the reaction mixture was cooled to 20° C., and added to a mixed solvent of water/methanol (=2/1 (volume ratio)), and a solid that had precipitated was filtered off. The solid was dried using a vacuum dryer to obtain 2.33 g of an intermediate P as a yellow solid (yield: 39.5%).

The structure of the target product was identified by $^1$H-NMR.

$^1$H-NMR (500 MHz, DMSO-$d_6$, TMS, δ ppm): 12.40-11.40 (br, 2H), 9.20-8.70 (br, 1H), 7.67 (d, 1H, J=8.0 Hz), 7.28 (dd, 1H, J=8.0 Hz, 8.0 Hz), 7.21-7.14 (br, 1H), 7.07 (dd, 1H, J=8.0 Hz, 8.0 Hz), 6.98 (s, 1H), 6.74 (s, 2H), 2.46 (s, 3H).

Step 2: Synthesis of Compound 14

A four-necked reactor equipped with a thermometer was charged with 1.50 g (5.01 mmol) of the intermediate P, 3.66 g (12.5 mmol) of 4-(6-acryloylhex-1-yloxy)benzoic acid (manufactured by DKSH Japan K.K.), 184 mg (1.50 mmol) of 4-(dimethylamino)pyridine, and 30 ml of N-methylpyrrolidone under a nitrogen stream to prepare a homogeneous solution. After the addition of 2.88 g (15.0 mmol) of WSC to the solution, the mixture was stirred at 25° C. for 20 hours. After completion of the reaction, the reaction mixture was added to 300 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=80:20 (volume ratio)) to obtain 2.56 g of a compound 14 as a light yellow solid (yield: 60.3%).

The structure of the target product was identified by $^1$H-NMR.

$^1$H-NMR (500 MHz, CDCl$_3$, TMS, δ ppm): 8.17 (d, 2H, J=9.0 Hz), 8.13 (d, 2H, J=9.0 Hz), 7.61 (d, 1H, J=7.5 Hz), 7.53 (d, 1H, J=7.5 Hz), 7.49 (dd, 1H, J=0.5 Hz, 2.5 Hz), 7.31-7.27 (m, 4H), 7.13 (t, 1H, J=8.0 Hz), 6.99 (d, 2H, J=9.0 Hz), 6.93 (d, 2H, J=9.0 Hz), 6.410 (dd, 1H, J=1.5 Hz, 17.5 Hz), 6.405 (dd, 1H, J=1.5 Hz, 17.5 Hz), 6.10 (dd, 1H, J=10.5 Hz, 17.5 Hz), 6.13 (dd, 1H, J=10.5 Hz, 17.5 Hz), 5.83 (dd, 1H, J=1.5 Hz, 10.5 Hz), 5.82 (dd, 1H, J=1.5 Hz, 10.5 Hz), 4.19 (t, 2H, J=6.5 Hz), 4.18 (t, 2H, J=6.5 Hz), 6.04 (t, 2H, J=6.5 Hz), 4.00 (t, 2H, J=6.5 Hz), 2.25 (s, 3H), 1.88-1.79 (m, 4H), 1.76-1.69 (m, 4H), 1.58-1.42 (m, 8H).

Example 15

Synthesis of Compound 15

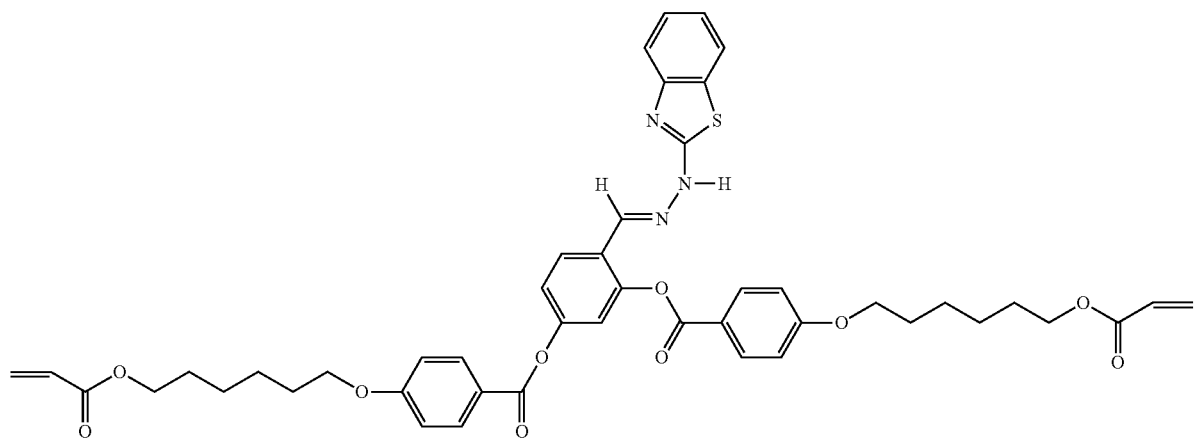

Compound 15

Step 1: Synthesis of Intermediate Q

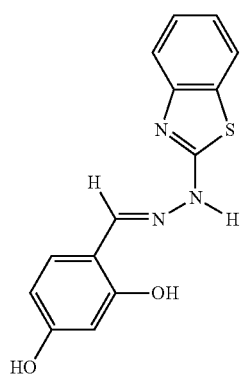

Intermediate Q

A four-necked reactor equipped with a thermometer was charged with 10.0 g (72.4 mol) of 2,4-dihydroxybenzaldehyde and 150 ml of ethanol under a nitrogen stream to prepare a homogeneous solution. After the addition of 13.0 g (79.6 mol) of 2-hydrazinobenzothiazole to the solution, the mixture was reacted at 25° C. for 2 hours. After completion of the reaction, a solid that had precipitated was filtered off by suction filtration. The solid was washed with ethanol, and dried using a vacuum dryer to obtain 13.0 g of an intermediate Q as a light yellow solid (yield: 63.9%).

The structure of the target product was identified by $^1$H-NMR.

$^1$H-NMR (500 MHz, DMSO-$d_6$, TMS, δ ppm): 12.00 (brs, 1H), 9.39 (s, 1H), 9.24 (s, 1H), 7.96 (s, 1H), 7.76 (s, 1H), 7.41 (d, 1H, J=7.5 Hz), 7.28 (dd, 1H, J=7.5 Hz, 7.5 Hz), 7.20 (d, 1H, J=2.0 Hz), 7.09 (dd, 1H, J=7.5 Hz, 7.5 Hz), 6.92 (dd, 1H, J=2.0 Hz, 8.0 Hz), 6.79 (d, 1H, J=8.0 Hz).

Step 2: Synthesis of Compound 15

A four-necked reactor equipped with a thermometer was charged with 947 mg (3.32 mmol) of the intermediate Q synthesized by the step 1, 2.42 g (8.29 mmol) of 4-(6-acryloylhex-1-yloxy)benzoic acid (manufactured by DKSH Japan K.K.), 203 mg (1.66 mmol) of 4-(dimethylamino)pyridine, and 50 ml of N-methylpyrrolidone under a nitrogen stream to prepare a homogeneous solution. After the addition of 1.91 g (9.96 mmol) of WSC to the solution, the mixture was stirred at 25° C. for 16 hours. After completion of the reaction, the reaction mixture was added to 200 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=95:5 (volume ratio)) to obtain 1.6 g of a compound 15 as a light yellow solid (yield: 58.2%).

The structure of the target product was identified by $^1$H-NMR.

$^1$H-NMR (400 MHz, DMSO-$d_6$, TMS, δ ppm): 12.38 (brs, 1H), 8.16 (s, 1H), 7.89 (d, 2H, J=8.7 Hz), 7.87 (d, 2H, J=8.7 Hz), 7.67-7.74 (m, 3H), 7.51 (d, 1H, J=7.8 Hz), 7.41 (brs, 1H), 7.26 (dd, 1H, J=7.8 Hz, 7.8 Hz), 7.07 (dd, 1H, J=7.8 Hz, 7.8 Hz), 6.95 (d, 2H, J=8.2 Hz), 6.94 (d, 2H, J=8.2 Hz), 6.27 (dd, 2H, J=1.4 Hz, 17.4 Hz), 6.12 (dd, 2H, J=10.1 Hz, 17.4 Hz), 5.87 (dd, 2H, J=1.4 Hz, 10.1 Hz), 4.06 (t, 4H, J=6.6 Hz), 3.96-4.00 (m, 4H), 1.64-1.69 (m, 4H), 1.55-1.62 (m, 4H), 1.33-1.42 (m, 8H).

Example 16

Synthesis of Compound 16

Compound 16

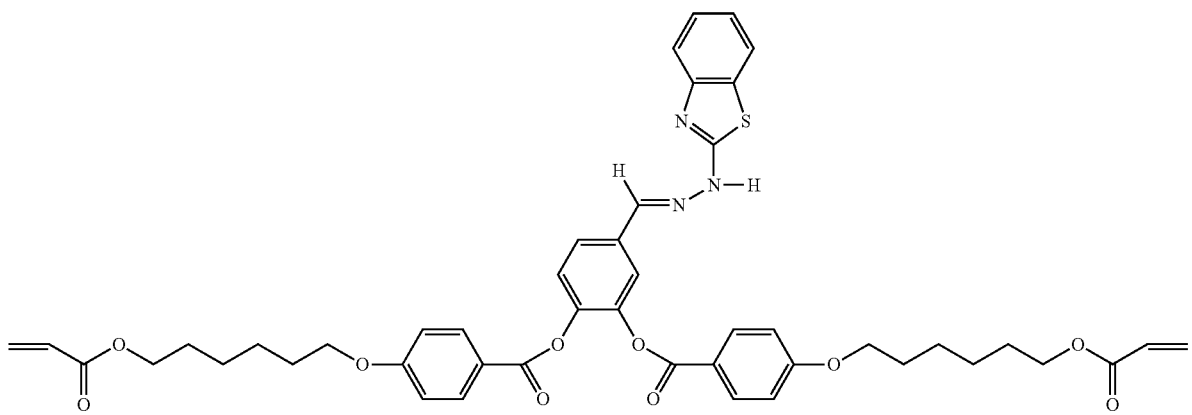

Step 1: Synthesis of Intermediate R

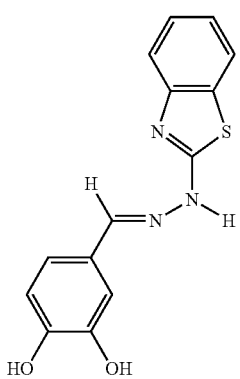

Intermediate R

A four-necked reactor equipped with a thermometer was charged with 10.0 g (72.4 mol) of 3,4-dihydroxybenzaldehyde and 150 ml of ethanol under a nitrogen stream to prepare a homogeneous solution. After the addition of 13.0 g (79.6 mol) of 2-hydrazinobenzothiazole to the solution, the mixture was stirred at 25° C. for 5 hours. After completion of the reaction, a solid that had precipitated was filtered off by suction filtration. The solid was washed with ethanol, and dried using a vacuum dryer to obtain 17.0 g of an intermediate R as a light yellow solid (yield: 81.2%).

The structure of the target product was identified by $^1$H-NMR.

$^1$H-NMR (500 MHz, DMSO-$d_6$, TMS, δ ppm): 11.95 (brs, 1H), 10.58 (brs, 1H), 9.90 (s, 1H), 8.34 (s, 1H), 7.71 (d, 1H, J=8.0 Hz), 7.39 (d, 1H, J=8.0 Hz), 7.26-7.33 (m, 2H), 7.07 (dd, 1H, J=8.0 Hz, 8.0 Hz), 6.37 (dd, 1H, J=2.5 Hz, 8.3 Hz), 6.35 (d, 1H, J=2.5 Hz).

Step 2: Synthesis of Compound 16

A four-necked reactor equipped with a thermometer was charged with 1.41 g (4.97 mmol) of the intermediate R synthesized by the step 1, 3.63 g (12.4 mmol) of 4-(6-acryloylhex-1-yloxy)benzoic acid (manufactured by DKSH Japan K.K.), 304 mg (2.49 mmol) of 4-(dimethylamino)pyridine, and 60 ml of N-methylpyrrolidone under a nitrogen stream to prepare a homogeneous solution. After the addition of 2.56 g (14.9 mmol) of WSC to the solution, the mixture was stirred at 25° C. for 15 hours. After completion of the reaction, the reaction mixture was added to 200 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=95:5 (volume ratio)) to obtain 3.21 g of a polymerizable compound 16 as a white solid (yield: 77.5%).

The structure of the target product was identified by $^1$H-NMR.

$^1$H-NMR (400 MHz, DMSO-$d_6$, TMS, δ ppm): 12.23 (brs, 1H), 8.17 (s, 1H), 8.10 (d, 2H, J=8.7 Hz), 8.04 (d, 2H, J=8.7 Hz), 7.97 (d, 1H, J=8.7 Hz), 7.67 (d, 1H, J=7.8 Hz), 7.31-7.40 (m, 3H), 7.25 (dd, 1H, J=7.8 Hz, 7.8 Hz), 7.05-7.14 (m, 5H), 6.29 (dd, 2H, J=1.4 Hz, 17.4 Hz), 6.14 (dd, 2H, J=10.6 Hz, 17.4 Hz), 5.90 (dd, 2H, J=1.4 Hz, 10.6 Hz), 4.09-4.10 (m, 8H), 1.68-1.78 (m, 4H), 1.57-1.65 (m, 4H), 1.35-1.47 (m, 8H).

Example 17

Synthesis of Compound 17

Step 1: Synthesis of Intermediate S

Intermediate S

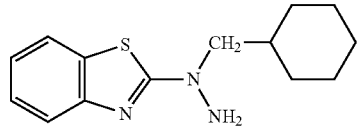

A four-necked reactor equipped with a thermometer was charged with 3.00 g (18.2 mmol) of 2-hydrazinobenzothiazole and 30 ml of DMF under a nitrogen stream to prepare a homogeneous solution. After the addition of 7.55 g (54.6 mmol) of potassium carbonate and 3.86 g (21.8 mmol) of (bromomethyl)cyclohexane to the solution, the mixture was stirred at 80° C. for 9 hours. After completion of the reaction, the reaction mixture was cooled to 20° C., added to 300 ml of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=85:15 (volume ratio)) to obtain 2.36 g of an intermediate S as a white solid (yield: 49.7%).

The structure of the target product was identified by $^1$H-NMR.

$^1$H-NMR (400 MHz, CDCl$_3$, TMS, δ ppm): 7.58 (d, 1H, J=8.0 Hz), 7.51 (d, 1H, J=8.1 Hz), 7.26 (dd, 1H, J=7.0 Hz, 8.1 Hz), 7.04 (dd, 1H, J=7.0 Hz, 8.0 Hz), 4.24 (s, 2H), 3.59 (d, 2H, J=7.4 Hz), 1.84-1.92 (m, 1H), 1.67-1.77 (m, 5H), 1.16-1.29 (m, 3H), 1.02-1.13 (m, 2H).

Step 2: Synthesis of Intermediate T

Intermediate T

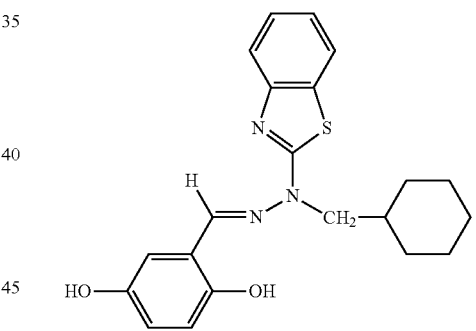

A four-necked reactor equipped with a thermometer was charged with 1.06 g (7.65 mmol) of 2,5-dihydroxybenzalde- Compound 17

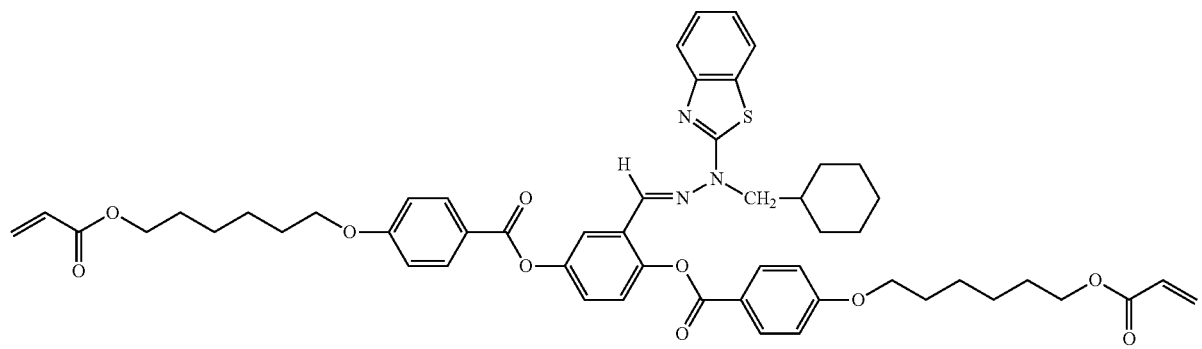

hyde, 2.00 g (7.65 mmol) of the intermediate S synthesized by the step 1, and 20 ml of 1-propanol under a nitrogen stream to prepare a homogenous solution. The solution was stirred at 80° C. for 5 hours. After completion of the reaction, the reaction mixture was cooled to 20° C., and a solid that had precipitated was filtered off. The solid was washed with 1-propanol, and dried using a vacuum dryer to obtain 2.00 g of an intermediate T as a white solid (yield: 70.8%).

The structure of the target product was identified by $^1$H-NMR.

$^1$H-NMR (400 MHz, DMSO-$d_6$, TMS, δ ppm): 9.33 (s, 1H), 8.93 (s, 1H), 8.11 (s, 1H), 7.79 (d, 1H, J=7.5 Hz), 7.55 (d, 1H, J=7.8 Hz), 7.28 (dd, 1H, J=7.8 Hz, 7.8 Hz), 7.15 (s, 1H), 7.11 (dd, 1H, J=7.5 Hz, 7.8 Hz), 6.72 (d, 1H, J=8.7 Hz), 6.66 (d, 1H, J=8.7 Hz), 4.17 (d, 2H, J=7.3 Hz), 1.82-1.92 (m, 1H), 1.56-1.63 (m, 5H), 1.01-1.19 (m, 5H).

Step 3: Synthesis of Compound 17

A four-necked reactor equipped with a thermometer was charged with 2.00 g (5.42 mmol) of the intermediate T synthesized by the step 2, 3.83 g (13.1 mmol) of 4-(6-acryloyl-hex-1-yloxy)benzoic acid (manufactured by DKSH Japan K.K.), 320 mg (2.62 mmol) of 4-(dimethylamino)pyridine, and 20 ml of N-methylpyrrolidone under a nitrogen stream to prepare a homogeneous solution. After the addition of 3.01 g (15.7 mmol) of WSC to the solution, the mixture was stirred at 25° C. for 16 hours. After completion of the reaction, the reaction mixture was added to 300 ml of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a white solid. The white solid was purified by silica gel column chromatography (toluene:ethyl acetate=95:5 (volume ratio)) to obtain 2.68 g of a compound 17 as a white solid (yield: 55.0%).

The structure of the target product was identified by $^1$H-NMR.

$^1$H-NMR (500 MHz, CDCl$_3$, TMS, δ ppm): 8.20 (d, 2H, J=8.7 Hz), 8.18 (d, 2H, J=8.7 Hz), 7.89 (d, 1H, J=2.9 Hz), 7.76 (s, 1H), 7.61 (d, 2H, J=8.2 Hz), 7.24-7.30 (m, 3H), 7.11 (dd, 1H, J=7.3 Hz, 7.8 Hz), 7.00 (d, 4H, J=8.7 Hz), 6.41 (d, 2H, J=17.4 Hz), 6.13 (dd, 2H, J=10.5 Hz, 17.4 Hz), 5.82 (d, 2H, J=10.5 Hz), 4.19 (t, 4H, J=6.4 Hz), 4.04-4.08 (m, 6H), 1.82-1.89 (m, 4H), 1.70-1.77 (m, 5H), 1.48-1.59 (m, 13H), 0.96-1.03 (m, 5H).

Example 18

Synthesis of Compound 18

Step 1: Synthesis of Intermediate U

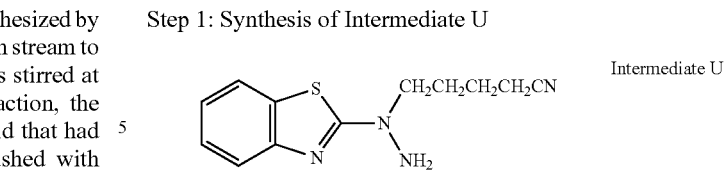

Intermediate U

A four-necked reactor equipped with a thermometer was charged with 5.00 g (30.3 mmol) of 2-hydrazinobenzothiazole and 100 ml of DMF under a nitrogen stream to prepare a homogeneous solution. After the addition of 20.9 g (152 mmol) of potassium carbonate and 5.17 g (30.3 mmol) of 5-bromovaleronitrile to the solution, the mixture was stirred at 60° C. for 8 hours. After completion of the reaction, the reaction mixture was cooled to 20° C., added to 500 ml of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=60:40 (volume ratio)) to obtain 3.41 g of an intermediate U as a white solid (yield: 45.7%).

The structure of the target product was identified by $^1$H-NMR.

$^1$H-NMR (400 MHz, CDCl$_3$, TMS, δ ppm): 7.60 (d, 1H, J=7.8 Hz), 7.51 (d, 1H, J=8.1 Hz), 7.28 (dd, 1H, J=7.3 Hz, 8.1 Hz), 7.07 (dd, 1H, J=7.3 Hz, 7.8 Hz), 4.23 (s, 2H), 3.81 (t, 2H, J=6.9 Hz), 2.46 (t, 2H, J=7.1 Hz), 1.88-1.95 (m, 2H), 1.71-1.79 (m, 2H).

Step 2: Synthesis of Intermediate V

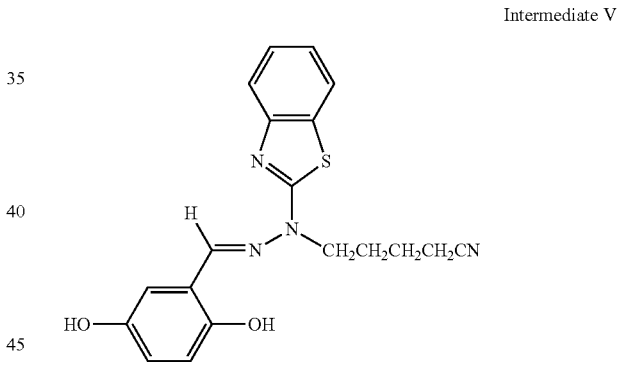

Intermediate V

A four-necked reactor equipped with a thermometer was charged with 1.62 g (11.7 mmol) of 2,5-dihydroxybenzalde-

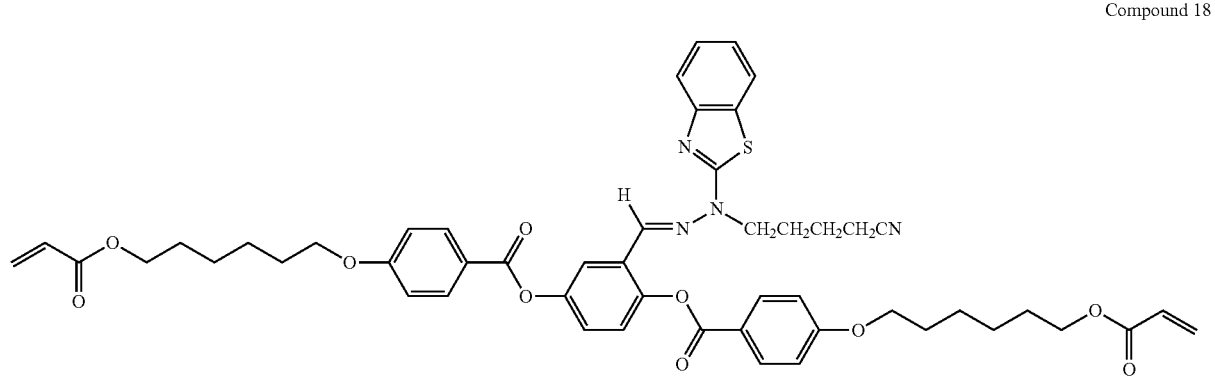

Compound 18 hyde, 2.89 g (11.7 mmol) of the intermediate U synthesized by the step 1, and 30 ml of 1-propanol under a nitrogen stream to prepare a homogenous solution. The solution was stirred at 80° C. for 7 hours. After completion of the reaction, the reaction mixture was cooled to 20° C., and a solid that had precipitated was filtered off. The solid was washed with 1-propanol, and dried using a vacuum dryer to obtain 2.92 g of an intermediate V as a white solid (yield: 68.2%).

The structure of the target product was identified by $^1$H-NMR.

$^1$H-NMR (400 MHz, DMSO-d$_6$, TMS, δ ppm): 9.36 (s, 1H), 8.94 (s, 1H), 8.13 (s, 1H), 7.81 (d, 1H, J=7.3 Hz), 7.57 (d, 1H, J=7.6 Hz), 7.30 (dd, 1H, J=7.6 Hz, 8.0 Hz), 7.14 (d, 1H, J=3.2 Hz), 7.13 (dd, 1H, J=7.3 Hz, 8.0 Hz), 6.73 (d, 1H, J=8.7 Hz), 6.67 (dd, 1H, J=3.2 Hz, 8.7 Hz), 4.34 (t, 2H, J=7.1 Hz), 2.57 (t, 2H, J=7.2 Hz), 1.72-1.79 (m, 2H), 1.59-1.66 (m, 2H).

Step 3: Synthesis of Compound 18

A four-necked reactor equipped with a thermometer was charged with 1.90 g (5.19 mmol) of the intermediate V synthesized by the step 2, 3.79 g (13.0 mmol) of 4-(6-acryloyl-hex-1-yloxy)benzoic acid (manufactured by DKSH Japan K.K.), 318 mg (2.60 mmol) of 4-(dimethylamino)pyridine, and 20 ml of N-methylpyrrolidone under a nitrogen stream to prepare a homogeneous solution. After the addition of 2.98 g (15.6 mmol) of WSC to the solution, the mixture was stirred at 25° C. for 16 hours. After completion of the reaction, the reaction mixture was added to 300 ml of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a white solid. The white solid was purified by silica gel column chromatography (toluene:ethyl acetate=95:5 (volume ratio)) to obtain 1.92 g of a compound 18 as a white solid (yield: 40.4%).

The structure of the target product was identified by $^1$H-NMR.

$^1$H-NMR (400 MHz, CDCl$_3$, TMS, δ ppm): 8.19 (d, 4H, J=8.2 Hz), 7.88 (s, 1H), 7.73 (s, 1H), 7.61 (d, 1H, J=7.8 Hz), 7.60 (d, 1H, J=6.9 Hz), 7.27-7.33 (m, 3H), 7.13 (dd, 1H, J=7.3 Hz, 7.8 Hz), 7.03 (d, 2H, J=8.7 Hz), 6.99 (d, 2H, J=9.2 Hz), 6.41 (dd, 2H, J=1.4 Hz, 17.4 Hz), 6.13 (dd, 2H, J=10.5 Hz, 17.4 Hz), 5.82 (dd, 2H, J=1.4 Hz, 10.5 Hz), 4.27 (t, 2H, J=6.9 Hz), 4.19 (t, 2H, J=6.6 Hz), 4.18 (t, 2H, J=6.6 Hz), 4.08 (t, 2H, J=6.0 Hz), 4.07 (t, 2H, J=6.4 Hz), 2.30 (t, 2H, J=7.1 Hz), 1.82-1.89 (m, 4H), 1.70-1.78 (m, 6H), 1.45-1.60 (m, 10H).

Example 19

Synthesis of Compound 19

Step 1: Synthesis of Intermediate W

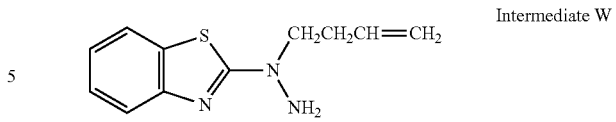

Intermediate W

A four-necked reactor equipped with a thermometer was charged with 3.00 g (18.2 mmol) of 2-hydrazinobenzothiazole and 30 ml of DMF under a nitrogen stream to prepare a homogeneous solution. After the addition of 7.55 g (54.6 mmol) of potassium carbonate and 2.94 g (21.8 mmol) of 4-bromo-1-butene to the solution, the mixture was stirred at 80° C. for 4 hours. After completion of the reaction, the reaction mixture was cooled to 20° C., added to 300 ml of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=85:15 (volume ratio)) to obtain 1.44 g of an intermediate W as a white solid (yield: 36.1%).

The structure of the target product was identified by $^1$H-NMR.

$^1$H-NMR (500 MHz, CDCl$_3$, TMS, δ ppm): 7.60 (d, 1H, J=7.8 Hz), 7.54 (d, 1H, J=7.5 Hz), 7.30 (dd, 1H, J=7.8 Hz, 7.8 Hz), 7.07 (dd, 1H, J=7.5 Hz, 7.8 Hz), 5.89 (ddt, 1H, J=10.3 Hz, 17.0 Hz, 7.0 Hz), 5.18 (dd, 1H, J=1.5 Hz, 17.0 Hz), 5.09 (dd, 1H, J=1.5 Hz, 10.3 Hz), 4.27 (s, 2H), 3.86 (t, 2H, J=7.0 Hz), 2.53 (dt, 2H, J=7.0 Hz, 7.0 Hz).

Step 2: Synthesis of Intermediate X

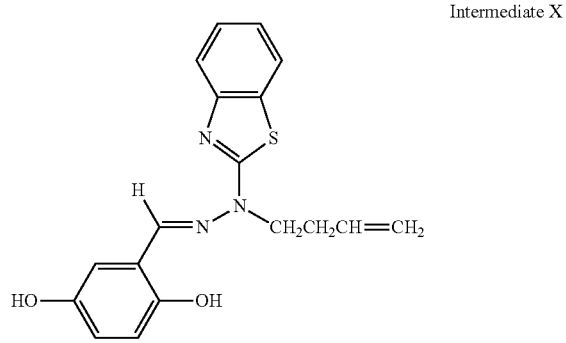

Intermediate X

A four-necked reactor equipped with a thermometer was charged with 630 mg (4.56 mmol) of 2,5-dihydroxybenzaldehyde, 1.00 g (4.56 mmol) of the intermediate W synthesized by the step 1, and 15 ml of 1-propanol under a nitrogen Compound 19

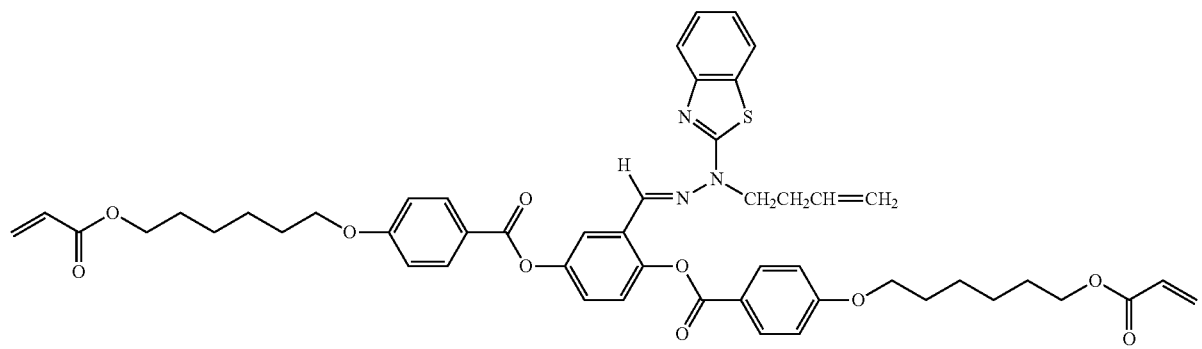

stream. The mixture was stirred at 80° C. for 6 hours. After completion of the reaction, the reaction mixture was cooled to 20° C., and a solid that had precipitated was filtered off. The solid was washed with 1-propanol, and dried using a vacuum dryer to obtain 760 mg of an intermediate X as a white solid (yield: 49.1%).

The structure of the target product was identified by $^1$H-NMR.

$^1$H-NMR (500 MHz, CDCl$_3$, TMS, δ ppm): 9.77 (s, 1H), 7.80 (s, 1H), 7.693 (d, 1H, J=7.8 Hz), 7.687 (d, 1H, J=7.8 Hz), 7.37 (dd, 1H, J=7.5 Hz, 7.8 Hz), 7.19 (dd, 1H, J=7.5 Hz, 7.8 Hz), 6.94 (d, 1H, J=9.0 Hz), 6.83 (dd, 1H, J=3.0 Hz, 9.0 Hz), 6.78 (d, 1H, J=3.0 Hz), 5.90 (ddt, 1H, J=10.3 Hz, 17.0 Hz, 7.5 Hz), 5.19 (dd, 1H, J=1.5 Hz, 17.0 Hz), 5.13 (dd, 1H, J=1.5 Hz, 10.3 Hz), 4.71 (s, 1H), 4.45 (t, 2H, J=7.5 Hz), 2.56 (dt, 2H, J=7.5 Hz, 7.5 Hz).

Step 3: Synthesis of Compound 19

A four-necked reactor equipped with a thermometer was charged with 560 mg (1.65 mmol) of the intermediate X synthesized by the step 2, 1.21 g (4.13 mmol) of 4-(6-acryloylhex-1-yloxy)benzoic acid (manufactured by DKSH Japan K.K.), 100.8 mg (0.825 mmol) of 4-(dimethylamino)pyridine, and 20 ml of N-methylpyrrolidone under a nitrogen stream to prepare a homogeneous solution. After the addition of 948 mg (4.95 mmol) of WSC to the solution, the mixture was stirred at 25° C. for 16 hours. After completion of the reaction, the reaction mixture was added to 200 ml of water, and extracted with 250 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a white solid. The white solid was purified by silica gel column chromatography (toluene:ethyl acetate=90:10 (volume ratio)) to obtain 1.09 g of a compound 19 as a white solid (yield: 74.4%).

The structure of the target product was identified by $^1$H-NMR.

$^1$H-NMR (500 MHz, CDCl$_3$, TMS, δ ppm): 8.21 (d, 2H, J=9.0 Hz), 8.19 (d, 2H, J=9.0 Hz), 7.90 (d, 1H, J=2.0 Hz), 7.80 (s, 1H), 7.64 (d, 1H, J=7.3 Hz), 7.63 (d, 1H, J=8.0 Hz), 7.28-7.33 (m, 3H), 7.13 (dd, 1H, J=7.3 Hz, 7.8 Hz), 7.01 (d, 4H, J=9.0 Hz), 6.42 (dd, 2H, J=1.5 Hz, 17.5 Hz), 6.14 (dd, 2H, J=10.5 Hz, 17.5 Hz), 5.83 (dd, 2H, J=1.5 Hz, 10.5 Hz), 5.62-5.70 (m, 1H), 4.86-4.90 (m, 2H), 4.26 (t, 2H, J=7.0 Hz), 4.20 (t, 4H, J=6.5 Hz), 4.080 (t, 2H, J=6.0 Hz), 4.076 (t, 2H, J=6.0 Hz), 2.39 (dt, 2H, J=7.5 Hz, 7.5 Hz), 1.84-1.90 (m, 4H), 1.72-1.77 (m, 4H), 1.46-1.59 (m, 8H).

Example 20

Synthesis of Compound 20

Step 1: Synthesis of Intermediate Y

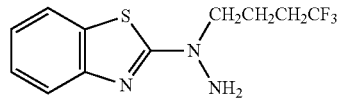

Intermediate Y

A four-necked reactor equipped with a thermometer was charged with 1.45 g (8.75 mmol) of 2-hydrazinobenzothiazole and 20 ml of DMF under a nitrogen stream to prepare a homogeneous solution. After the addition of 3.63 g (26.3 mmol) of potassium carbonate and 2.50 g (10.5 mmol) of 1,1,1-trifluoro-4-iodobutane the solution, the mixture was stirred at 80° C. for 8 hours. After completion of the reaction, the reaction mixture was cooled to 20° C., added to 200 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=85:15 (volume ratio)) to obtain 961 mg of an intermediate Y as a white solid (yield: 39.9%).

The structure of the target product was identified by $^1$H-NMR.

$^1$H-NMR (500 MHz, CDCl$_3$, TMS, δ ppm): 7.61 (d, 1H, J=8.0 Hz), 7.54 (d, 1H, J=7.8 Hz), 7.30 (dd, 1H, J=7.8 Hz, 7.8 Hz), 7.09 (dd, 1H, J=7.8 Hz, 8.0 Hz), 4.24 (s, 2H), 3.81 (t, 2H, J=7.0 Hz), 2.16-2.26 (m, 2H), 1.99-2.05 (m, 2H).

Step 2: Synthesis of Intermediate Z

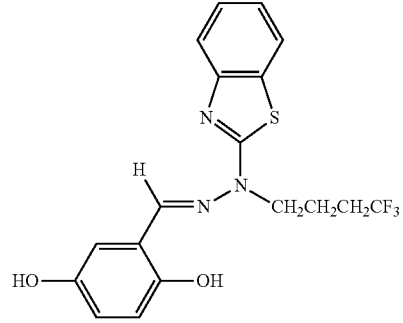

Intermediate Z

A four-necked reactor equipped with a thermometer was charged with 372 mg (2.69 mmol) of 2,5-dihydroxybenzaldehyde, 740 mg (2.69 mmol) of the intermediate Y synthesized by the step 1, and 10 ml of 1-propanol under a nitrogen stream. The mixture was stirred at 80° C. for 6 hours. After

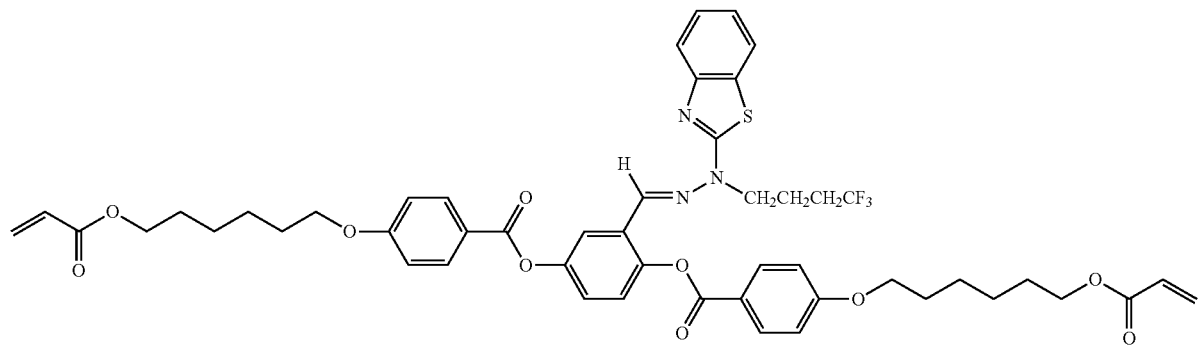

Compound 20 completion of the reaction, the reaction mixture was cooled to 20° C., and a solid that had precipitated was filtered off. The solid was washed with 1-propanol, and dried using a vacuum dryer to obtain 916 mg of an intermediate Z as a white solid (yield: 86.1%).

The structure of the target product was identified by $^1$H-NMR.

$^1$H-NMR (500 MHz, DMSO-$d_6$, TMS, δ ppm): 9.39 (s, 1H), 8.98 (s, 1H), 8.18 (s, 1H), 7.85 (d, 1H, J=7.8 Hz), 7.61 (d, 1H, J=8.1 Hz), 7.35 (dd, 1H, J=7.3 Hz, 8.1 Hz), 7.16-7.19 (m, 2H), 6.76 (d, 1H, J=9.0 Hz), 6.71 (dd, 1H, J=3.0 Hz, 9.0 Hz), 4.42 (t, 2H, J=7.5 Hz), 2.40-2.50 (m, 2H), 1.88-1.97 (m, 2H).

Step 3: Synthesis of Compound 20

A four-necked reactor equipped with a thermometer was charged with 575 mg (1.45 mmol) of the intermediate Z synthesized by the step 2, 1.06 g (3.64 mmol) of 4-(6-acryloylhex-1-yloxy)benzoic acid (manufactured by DKSH Japan K.K.), 88.6 mg (0.73 mmol) of 4-(dimethylamino)pyridine, and 10 ml of N-methylpyrrolidone under a nitrogen stream to prepare a homogeneous solution. After the addition of 834 mg (4.35 mmol) of WSC to the solution, the mixture was stirred at 25° C. for 16 hours. After completion of the reaction, the reaction mixture was added to 150 ml of water, and extracted with 200 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a white solid. The white solid was purified by silica gel column chromatography (toluene:ethyl acetate=95:5 (volume ratio)) to obtain 1.13 g of a compound 20 as a white solid (yield: 82.6%).

The structure of the target product was identified by $^1$H-NMR.

$^1$H-NMR (500 MHz, CDCl$_3$, TMS, δ ppm): 8.20 (d, 2H, J=8.5 Hz), 8.18 (d, 2H, J=8.5 Hz), 7.90 (d, 1H, J=2.9 Hz), 7.75 (s, 1H), 7.62-7.66 (m, 2H), 7.27-7.34 (m, 3H), 7.15 (dd, 1H, J=7.5 Hz, 7.5 Hz), 7.01 (d, 4H, J=8.5 Hz), 6.41 (dd, 2H, J=1.5 Hz, 17.5 Hz), 6.14 (dd, 2H, J=10.5 Hz, 17.5 Hz), 5.83 (d, 2H, J=1.5 Hz, 10.5 Hz), 4.28 (t, 2H, J=7.0 Hz), 4.194 (t, 2H, J=6.5 Hz), 4.191 (t, 2H, J=6.5 Hz), 4.08 (t, 2H, J=6.5 Hz), 4.07 (t, 2H, J=6.5 Hz), 2.01-2.12 (m, 2H), 1.83 (t, 6H), 1.71-1.77 (m, 4H) 1.45-1.59 (m, 8H).

The phase transition temperature was measured by the following method using the compounds 1 to 20 obtained in Examples 1 to 20, the compound 1r of Reference Example 1 that was used in Comparative Example 1 ("K35" manufactured by Zeon Corporation), and the compound 2r of Reference Example 2 that was used in Comparative Example 2 ("LC242" manufactured by BASF).

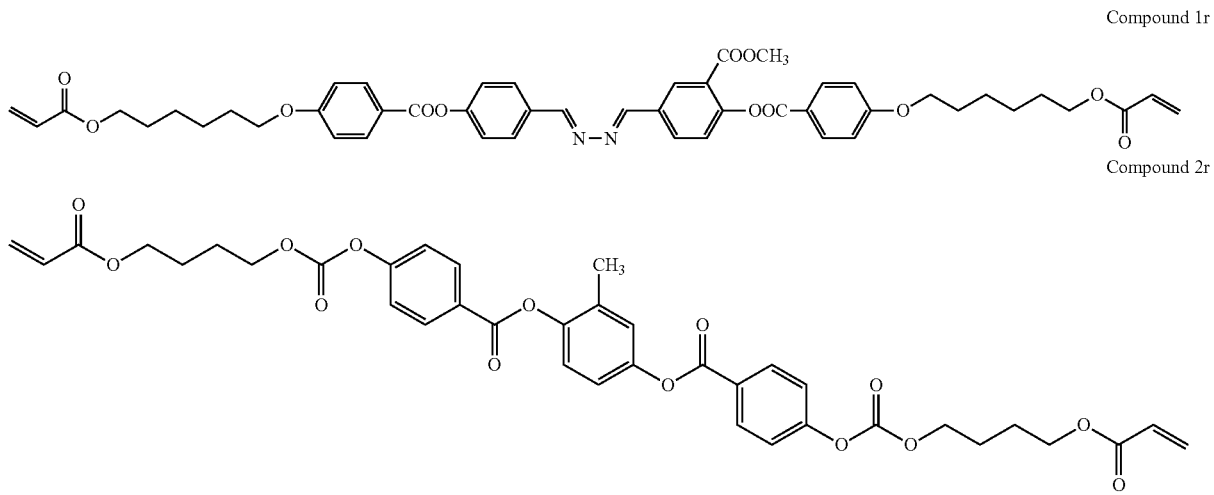

Compound 1r

Compound 2r

Phase Transition Temperature Measurement 1

10 mg of each compound (compounds 1 to 20, compound 1r, and compound 2r) was weighed, and placed in a solid state between two glass substrates provided with a polyimide alignment film subjected to a rubbing treatment. The substrates were placed on a hot plate, heated from 50° C. to 200° C., and cooled to 50° C. A change in structure during a change in temperature was observed using a polarizing optical microscope ("ECLIPSE LV100POL" manufactured by Nikon Corporation).

The phase transition temperature measurement results are shown in Table 1.

In Table 1, "C" indicates "crystal", "N" indicates "nematic", and "I" indicates "isotropic". The term "crystal" means that the test compound was in a solid phase, the term "nematic" means that the test compound was in a nematic liquid crystal phase, and the term "isotropic" means that the test compound was in an isotropic liquid phase.

Note that the compounds 12 and 15 underwent thermal polymerization when increasing the temperature, and the phase transition temperature could not be measured. Note also that a nematic liquid crystal phase and a solid phase could not be observed when the compound 14 was cooled up to 50° C.

TABLE 1

| | Polymerizable compound | Phase transition temperature |
|---|---|---|
| Example 1 | Compound 1 | C ⇌ (102° C. / 50° C. or less) N ⇌ (165° C. / 140° C.) I |
| Example 2 | Compound 2 | C ⇌ (150° C. / 113° C.) N ⇌ (155° C. / 150° C.) I |
| Example 3 | Compound 3 | C ⇌ (119° C. / 50° C. or less) N → (70° C.) I |

TABLE 1-continued

| | Polymerizable compound | Phase transition temperature |
|---|---|---|
| Example 4 | Compound 4 | C ⇌ N (50° C. or less / 85° C. / 75° C.) I |
| Example 5 | Compound 5 | C ⇌ N (50° C. or less / 90° C.) ⇌ (111° C. / 112° C.) I |
| Example 6 | Compound 6 | C ⇌ N (50° C. or less / 116° C.) ⇌ (120° C. / 127° C.) I |
| Example 7 | Compound 7 | C ⇌ N (50° C. or less / 107° C. / 94° C.) I |
| Example 8 | Compound 8 | C ⇌ N (50° C. or less / 97° C. / 77° C.) I |
| Example 9 | Compound 9 | C ⇌ N (50° C. or less / 83° C.) ⇌ (82° C. / 85° C.) I |
| Example 10 | Compound 10 | C ⇌ N (50° C. or less / 138° C.) ⇌ (140° C. / 151° C.) I |
| Example 11 | Compound 11 | C ⇌ N (112° C. / 160° C.) ⇌ (163° C. / 168° C.) I |
| Example 12 | Compound 12 | C ⇌ N (Unclear due to thermal polymerization / 103° C.) I |
| Example 13 | Compound 13 | C ⇌ (146° C. / 170° C.) I |
| Example 14 | Compound 14 | C ⇌ N (Unclear (50° C. or less) / 70° C.) I |
| Example 15 | Compound 15 | C ⇌ N (Unclear due to thermal polymerization / 128° C.) I |
| Example 16 | Compound 16 | C ⇌ (91° C. / 125° C.) I |
| Example 17 | Compound 17 | C ⇌ N (50° C. or less / 120° C. / 66° C.) I |
| Example 18 | Compound 18 | C ⇌ N (50° C. or less / 115° C. / 79° C.) I |
| Example 19 | Compound 19 | C ⇌ N (80° C. / 112° C. / 87° C.) I |
| Example 20 | Compound 20 | C ⇌ N (50° C. or less / 111° C. / 58° C.) I |
| Reference Example 1 | Compound 1r | C ⇌ N (50° C. or less / 80° C.) ⇌ (200° C. or more) I |
| Reference Example 2 | Compound 2r | C ⇌ N (50° C. or less / 60° C.) ⇌ (122° C. / 123° C.) I |

Examples 21 to 25

1 g of the corresponding compound among the compounds 1 to 5 obtained in Examples 1 to 5, 30 mg of Irgacure 907 (manufactured by BASF) (photoinitiator), and 100 mg of a 1% cyclopentanone solution of KH-40 (manufactured by AGC Seimi Chemical Co., Ltd.) (surfactant) were dissolved in 2.3 g of cyclopentanone. The solution was filtered through a disposable filter having a pore size of 0.45 μm to obtain a polymerizable composition (polymerizable compositions 1 to 5).

Examples 26 to 35, 43, 44, and 47, and Comparative Examples 1 and 2

1 g of the corresponding compound among the compounds 1 to 10 obtained in Examples 1 to 10, the compounds 17 and 18 obtained in Examples 17 and 18, the compound 20 obtained in Example 20, the compound 1r of Reference Example 1, and the compound 2r of Reference Example 2, 30 mg of Adekaoptomer N-1919 (manufactured by ADEKA Corporation (hereinafter the same)) (photoinitiator), and 100 mg of a 1% cyclopentanone solution of KH-40 (surfactant) were dissolved in 2.3 g of cyclopentanone. The solution was filtered through a disposable filter having a pore size of 0.45 μm to obtain a polymerizable composition (polymerizable compositions 6 to 15, 23, 24, 27, 1r, and, 2r).

Examples 36 to 41 and 45

0.8 g of the compound 1 obtained in Example 1, 0.2 g of the corresponding compound among the compounds 11 to 16 obtained in Examples 11 to 16, and the compound 19 obtained in Example 19, 30 mg of Adekaoptomer N-1919 (photoinitiator), and 100 mg of a 1% cyclopentanone solution of KH-40 (surfactant) were dissolved in 2.3 g of cyclopentanone. The solution was filtered through a disposable filter having a pore size of 0.45 μm to obtain a polymerizable composition (polymerizable compositions 16 to 21 and 25).

Example 42

0.33 g of the compound 13 obtained in Example 13, 0.67 g of a polymerizable liquid crystal compound ("LC242" manufactured by BASF, compound 2r), 30 mg of Adekaoptomer N-1919 (photoinitiator), and 100 mg of a 1% cyclopentanone solution of KH-40 (surfactant) were dissolved in 2.3 g of cyclopentanone. The solution was filtered through a disposable filter having a pore size of 0.45 μm to obtain a polymerizable composition (polymerizable composition 22).

Example 46

0.5 g of the compound 19 obtained in Example 19, 0.5 g of a polymerizable liquid crystal compound ("LC242" manufactured by BASF, compound 2r), 30 mg of Adekaoptomer N-1919 (photoinitiator), and 100 mg of a 1% cyclopentanone solution of KH-40 (surfactant) were dissolved in 2.3 g of cyclopentanone. The solution was filtered through a disposable filter having a pore size of 0.45 μm to obtain a polymerizable composition (polymerizable composition 26).

The polymerizable compositions 1 to 27, 1r, and 2r were polymerized to obtain polymers. The retardation was measured, and the wavelength dispersion was evaluated using the resulting polymers.

Measurement 1 of Retardation and Evaluation 1 of Wavelength Dispersion (i) Preparation of Transparent Resin Substrate Provided with Alignment Film Each side of an alicyclic olefin polymer film ("ZeonorFilm ZF16-100" manufactured by Zeon Corporation) (thickness: 100 μm) was subjected to a corona discharge treatment. A 5% polyvinyl alcohol aqueous solution was applied to one side of the film using a #2 wire bar, and the film was dried to form an alignment film having a thickness of 0.1 μm. The alignment film was subjected to a rubbing treatment to prepare a transparent resin substrate on which the alignment film was formed.

(ii) Formation of Liquid Crystal Layer Using Polymerizable Composition

Wavelength dispersion measurement samples of Examples 21 to 47 and Comparative Examples 1 and 2 were prepared as described below.

The polymerizable composition (polymerizable compositions 6 to 27, 1r, and 2r) was applied to the surface of the transparent resin substrate on which the alignment film was formed, using a #4 wire bar. After drying the film for 30 seconds at the temperature shown in Table 2 or 3, the film was subjected to an alignment treatment for 1 minute at the temperature shown in Table 2 or 3 to form a liquid crystal layer having a thickness of about 1.5 μm. UV rays were applied to the liquid crystal layer at a dose of 2000 mJ/cm² to effect polymerization to prepare a wavelength dispersion measurement sample. Note that exposure was performed at 125° C. in Example 27, and performed at 23° C. in Examples 21 to 26 and 28 to 47 and Comparative Examples 1 and 2.

(iii) Measurement of Retardation

The retardation between 400 nm and 800 nm was measured using the sample utilizing an ellipsometer ("XLS-100" manufactured by J. A. Woollam).

(iv) Evaluation of Wavelength Dispersion

The wavelength dispersion was evaluated from the values α and β calculated by the following expressions using the measured retardation.

α=(retardation at 449.9 nm)/(retardation at 548.5 nm)   [Expression 1]

β=(retardation at 650.2 nm)/(retardation at 548.5 nm)   [Expression 2]

The value α is smaller than 1, and the value β is larger than 1 when ideal wideband wavelength dispersion (reverse wavelength dispersion) is achieved. The values α and β are almost identical when flat wavelength dispersion is achieved. The value α is larger than 1, and the value β is smaller than 1 when normal dispersion is achieved.

Specifically, flat wavelength dispersion that ensures that the values α and β are almost identical is preferable, and reverse wavelength dispersion that ensures that the value α is smaller than 1, and the value β is larger than 1 is particularly preferable.

Tables 2 and 3 show the type and the content (%) of the polymerizable compound 1 and the type and the content (%) of the polymerizable compound 2 in the polymerizable compositions 1 to 27, 1r, and 2r used in Examples 21 to 47 and Comparative Examples 1 and 2, the drying temperature for the films of the polymerizable compositions 1 to 27, 1r, and 2r, the alignment temperature, the thickness (μm) of the liquid crystalline polymer films obtained by polymerizing the polymerizable compositions 1 to 27, 1r, and 2r, the retardation (Re) at a wavelength of 548.5 nm, and the values α and β.

Figure 2:
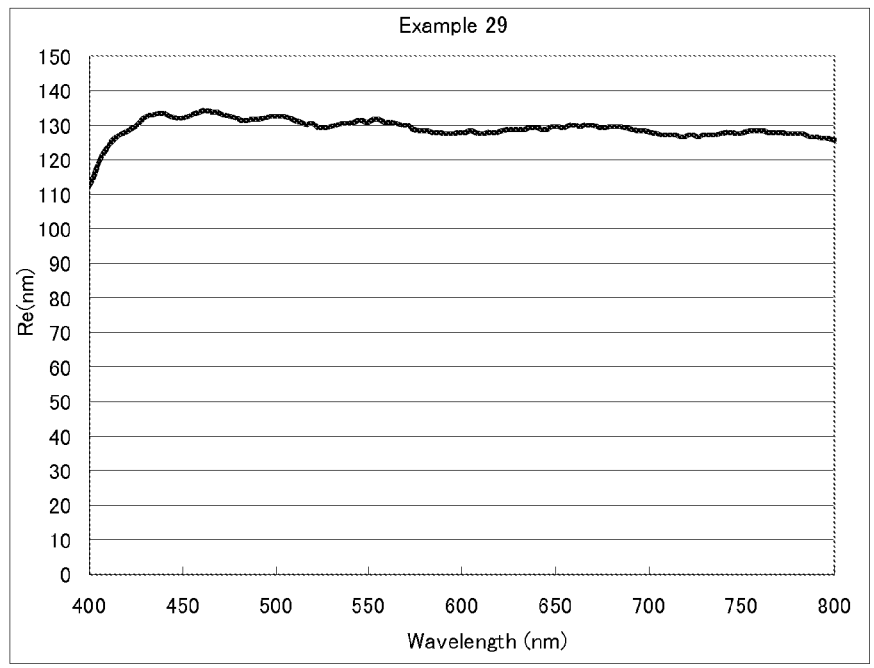
FIG. 2 is a view showing the wavelength dispersion of the liquid crystalline polymer film obtained by polymerizing the polymerizable composition 9 of Example 29.
Figure 3:
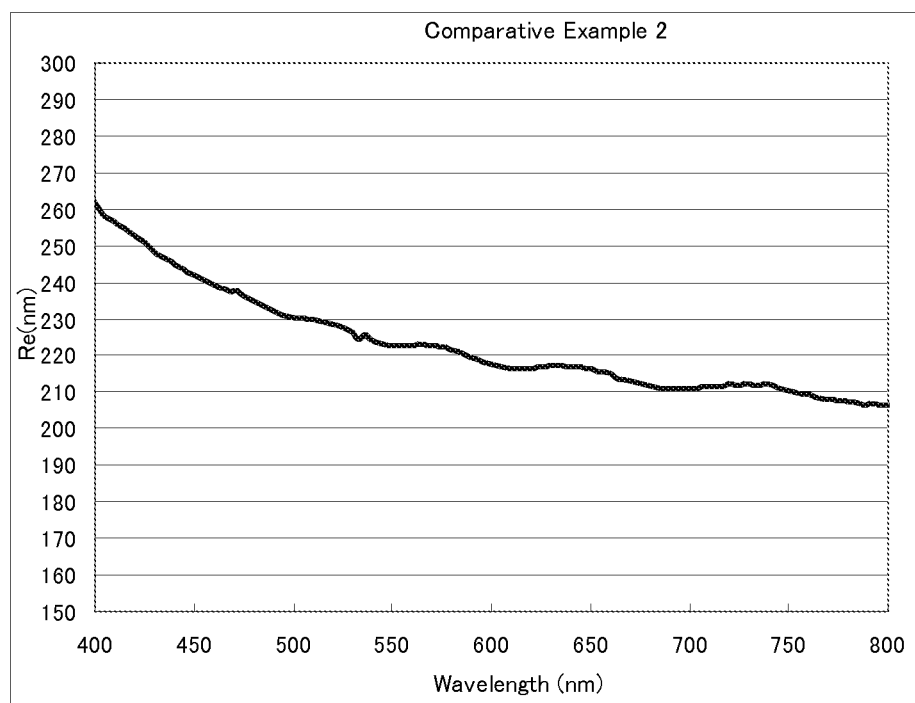
FIG. 3 is a view showing the wavelength dispersion of the liquid crystalline polymer film obtained by polymerizing the polymerizable composition 2r of Comparative Example 2.

FIGS. 1 to 3 show the wavelength dispersion of the liquid crystalline polymer films (liquid crystal layers) obtained by polymerizing the polymerizable compositions of Example 26, Example 29, and Comparative Example 2.

In FIGS. 1 to 3, the horizontal axis indicates the measurement wavelength (nm), and the vertical axis indicates the retardation (Re).

Note that the values α and β of the polymerizable composition can be determined by calculations (simulation). For example, the values α and β of Comparative Example 1 are respectively 1.298 and 0.995, and the values α and β of Comparative Example 2 are respectively 1.260 and 0.943.

TABLE 2

|  | Polymerizable composition | Polymerizable compound | Drying temperature (° C.) | Alignment temperature (° C.) | α Re(450)/Re(550) | β Re(650)/Re(550) |
|---|---|---|---|---|---|---|
| Example 21 | 1 | Compound 1 | 110 | 23 | 0.902 | 1.012 |
| Example 22 | 2 | Compound 2 | 158 | 125 | 1.011 | 0.999 |
| Example 23 | 3 | Compound 3 | 125 | 65 | 0.905 | 0.976 |
| Example 24 | 4 | Compound 4 | 90 | 65 | 1.005 | 0.985 |
| Example 25 | 5 | Compound 5 | 100 | 23 | 0.914 | 1.026 |

TABLE 3

| | Polymerizable composition | Polymerizable compound 1 | | Polymerizable compound 2 | | Drying temperature (° C.) | Alignment temperature (° C.) | Re (548.5 nm) | α | β | Film thickness (μm) |
|---|---|---|---|---|---|---|---|---|---|---|---|
| | | Compound | Content (%) | Compound | Content (%) | | | | | | |
| Example 26 | 6 | Compound 1 | 100 | — | — | 110 | 23 | 129.59 | 0.902 | 1.012 | 1.350 |
| Example 27 | 7 | Compound 2 | 100 | — | — | 158 | 125 | 126.04 | 1.011 | 0.999 | 1.478 |
| Example 28 | 8 | Compound 3 | 100 | — | — | 125 | 65 | 149.70 | 0.905 | 0.976 | 1.421 |
| Example 29 | 9 | Compound 4 | 100 | — | — | 90 | 65 | 131.02 | 1.005 | 0.985 | 1.565 |
| Example 30 | 10 | Compound 5 | 100 | — | — | 100 | 23 | 163.78 | 0.914 | 1.026 | 1.574 |
| Example 31 | 11 | Compound 6 | 100 | — | — | 135 | 23 | 127.53 | 0.047 | 1.075 | 1.588 |
| Example 32 | 12 | Compound 7 | 100 | — | — | 110 | 23 | 164.16 | 0.949 | 0.982 | 1.598 |
| Example 33 | 13 | Compound 8 | 100 | — | — | 110 | 23 | 146.90 | 0.946 | 1.002 | 1.577 |
| Example 34 | 14 | Compound 9 | 100 | — | — | 100 | 23 | 151.10 | 0.932 | 1.004 | 1.434 |
| Example 35 | 15 | Compound 10 | 100 | — | — | 145 | 50 | 147.13 | 1.011 | 0.998 | 1.481 |
| Example 36 | 16 | Compound 1 | 80 | Compound 11 | 20 | 110 | 23 | 137.07 | 0.947 | 0.986 | 1.373 |
| Example 37 | 17 | Compound 1 | 80 | Compound 12 | 20 | 110 | 23 | 139.14 | 0.923 | 0.997 | 1.577 |
| Example 38 | 18 | Compound 1 | 80 | Compound 13 | 20 | 110 | 23 | 163.04 | 0.931 | 1.018 | 1.485 |
| Example 39 | 19 | Compound 1 | 80 | Compound 14 | 20 | 110 | 23 | 150.59 | 0.928 | 0.983 | 1.580 |
| Example 40 | 20 | Compound 1 | 80 | Compound 15 | 20 | 110 | 23 | 139.15 | 0.979 | 0.981 | 1.493 |
| Example 41 | 21 | Compound 1 | 80 | Compound 16 | 20 | 110 | 23 | 139.29 | 0.974 | 0.985 | 1.526 |
| Example 42 | 22 | Compound 13 | 33 | Compound 2r | 67 | 120 | 23 | 104.81 | 0.964 | 1.000 | 1.191 |
| Example 43 | 23 | Compound 17 | 100 | — | — | 125 | 60 | 132.10 | 0.941 | 1.001 | 1.575 |
| Example 44 | 24 | Compound 18 | 100 | — | — | 125 | 60 | 144.16 | 0.946 | 1.013 | 1.558 |
| Example 45 | 25 | Compound 1 | 80 | Compound 19 | 20 | 110 | 23 | 146.46 | 0.921 | 1.029 | 1.514 |
| Example 46 | 26 | Compound 19 | 50 | Compound 2r | 50 | 100 | 23 | 181.45 | 1.029 | 0.999 | 1.436 |
| Example 47 | 27 | Compound 20 | 100 | — | — | 120 | 50 | 109.51 | 0.947 | 0.972 | 1.470 |
| Comparative Example 1 | 1r | Compound 1r | 100 | — | — | 90 | 23 | 355.97 | 1.193 | 0.918 | 1.509 |
| Comparative Example 2 | 2r | Compound 2r | 100 | — | — | 80 | 23 | 222.90 | 1.086 | 0.970 | 1.479 |

As is clear from the results shown in Tables 2 and 3, it was confirmed that optically anisotropic articles (polymers) were obtained in Examples 21 to 47. The values α and β were almost identical when using the optically anisotropic articles obtained in Examples 21 to 30 and 32 to 47. The optically anisotropic articles obtained in Examples 21, 25, 26, 30, 33, 34, 38, and 43 to 45 are particularly preferable since the value α was smaller than 1, and the value β was larger than 1.

When using the optically anisotropic articles obtained in Comparative Examples 1 and 2, the value α was significantly larger than 1, and the value β was smaller than 1.

As shown in FIG. 1, the liquid crystalline polymer film obtained by polymerizing the polymerizable composition of Example 26 showed reverse wavelength dispersion in which the retardation at a long wavelength is larger than the retardation at a short wavelength. As shown in FIG. 2, the liquid crystalline polymer film obtained by polymerizing the polymerizable composition of Example 29 showed flat wavelength dispersion close to reverse wavelength dispersion. As shown in FIG. 3, the liquid crystalline polymer film obtained by polymerizing the polymerizable composition of Comparative Example 2 showed normal wavelength dispersion in which the retardation at a short wavelength is larger than the retardation at a long wavelength.

Example 48

Synthesis of Compound 21

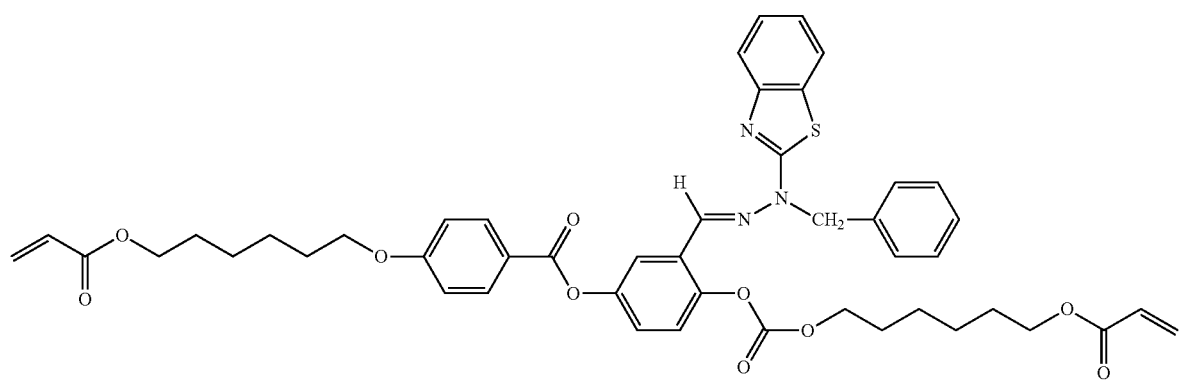

Compound 21

Step 1: Synthesis of Intermediate a

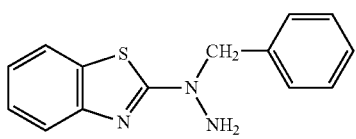
Intermediate a

A four-necked reactor equipped with a thermometer was charged with 2.0 g (10.3 mmol) of benzyl hydrazine dihydrochloride and 10 ml of tTriethylamine under a nitrogen stream to prepare a homogeneous solution. After the addition of 3.48 g (20.5 mmol) of 2-chlorobenzothiazole to the solution, the mixture was stirred at 80° C. for 30 minutes. After completion of the reaction, the reaction mixture was cooled to 20° C., added to 100 ml of a saturated sodium hydrogen carbonate aqueous solution, and extracted with 200 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane: ethyl acetate=75:25 (volume ratio)) to obtain 1.76 g of an intermediate a as a white solid (yield: 66.9%).

The structure of the target product was identified by $^1$H-NMR.

$^1$H-NMR (400 MHz, CDCl$_3$, TMS, δ ppm): 7.62 (dd, 1H, J=0.8 Hz, 7.7 Hz), 7.57 (d, 1H, J=8.1 Hz), 7.28-7.39 (m, 6H), 7.09 (ddd, 1H, J=1.1 Hz, 7.5 Hz, 7.7 Hz), 5.00 (s, 2H), 4.07 (s, 2H).

Step 2: Synthesis of Intermediate b

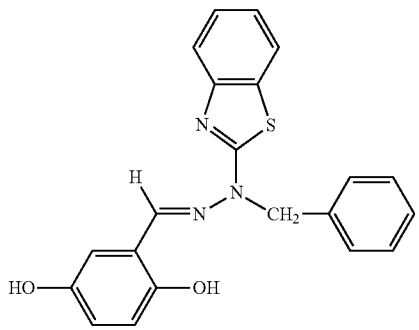
Intermediate b

A four-necked reactor equipped with a thermometer was charged with 952 mg (6.89 mmol) of 2,5-dihydroxybenzaldehyde, 1.76 g (6.89 mmol) of the intermediate a synthesized by the step 1, and 15 ml of 2-propanol under a nitrogen stream. The mixture was stirred at 80° C. for 1.5 hours. After completion of the reaction, the reaction mixture was cooled to 20° C., and a solid that had precipitated was filtered off. The solid was washed with 2-propanol, and dried using a vacuum dryer to obtain 1.60 g of an intermediate b as a white solid (yield: 61.9%).

The structure of the target product was identified by $^1$H-NMR.

$^1$H-NMR (400 MHz, DMSO-d$_6$, TMS, δ ppm): 9.20 (s, 1H), 8.90 (s, 1H), 7.99 (s, 1H), 7.85 (dd, 1H, J=0.9 Hz, 7.8 Hz), 7.56 (d, 1H, J=7.8 Hz), 7.29-7.34 (m, 3H), 7.22-7.26 (m, 3H), 7.15 (ddd, 1H, J=0.9 Hz, 7.3 Hz, 7.8 Hz) 7.12 (d, 1H, J=1.8 Hz), 6.63 (d, 2H, J=2.2 Hz), 5.59 (s, 2H).

Step 3: Synthesis of Compound 21

A four-necked reactor equipped with a thermometer was charged with 1.60 g (4.26 mmol) of the intermediate b synthesized by the step 2, 3.11 g (10.7 mmol) of 4-(6-acryloylhex-1-yloxy)benzoic acid (manufactured by DKSH Japan K.K.), 260 mg (2.13 mmol) of 4-(dimethylamino)pyridine, and 25 ml of N-methylpyrrolidone under a nitrogen stream to prepare a homogeneous solution. After the addition of 2.45 g (12.8 mmol) of WSC to the solution, the mixture was stirred at 25° C. for 16 hours. After completion of the reaction, the reaction mixture was added to 300 ml of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a white solid. The white solid was purified by silica gel column chromatography (toluene:ethyl acetate=90:10 (volume ratio)) to obtain 1.78 g of a compound 21 as a white solid (yield: 45.2%).

The structure of the target product was identified by $^1$H-NMR.

$^1$H-NMR (500 MHz, CDCl$_3$, TMS, δ ppm): 8.19 (d, 2H, J=9.0 Hz), 7.99 (d, 2H, J=9.0 Hz), 7.88 (d, 1H, J=2.5 Hz), 7.71 (s, 1H), 7.67 (d, 1H, J=8.0 Hz), 7.64 (d, 1H, J=8.0 Hz), 7.32 (ddd, 1H, J=1.0 Hz, 7.5 Hz, 8.0 Hz), 7.12-7.22 (m, 4H), 7.04-7.09 (m, 4H), 7.01 (d, 2H, J=9.0 Hz), 7.00 (d, 2H, J=9.0 Hz), 6.41 (dd, 2H, J=1.5 Hz, 17.5 Hz), 6.13 (dd, 2H, J=10.5 Hz, 17.5 Hz), 5.83 (dd, 2H, J=1.5 Hz, 10.5 Hz), 5.49 (s, 2H), 4.20 (t, 2H, J=7.0 Hz), 4.19 (t, 2H, J=6.5 Hz), 4.11 (t, 2H, J=6.5 Hz), 4.07 (t, 2H, J=6.5 Hz), 1.81-1.94 (m, 4H), 1.70-1.78 (m, 4H), 1.45-1.62 (m, 8H).

Example 49

Synthesis of Compound 22

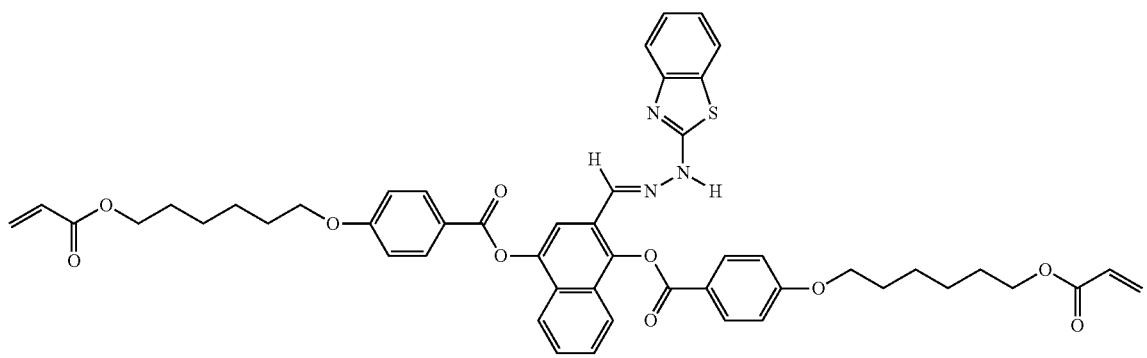
Compound 22

Step 1: Synthesis of Intermediate c

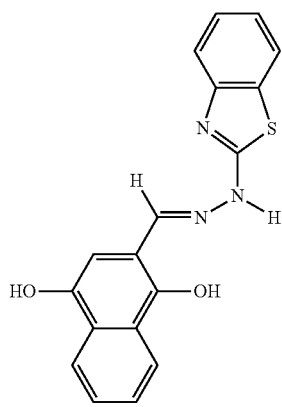

Intermediate c

A four-necked reactor equipped with a thermometer was charged with 1.00 g (5.31 mmol) of 1,4-dihydroxynaphthalene-2-carboxaldehyde, 878 mg (5.31 mmol) of 2-hydrazinobenzothiazole, and 20 ml of 1-propanol under a nitrogen stream. The mixture was refluxed for 6.5 hours. After completion of the reaction, the reaction mixture was cooled to 20° C., and a solid that had precipitated was filtered off. The solid was washed with 1-propanol, and dried using a vacuum dryer to obtain 1.63 g of an intermediate c as a yellow solid (yield: 91.5%).

The structure of the target product was identified by $^1$H-NMR.

$^1$H-NMR (400 MHz, THF-d$_8$, TMS, δ ppm): 11.35 (s, 1H), 10.89 (brs, 1H), 8.66 (s, 1H), 8.34 (s, 1H), 8.27-8.30 (m, 1H), 8.09-8.12 (m, 1H), 7.54 (d, 1H, J=7.8 Hz), 7.42-7.45 (m, 2H), 7.15-7.22 (m, 2H), 7.01 (ddd, 1H, J=1.4 Hz, 7.1 Hz, 8.0 Hz), 6.64 (s, 1H).

Step 2: Synthesis of Compound 22

A four-necked reactor equipped with a thermometer was charged with 1.50 g (4.47 mmol) of the intermediate c synthesized by the step 1, 3.27 g (11.2 mmol) of 4-(6-acryloyl-hex-1-yloxy)benzoic acid (manufactured by DKSH Japan K.K.), 273 mg (2.24 mmol) of 4-(dimethylamino)pyridine, and 15 ml of N-methylpyrrolidone under a nitrogen stream to prepare a homogeneous solution. After the addition of 2.57 g (13.4 mmol) of WSC to the solution, the mixture was stirred at 25° C. for 6 hours. After completion of the reaction, the reaction mixture was added to 100 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=90:10 (volume ratio)) to obtain 1.48 g of a compound 22 as a yellow solid (yield: 37.5%).

The structure of the target product was identified by $^1$H-NMR.

$^1$H-NMR (500 MHz, DMSO-d$_6$, TMS, δ ppm): 12.42 (brs, 1H), 8.32 (s, 1H), 8.26 (d, 2H, J=9.0 Hz), 8.24 (d, 2H, J=9.0 Hz), 7.88-7.94 (m, 2H), 7.84-7.87 (m, 1H), 7.73 (d, 1H, J=7.5 Hz), 7.64-7.66 (m, 2H), 7.47 (d, 1H, J=7.5 Hz), 7.30 (dd, 1H, J=7.5 Hz, 8.0 Hz), 7.19 (d, 2H, J=9.0 Hz), 7.16 (d, 2H, J=9.0 Hz), 7.11 (dd, 1H, J=7.5 Hz, 8.0 Hz), 6.34 (dd, 2H, J=1.5 Hz, 17.5 Hz), 6.19 (dd, 1H, J=10.5 Hz, 17.5 Hz), 6.18 (dd, 1H, J=10.5 Hz, 17.5 Hz), 5.944 (dd, 1H, J=1.5 Hz, 10.5 Hz), 5.938 (dd, 1H, J=1.5 Hz, 10.5 Hz), 4.08-4.15 (m, 8H), 1.75-1.80 (m, 4H), 1.62-1.69 (m, 4H), 1.38-1.50 (m, 8H).

Example 50

Synthesis of Compound 23

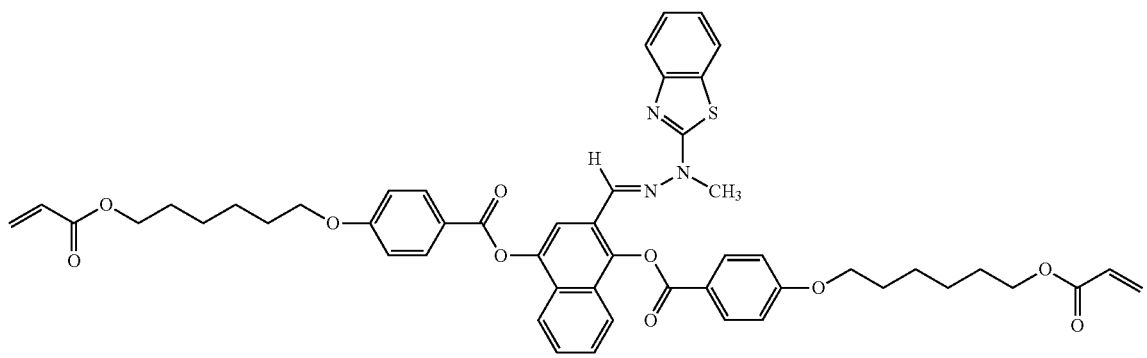

Compound 23

Step 1: Synthesis of Intermediate d

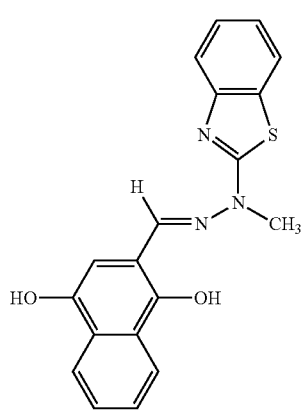

Intermediate d

A four-necked reactor equipped with a thermometer was charged with 931 mg (4.95 mmol) of 1,4-dihydroxynaphthalene-2-carboxaldehyde, 887 mg (4.95 mmol) of the intermediate D synthesized in Example 7, and 10 ml of 1-propanol under a nitrogen stream. The mixture was refluxed for 3 hours. After completion of the reaction, the reaction mixture was cooled to 20° C., and a solid that had precipitated was filtered off. The solid was washed with 1-propanol, and dried using a vacuum dryer to obtain 1.55 g of an intermediate d as a yellow solid (yield: 89.7%).

The structure of the target product was identified by $^1$H-NMR.

$^1$H-NMR (500 MHz, DMSO-$d_6$, TMS, δ ppm): 9.90 (s, 1H), 9.77 (s, 1H), 8.37 (s, 1H), 8.23 (d, 1H, J=9.5 Hz), 8.10 (d, 1H, J=9.5 Hz), 7.88 (dd, 1H, J=1.0 Hz, 9.5 Hz), 7.62 (dd, 1H, J=1.0 Hz, 7.5 Hz), 7.51-7.56 (m, 2H), 7.36 (ddd, 1H, J=1.0 Hz, 7.5 Hz, 8.0 Hz), 7.21 (s, 1H), 7.18 (ddd, 1H, J=1.0 Hz, 7.5 Hz, 7.5 Hz), 3.79 (s, 3H).

Step 2: Synthesis of Compound 23

A four-necked reactor equipped with a thermometer was charged with 1.55 g (4.44 mmol) of the intermediate d synthesized by the step 1, 3.24 g (11.1 mmol) of 4-(6-acryloyl-hex-1-yloxy)benzoic acid (manufactured by DKSH Japan K.K.), 271 mg (2.22 mmol) of 4-(dimethylamino)pyridine, and 20 ml of N-methylpyrrolidone under a nitrogen stream to prepare a homogeneous solution. After the addition of 2.55 g (13.3 mmol) of WSC to the solution, the mixture was stirred at 25° C. for 16 hours. After completion of the reaction, the reaction mixture was added to 200 ml of water, and extracted with 300 ml of ethyl acetate. After drying the ethyl acetate layer over anhydrous sodium sulfate, sodium sulfate was filtered off Ethyl acetate was evaporated from the filtrate under reduced pressure using a rotary evaporator to obtain a light yellow solid. The light yellow solid was purified by silica gel column chromatography (chloroform:methanol=95:5 (volume ratio)) to obtain 1.61 g of a compound 23 as a light yellow solid (yield: 40.4%).

The structure of the target product was identified by $^1$H-NMR.

$^1$H-NMR (500 MHz, CDCl$_3$, TMS, δ ppm): 8.34 (d, 4H, J=8.5 Hz), 8.06 (s, 1H), 7.92 (d, 1H, J=8.5 Hz), 7.87 (d, 1H, J=8.5 Hz), 7.85 (s, 1H), 7.64 (d, 2H, J=7.5 Hz), 7.51-7.53 (m, 2H), 7.32 (dd, 1H, J=7.5 Hz, 7.5 Hz), 7.14 (dd, 1H, J=7.5 Hz, 7.5 Hz), 7.08 (d, 2H, J=8.5 Hz), 7.07 (d, 2H, J=8.5 Hz), 6.42 (d, 2H, J=17.5 Hz), 7.14 (dd, 2H, J=10.5 Hz, 17.5 Hz), 5.84 (d, 2H, J=10.5 Hz), 4.21 (t, 4H, J=6.5 Hz), 4.11 (t, 4H, J=6.5 Hz), 3.65 (s, 3H), 1.86-1.91 (m, 4H), 1.73-1.78 (m, 4H), 1.47-1.61 (m, 8H).

Example 51

Synthesis of Compound 24

Step 1: Synthesis of Intermediate e

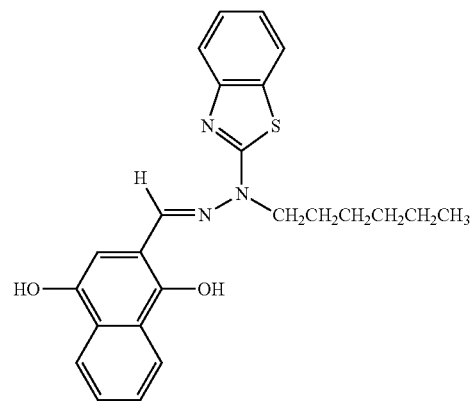

Intermediate e

A four-necked reactor equipped with a thermometer was charged with 808 mg (4.29 mmol) of 1,4-dihydroxynaphthalene-2-carboxaldehyde, 1.53 g (6.13 mmol) of the intermediate H synthesized in Example 9, and 10 ml of 2-propanol under a nitrogen stream. The mixture was refluxed for 3 hours. After completion of the reaction, the reaction mixture was cooled to 20° C., and a solid that had precipitated was filtered off. The solid was washed with 1-propanol, and dried using a vacuum dryer to obtain 1.31 g of an intermediate e as a yellow solid (yield: 72.6%).

The structure of the target product was identified by $^1$H-NMR.

$^1$H-NMR (400 MHz, DMSO-$d_6$, TMS, δ ppm): 9.83 (s, 1H), 9.71 (s, 1H), 8.39 (s, 1H), 8.17-8.20 (m, 1H), 8.04-8.07 (m, 1H), 7.83 (d, 1H, J=8.3 Hz), 7.58 (d, 1H, J=8.3 Hz), 7.47-7.52 (m, 2H), 7.31 (dd, 1H, J=7.4 Hz, 8.3 Hz), 7.19 (s, 1H), 7.14 (dd, 1H, J=7.4 Hz, 8.3 Hz), 4.36 (t, 2H, J=7.3 Hz), 1.66-1.73 (m, 2H), 1.21-1.41 (m, 6H), 0.83 (t, 3H, J=7.1 Hz).

Step 2: Synthesis of Compound 24

A four-necked reactor equipped with a thermometer was charged with 1.00 g (2.38 mmol) of the intermediate e synthesized by the step 1, 1.74 g (5.96 mmol) of 4-(6-acryloyl-hex-1-yloxy)benzoic acid (manufactured by DKSH Japan K.K.), 145 mg (1.19 mmol) of 4-(dimethylamino)pyridine, and 15 ml of N-methylpyrrolidone under a nitrogen stream to prepare a homogeneous solution. After the addition of 1.37 g (7.14 mmol) of WSC to the solution, the mixture was stirred at 25° C. for 15 hours. After completion of the reaction, the Compound 24

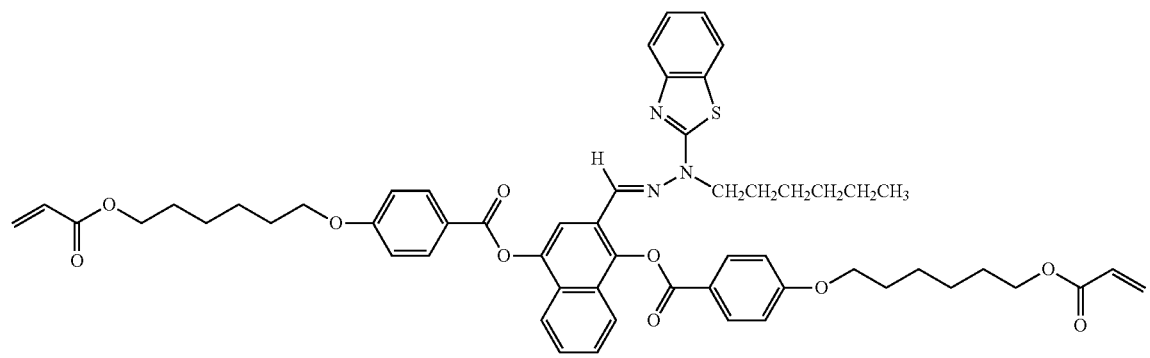

reaction mixture was added to 200 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=90:10 (volume ratio)) to obtain 1.79 g of a compound 24 as a light yellow solid (yield: 77.7%).

The structure of the target product was identified by $^1$H-NMR.

$^1$H-NMR (500 MHz, CDCl$_3$, TMS, δ ppm): 8.333 (d, 2H, J=8.5 Hz), 8.326 (d, 2H, J=8.5 Hz), 8.05 (s, 1H), 7.88-7.94 (m, 3H), 7.63 (dd, 2H, J=1.0 Hz, 8.5 Hz), 7.51-7.54 (m, 2H), 7.31 (ddd, 1H, J=1.0 Hz, 7.5 Hz, 8.5 Hz), 7.12 (ddd, 1H, J=1.0 Hz, 7.5 Hz, 8.5 Hz), 7.07 (d, 4H, J=8.5 Hz), 6.42 (dd, 2H, J=1.5 Hz, 17.5 Hz), 6.14 (dd, 2H, J=10.5 Hz, 17.5 Hz), 5.84 (dd, 2H, J=1.5 Hz, 10.5 Hz), 4.19-4.22 (m, 6H), 4.11 (t, 2H, J=6.5 Hz), 4.10 (t, 2H, J=6.5 Hz), 1.83-1.91 (m, 4H), 1.73-1.78 (m, 4H), 1.47-1.64 (m, 10H), 1.08-1.19 (m, 6H), 0.79 (t, 3H, J=7.0 Hz).

Example 52

Synthesis of Compound 25 hours. After completion of the reaction, the reaction mixture was cooled to 20° C., and a solid that had precipitated was filtered off. The solid was washed with 1-propanol, and dried using a vacuum dryer to obtain 672 mg of an intermediate f as a yellow solid (yield: 40.4%).

The structure of the target product was identified by $^1$H-NMR.

$^1$H-NMR (400 MHz, DMSO-d$_6$, TMS, δ ppm): 10.42 (s, 1H), 9.51 (s, 1H), 8.77 (d, 1H, J=9.6 Hz), 8.68 (s, 1H), 7.85 (d, 1H, J=9.6 Hz), 7.65 (d, 1H, J=9.2 Hz), 7.58 (d, 1H, J=7.8 Hz), 7.31 (dd, 1H, J=7.6 Hz, 7.8 Hz), 7.11-7.16 (m, 3H), 7.08 (d, 1H, J=7.3 Hz), 4.44 (t, 2H, J=7.3 Hz), 1.68-1.76 (m, 2H), 1.21-1.42 (m, 6H), 0.82 (t, 3H, J=7.4 Hz).

Step 2: Synthesis of Compound 25

A four-necked reactor equipped with a thermometer was charged with 672 mg (1.60 mmol) of the intermediate f synthesized by the step 1, 1.17 g (4.01 mmol) of 4-(6-acryloyl-hex-1-yloxy)benzoic acid (manufactured by DKSH Japan K.K.), 97.8 mg (0.801 mmol) of 4-(dimethylamino)pyridine, and 15 ml of N-methylpyrrolidone under a nitrogen stream to prepare a homogeneous solution. After the addition of 921 mg (4.80 mmol) of WSC to the solution, the mixture was stirred at 25° C. for 16 hours. After completion of the reaction, the reaction mixture was added to 200 ml of water, and extracted Compound 25

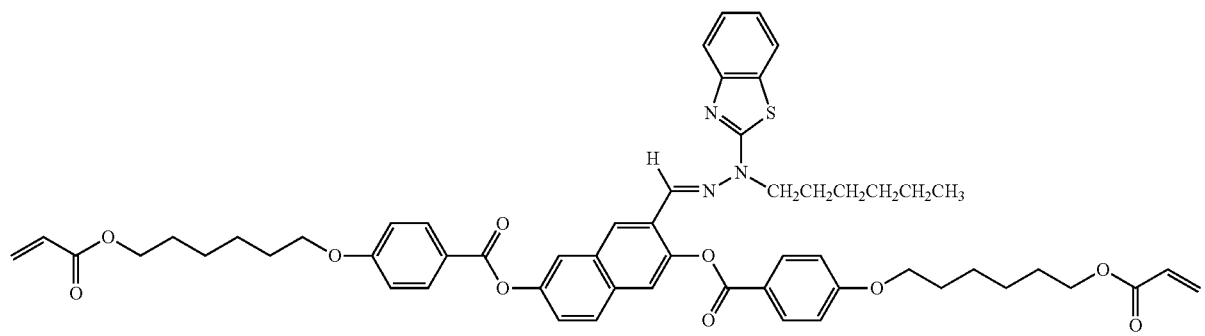

Step 1: Synthesis of Intermediate f

Intermediate f

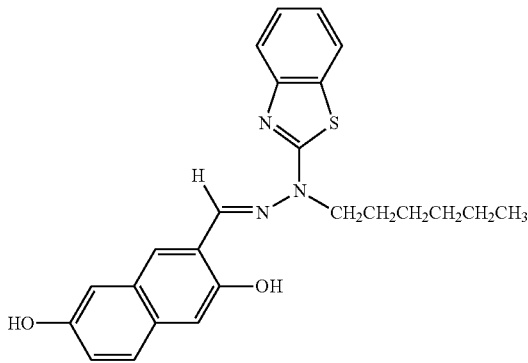

A four-necked reactor equipped with a thermometer was charged with 744 mg (3.69 mmol) of 2,6-dihydroxynaphthalene-1-carboxaldehyde, 2.84 g (7.89 mmol) of the intermediate H synthesized in Example 9, and 10 ml of 2-propanol under a nitrogen stream. The mixture was refluxed for 4 with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=90:10 (volume ratio)) to obtain 1.16 g of a compound 25 as a light yellow solid (yield: 40.0%).

The structure of the target product was identified by $^1$H-NMR.

$^1$H-NMR (500 MHz, CDCl$_3$, TMS, δ ppm): 9.39 (d, 1H, J=9.5 Hz), 8.20-8.24 (m, 5H), 7.89 (d, 1H, J=9.0 Hz), 7.77 (d, 1H, J=2.0 Hz), 7.67 (dd, 1H, J=1.0 Hz, 8.0 Hz), 7.65 (dd, 1H, J=1.0 Hz, 8.0 Hz), 7.62 (dd, 1H, J=2.0 Hz, 9.0 Hz), 7.37 (d, 1H, J=8.5 Hz), 7.32 (ddd, 1H, J=1.0 Hz, 7.5 Hz, 8.0 Hz), 7.15 (ddd, 1H, J=1.0 Hz, 7.5 Hz, 8.0 Hz), 7.01 (d, 4H, J=9.0 Hz), 6.42 (dd, 2H, J=1.0 Hz, 17.0 Hz), 6.14 (dd, 2H, J=10.5 Hz, 17.0 Hz), 5.83 (dd, 2H, J=1.0 Hz, 10.5 Hz), 4.26 (t, 2H, J=7.5 Hz), 4.19 (t, 4H, J=7.0 Hz), 4.08 (t, 2H, J=6.5 Hz), 4.06 (t, 2H, J=6.5 Hz) 1.83-1.89 (m, 4H), 1.71-1.77 (m, 4H), 1.61-1.67 (m, 2H), 1.45-1.57 (m, 8H), 1.02-1.20 (m, 6H), 0.79 (t, 3H, J=7.0 Hz).

Example 53

Synthesis of Compound 26

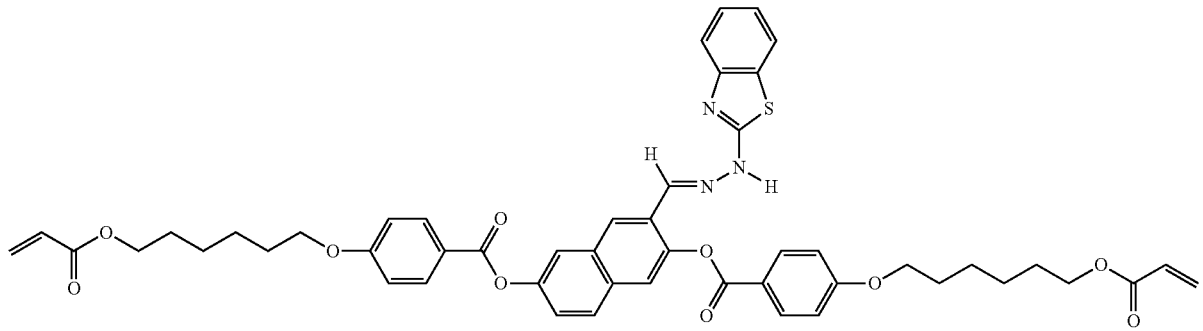

Compound 26

Step 1: Synthesis of Intermediate g

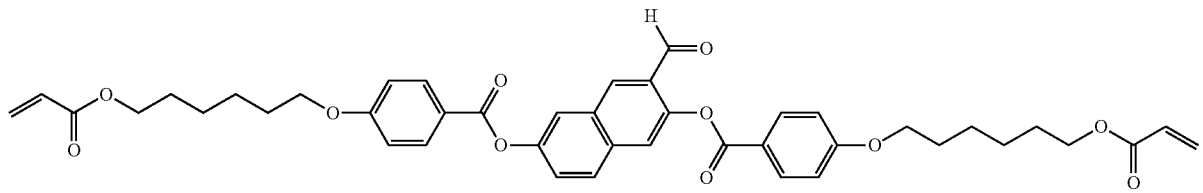

Intermediate g

A four-necked reactor equipped with a thermometer was charged with 1.20 g (6.36 mmol) of 2,6-dihydroxynaphthalene-1-carboxaldehyde, 4.66 g (15.9 mmol) of 4-(6-acryloylhex-1-yloxy)benzoic acid (manufactured by DKSH Japan K.K.), 388 mg (3.18 mmol) of 4-(dimethylamino)pyridine, and 30 ml of N-methylpyrrolidone under a nitrogen stream to prepare a homogeneous solution. After the addition of 3.66 g (19.1 mmol) of WSC to the solution, the mixture was stirred at 25° C. for 8 hours. After completion of the reaction, the reaction mixture was added to 300 ml of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=90:10 (volume ratio)) to obtain 3.00 g of an intermediate g as a yellow solid (yield: 64.2%).

The structure of the target product was identified by $^{1}$H-NMR.

$^{1}$H-NMR (400 MHz, DMSO-d$_{6}$, TMS, δ ppm): 10.74 (s, 1H), 9.34 (d, 1H, J=9.0 Hz), 8.20 (d, 2H, J=9.0 Hz), 8.19 (d, 2H, J=9.0 Hz), 8.09 (d, 1H, J=9.0 Hz), 7.76 (d, 1H, J=2.5 Hz), 7.55 (dd, 1H, J=2.5 Hz, 9.0 Hz), 7.42 (d, 1H, J=9.0 Hz), 7.01 (d, 2H, J=9.0 Hz), 6.99 (d, 2H, J=9.0 Hz), 6.41 (dd, 2H, J=1.0 Hz, 17.5 Hz), 6.13 (dd, 2H, J=10.5 Hz, 17.5 Hz), 5.82 (dd, 2H, J=1.0 Hz, 10.5 Hz), 4.19 (t, 4H, J=6.5 Hz), 4.06 (t, 2H, J=6.5 Hz), 6.05 (t, 2H, J=6.5 Hz), 1.78-1.87 (m, 4H), 1.69-1.76 (m, 4H), 1.44-1.57 (m, 8H).

Step 2: Synthesis of Compound 26

A four-necked reactor equipped with a thermometer was charged with 3.00 g (4.08 mmol) of the intermediate g synthesized by the step 1, 672 mg (4.08 mmol) of 2-hydrazinobenzothiazole, 10 ml of THF, and 10 ml of ethanol under a nitrogen stream. The mixture was stirred at 50° C. for 7 hours. After completion of the reaction, the reaction mixture was added to 200 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=95:5 (volume ratio)) to obtain 1.94 g of a compound 26 as a yellow solid (yield: 66.6%). The structure of the target product was identified by $^{1}$H-NMR.

$^{1}$H-NMR (500 MHz, DMSO-d$_{6}$, TMS, δ ppm): 12.52 (brs, 1H), 9.24 (d, 1H, J=9.0 Hz), 8.69 (s, 1H), 8.18 (d, 2H, J=8.5 Hz), 8.15 (d, 2H, J=8.5 Hz), 8.09 (d, 1H, J=9.0 Hz), 7.99 (d, 1H, J=2.5 Hz), 7.76 (d, 1H, J=6.0 Hz), 7.68 (dd, 1H, J=2.5 Hz, 9.0 Hz), 7.56 (d, 1H, J=9.0 Hz), 7.45 (brs, 1H), 7.30 (dd, 1H, J=7.0 Hz, 7.5 Hz), 7.10-7.19 (m, 5H), 6.33 (dd, 2H, J=1.0 Hz, 17.5 Hz), 6.18 (dd, 2H, J=10.5 Hz, 17.5 Hz), 5.94 (dd, 2H, J=1.0 Hz, 10.5 Hz), 4.10-4.14 (m, 8H), 1.75-1.79 (m, 4H), 1.63-1.68 (m, 4H), 1.38-1.49 (m, 8H).

Example 54

Synthesis of Compound 27

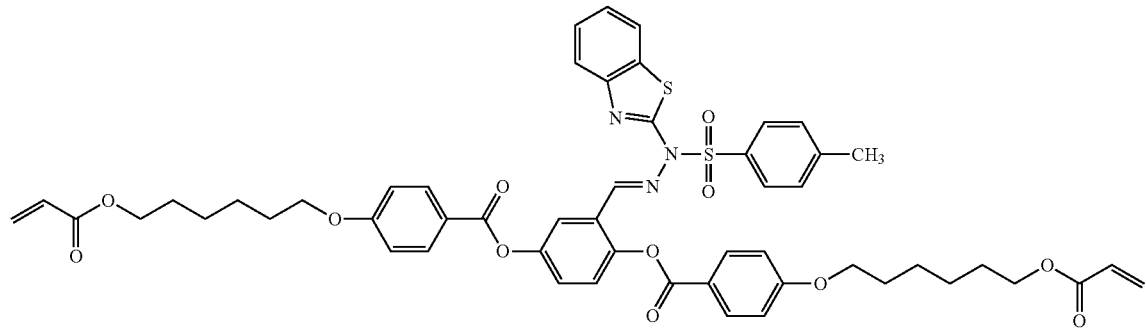

Compound 27

A four-necked reactor equipped with a thermometer was charged with 2.0 g (2.40 mmol) of the compound 1 synthesized in Example 1, 0.5 g (2.62 mmol) of p-toluenesulfonyl chloride, and 40 ml of THF under a nitrogen stream to prepare a homogeneous solution. 620 mg (4.80 mmol) of N,N-diisopropylethylamine that was dissolved in 10 ml of THF was slowly added dropwise to the solution, followed by the addition of 586 mg (4.80 mmol) of 4-(dimethylamino)pyridine. The mixture was stirred at 50° C. for 3 hours. After completion of the reaction, the reaction mixture was added to 500 ml of a 0.05 N hydrochloric acid aqueous solution, and extracted twice with 200 ml of ethyl acetate. The ethyl acetate layer was collected, and dried over anhydrous sodium sulfate, and sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=95:5 to 90:10 (gradient) (volume ratio)) to obtain 1.48 g of a compound 27 as a light yellow solid (yield: 62.4%).

The structure of the target product was identified by $^1$H-NMR.

$^1$H-NMR (500 MHz, CDCl$_3$, TMS, δ ppm): 8.72 (s, 1H), 8.19 (d, 2H, J=9.0 Hz), 8.00 (d, 2H, J=9.0 Hz), 7.89 (d, 1H, J=2.5 Hz), 7.85 (d, 1H, J=8.0 Hz), 7.74 (d, 2H, J=8.5 Hz), 7.69 (dd, 1H, J=0.5 Hz, 8.0 Hz), 7.41-7.38 (m, 3H), 7.31 (dd, 1H, J=1.0 Hz, 8.0 Hz), 7.22 (d, 2H, J=8.5 Hz), 7.01 (d, 2H, J=9.0 Hz), 6.82 (d, 2H, J=9.0 Hz), 6.41 (dd, 2H, J=1.0 Hz, 17.5 Hz), 6.13 (dd, 2H, J=10.5 Hz, 17.5 Hz), 5.831 (dd, 1H, J=1.0 Hz, 10.5 Hz), 5.829 (dd, 1H, J=1.0 Hz, 10.5 Hz), 4.198 (t, 2H, J=6.5 Hz), 4.194 (t, 2H, J=6.5 Hz), 4.08 (t, 2H, 6.5 Hz), 4.02 (t, 2H, J=6.5 Hz), 2.36 (s, 3H), 1.89-1.83 (m, 4H), 1.77-1.71 (m, 4H), 1.59-1.45 (m, 8H).

Example 55

Synthesis of Compound 28

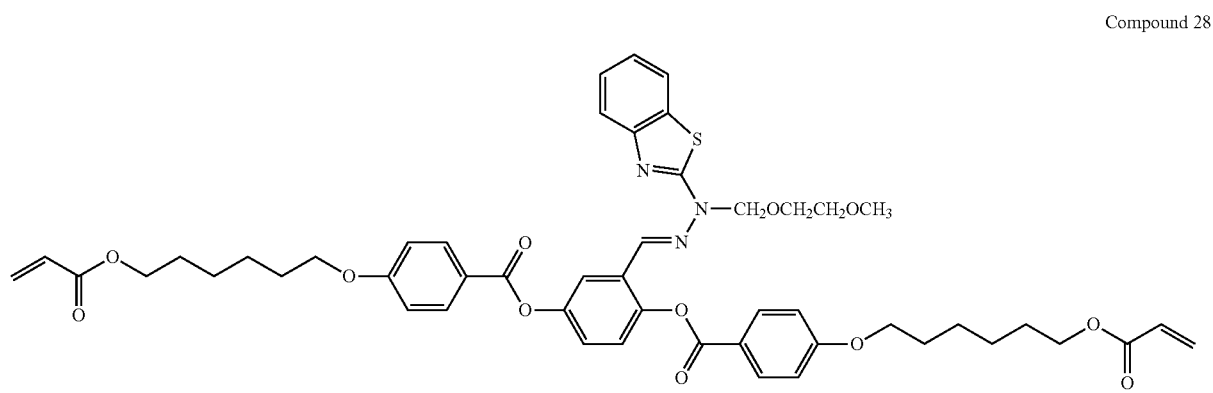

Compound 28

A four-necked reactor equipped with a thermometer was charged with 2.0 g (2.40 mmol) of the compound 1 synthesized in Example 1, 448 mg (3.60 mmol) of 2-methoxyethoxymethyl chloride, and 40 ml of THF under a nitrogen stream to prepare a homogeneous solution. 620 mg (4.80 mmol) of N,N-diisopropylethylamine that was dissolved in 10 ml of THF was slowly added dropwise to the solution at 23° C. The mixture was stirred at 23° C. for 2 hours. After completion of the reaction, the reaction mixture was added to 500 ml of water, and extracted twice with 200 ml of ethyl acetate. The ethyl acetate layer was collected, and dried over anhydrous sodium sulfate, and sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=90:10 to 85:15 (gradient) (volume ratio)) to obtain 1.1 g of a compound 28 as a light yellow solid (yield: 49.7%).

The structure of the target product was identified by ¹H-NMR.

¹H-NMR (500 MHz, CDCl₃, TMS, δ ppm): 8.44 (s, 1H), 8.205 (d, 2H, J=7.0 Hz), 8.187 (d, 2H, J=7.0 Hz), 7.98 (d, 1H, J=3.0 Hz), 7.35 (d, 1H, J=7.5 Hz), 7.29-7.22 (m, 4H), 7.08-7.05 (m, 1H), 7.013 (d, 2H, J=7.0 Hz), 6.995 (d, 2H, J=7.0 Hz), 6.41 (dd, 2H, J=1.5 Hz, 17.5 Hz), 6.14 (dd, 2H, J=10.5 Hz, 17.5 Hz), 5.83 (dd, 2H, J=1.5 Hz, 10.5 Hz), 5.59 (s, 2H), 4.19 (t, 4H, J=6.5 Hz), 4.08 (t, 2H, J=6.5 Hz), 4.07 (t, 2H, J=6.5 Hz), 3.75-3.73 (m, 2H), 3.50-3.48 (m, 2H), 3.32 (s, 3H), 1.89-1.84 (m, 4H), 1.78-1.71 (m, 4H), 1.59-1.46 (m, 8H).

Example 56

Synthesis of Compound 29

Phase Transition Temperature Measurement 2

The phase transition temperature of the compounds 21 to 29 was measured in the same manner as in the section "Phase transition temperature measurement 1", except that the substrates were heated from 40° C. to 200° C., and cooled to 40° C. instead of heating the substrates from 50° C. to 200° C., and cooling the substrates to 50° C.

The phase transition temperature measurement results are shown in Table 4.

TABLE 4

| | Polymerizable compound | Phase transition temperature |
|---|---|---|
| Example 48 | Compound 21 | C ⇌ I (134° C. / 95° C.) |

Compound 29

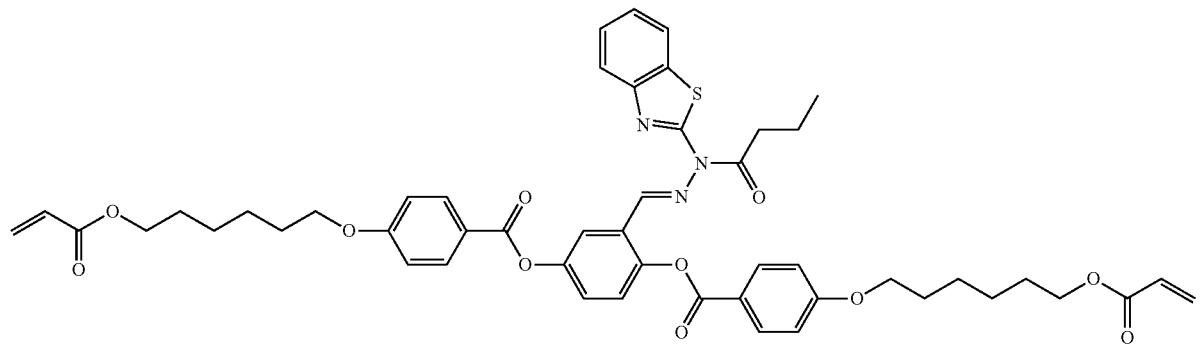

A four-necked reactor equipped with a thermometer was charged with 4.0 g (4.80 mmol) of the compound 1 synthesized in Example 1, 767 mg (7.20 mmol) of butyryl chloride, and 50 ml of THF under a nitrogen stream to prepare a solution. 1.24 g (9.60 mmol) of N,N-diisopropylethylamine that was dissolved in 20 ml of THF was slowly added dropwise to the solution at 23° C. The mixture was stirred at 23° C. for 2 hours. After completion of the reaction, the reaction mixture was added to 500 ml of a 0.05 N hydrochloric acid aqueous solution, and extracted twice with 200 ml of ethyl acetate. The ethyl acetate layer was collected, and dried over anhydrous sodium sulfate, and sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=95:5 (volume ratio)) to obtain 1.0 g of a compound 29 as a light yellow solid (yield: 23.0%).

The structure of the target product was identified by ¹H-NMR.

¹H-NMR (500 MHz, CDCl₃, TMS, δ ppm): 8.53 (s, 1H), 8.27 (d, 1H, J=8.0 Hz), 8.21-8.18 (m, 4H), 7.99 (d, 1H, J=3.0 Hz), 7.35-7.21 (m, 4H), 7.15 (dd, 1H, J=1.5 Hz, 7.5 Hz), 7.01-6.99 (m, 4H), 6.412 (dd, 1H, J=1.5 Hz, 17.5 Hz), 6.409 (dd, 1H, J=1.5 Hz, 17.5 Hz), 6.133 (dd, 1H, J=10.5 Hz, 17.5 Hz), 6.131 (dd, 1H, J=10.5 Hz, 17.5 Hz), 5.83 (dd, 2H, J=1.5 Hz, 10.5 Hz), 4.189 (t, 2H, J=6.5 Hz), 4.188 (t, 2H, J=6.5 Hz), 4.066 (t, 2H, J=6.5 Hz), 4.062 (t, 2H, J=6.5 Hz), 3.22 (t, 2H, J=7.0 Hz), 1.88-1.71 (m, 10H), 1.58-1.45 (m, 8H), 0.94 (t, 3H, J=7.5 Hz).

TABLE 4-continued

| | Polymerizable compound | Phase transition temperature |
|---|---|---|
| Example 49 | Compound 22 | C ⇌ I (184° C. / 105° C.) |
| Example 50 | Compound 23 | C ⇌ I (160° C. / 120° C.) |
| Example 51 | Compound 24 | C ⇌ I (112° C. / 53° C.) |
| Example 52 | Compound 25 | C ⇌ N (112° C. / 40° C. or less) N ⇌ I (117° C. / 113° C.) |
| Example 53 | Compound 26 | C ⇌ N (152° C. / 40° C. or less) N ⇌ I (186° C. / 168° C.) |
| Example 54 | Compound 27 | C ⇌ I (93° C. / 58° C.) |
| Example 55 | Compound 28 | C ⇌ N (73° C. / 40° C. or less) N ⇌ I (43° C.) |

TABLE 4-continued

| | Polymerizable compound | Phase transition temperature |
|---|---|---|
| Example 56 | Compound 29 | C $\xrightleftharpoons[75°C.]{93°C.}$ N $\xrightleftharpoons{95°C.}$ I |

Example 57

0.2 g of the compound 21 obtained in Example 48, 0.8 g of the compound 1 obtained in Example 1, 30 mg of Adekaoptomer N-1919 (photoinitiator), and 100 mg of a 1% cyclopentanone solution of KH-40 (surfactant) were dissolved in 2.3 g of cyclopentanone. The solution was filtered through a disposable filter having a pore size of 0.45 μm to obtain a polymerizable composition (polymerizable composition 28).

Examples 58 to 61

0.5 g of the corresponding compound among the compounds 22 to 24 and 27 obtained in Examples 49 to 51 and 54, 0.5 g of the compound 1 obtained in Example 1, 30 mg of Adekaoptomer N-1919 (photoinitiator), and 100 mg of a 1% cyclopentanone solution of KH-40 (surfactant) were dissolved in 2.3 g of cyclopentanone. The solution was filtered through a disposable filter having a pore size of 0.45 μm to obtain a polymerizable composition (polymerizable compositions 29 to 32).

Examples 62 to 67

1.0 g of the corresponding compound among the compounds 52, 55, 53, 56, 19, and 11 obtained in Examples 25, 28, 26, 29, 19 and 11, 30 mg of Adekaoptomer N-1919 (photoinitiator), and 100 mg of a 1% cyclopentanone solution of KH-40 (surfactant) were dissolved in 2.3 g of cyclopentanone. The solution was filtered through a disposable filter having a pore size of 0.45 μm to obtain a polymerizable composition (polymerizable compositions 33 to 38).

Measurement 2 of Retardation and Evaluation 2 of Wavelength Dispersion

The retardation was measured, and the wavelength dispersion was evaluated using the polymerizable compositions 28 to 34 in the same manner as in the section "Measurement 1 of retardation and evaluation 1 of wavelength dispersion". The drying temperature, the alignment temperature, the thickness, the retardation (Re), and the values α and β are shown in Table 5.

Measurement 3 of Retardation and Evaluation 3 of Wavelength Dispersion

The retardation was measured, and the wavelength dispersion was evaluated using the polymerizable composition 35 in the same manner as in the section "Measurement 1 of retardation and evaluation 1 of wavelength dispersion", except that a transparent glass substrate provided with a polyimide alignment film subjected to a rubbing treatment (manufactured by E.H.C. Co. Ltd.) was used instead of the transparent resin substrate on which the alignment film was formed. The drying temperature, the alignment temperature, the thickness, the retardation (Re), and the values α and β are shown in Table 5.

Measurement 4 of Retardation and Evaluation 4 of Wavelength Dispersion

The retardation was measured, and the wavelength dispersion was evaluated using the polymerizable compositions 36 to 38 in the same manner as in the section "Measurement 1 of retardation and evaluation 1 of wavelength dispersion", except that the alignment treatment was performed for 1 minute at the temperature shown in Table 5, and UV rays were applied to the liquid crystal layer at a dose of 2000 mJ/cm$^2$ while maintaining the temperature shown in Table 5 to effect polymerization. The drying temperature, the alignment temperature, the thickness, the retardation (Re), and the values α and β are shown in Table 5.

TABLE 5

| | Polymerizable composition | Polymerizable compound 1 | | Polymerizable compound 2 | | Drying temperature (°C.) | Alignment temperature (°C.) | Film thickness (μm) | Re (548.5 nm) | α | β |
|---|---|---|---|---|---|---|---|---|---|---|---|
| | | Compound | Content (%) | Compound | Content (%) | | | | | | |
| Example 57 | 28 | Compound 21 | 20 | Compound 1 | 80 | 100 | 23 | 1.605 | 140.74 | 0.901 | 1.000 |
| Example 58 | 29 | Compound 22 | 50 | Compound 1 | 50 | 120 | 23 | 1.750 | 125.05 | 0.775 | 1.051 |
| Example 59 | 30 | Compound 23 | 50 | Compound 1 | 50 | 100 | 23 | 1.528 | 128.50 | 0.842 | 1.028 |
| Example 60 | 31 | Compound 24 | 50 | Compound 1 | 50 | 120 | 23 | 1.550 | 115.55 | 0.828 | 1.042 |
| Example 61 | 32 | Compound 27 | 50 | Compound 1 | 50 | 100 | 23 | 1.600 | 163.44 | 1.023 | 0.998 |
| Example 62 | 33 | Compound 25 | 100 | — | — | 120 | 23 | 1.656 | 166.90 | 0.808 | 0.988 |
| Example 63 | 34 | Compound 28 | 100 | — | — | 100 | 35 | 1.492 | 125.21 | 0.913 | 1.007 |
| Example 64 | 35 | Compound 26 | 100 | — | — | 195 | 23 | 1.386 | 151.10 | 0.840 | 0.999 |
| Example 65 | 36 | Compound 29 | 100 | — | — | 110 | 85 | 1.520 | 92.55 | 1.013 | 0.993 |
| Example 66 | 37 | Compound 19 | 100 | — | — | 120 | 83 | 1.514 | 142.65 | 0.915 | 1.011 |
| Example 67 | 38 | Compound 11 | 100 | — | — | 170 | 125 | 1.353 | 142.53 | 0.986 | 0.988 |

As is clear from the results shown in Table 5, it was confirmed that optically anisotropic articles (polymers) were obtained in Examples 57 to 67. The values α and β were almost identical when using the optically anisotropic articles obtained in Examples 57 to 67. The optically anisotropic articles obtained in Examples 57 to 60, 63, and 66 are particularly preferable since the value α was smaller than 1, and the value β was larger than 1.

Example 68

Synthesis of Compound 30

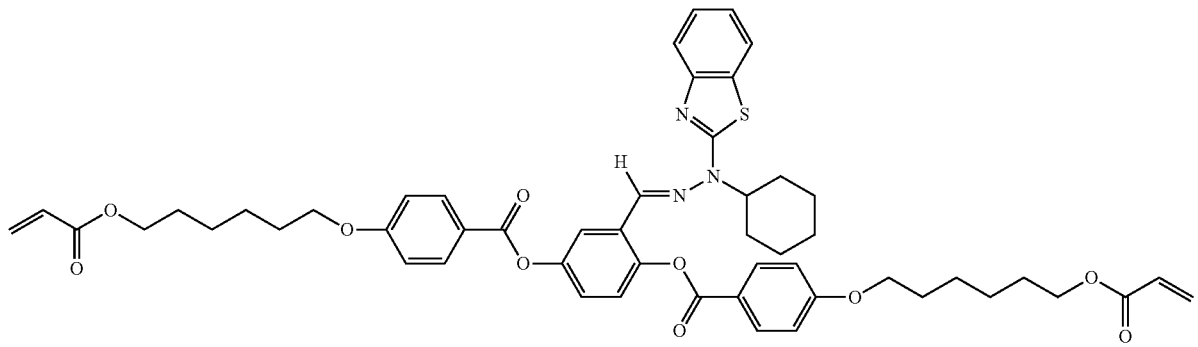

Compound 30

Step 1: Synthesis of Intermediate h

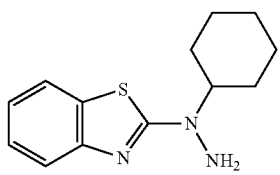

Intermediate h

A four-necked reactor equipped with a thermometer was charged with 2.50 g (16.6 mmol) of cyclohexylhydrazine hydrochloride and 8 ml of triethylamine under a nitrogen stream to prepare a homogeneous solution. After the addition of 5.63 g (33.2 mmol) of 2-chlorobenzothiazole to the solution, the mixture was stirred at 80° C. for 5 hours. After completion of the reaction, the reaction mixture was cooled to 20° C., added to 150 ml of a saturated sodium hydrogen carbonate aqueous solution, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=75:25 (volume ratio)) to obtain 1.02 g of an intermediate h as a white solid (yield: 22.3%).

The structure of the target product was identified by $^1$H-NMR.

$^1$H-NMR (400 MHz, CDCl$_3$, TMS, δ ppm): 7.58 (d, 1H, J=7.8 Hz), 7.52 (d, 1H, J=8.2 Hz), 7.26 (dd, 1H, J=7.4 Hz, 8.2 Hz), 7.05 (dd, 1H, J=7.4 Hz, 7.8 Hz), 4.25-4.32 (m, 1H), 4.04 (s, 2H), 1.84-1.88 (m, 4H), 1.68-1.73 (m, 1H), 1.43-1.59 (m, 4H), 1.08-1.19 (m, 1H).

Step 2: Synthesis of Intermediate i

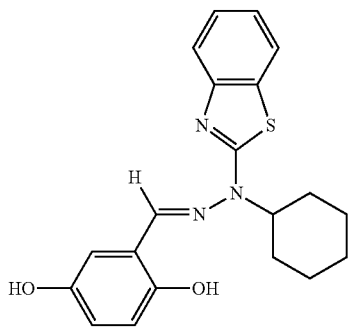

Intermediate i

A four-necked reactor equipped with a thermometer was charged with 510 mg (3.69 mmol) of 2,5-dihydroxybenzaldehyde, 1.02 g (3.69 mmol) of the intermediate h synthesized by the step 1, and 10 ml of 2-propanol under a nitrogen stream to prepare a homogeneous solution. The solution was stirred at 80° C. for 3 hours. After completion of the reaction, the reaction mixture was cooled to 20° C., and a solid that had precipitated was filtered off. The solid was washed with 2-propanol, and dried using a vacuum dryer to obtain 685 mg of an intermediate i as a white solid (yield: 46.9%).

The structure of the target product was identified by $^1$H-NMR.

$^1$H-NMR (400 MHz, DMSO-d$_6$, TMS, δ ppm): 9.38 (s, 1H), 8.93 (s, 1H), 8.37 (s, 1H), 7.77 (d, 1H, J=7.3 Hz), 7.56 (d, 1H, J=7.8 Hz), 7.28 (dd, 1H, J=7.8 Hz, 7.8 Hz), 7.15 (d, 1H, J=2.8 Hz), 7.11 (dd, 1H, J=7.3 Hz, 7.8 Hz), 6.72 (d, 1H, J=8.7 Hz), 6.67 (dd, 1H, J=2.8 Hz, 8.7 Hz), 4.58 (tt, 1H, J=3.7 Hz, 11.9 Hz), 2.36-2.45 (m, 2H), 1.76-1.86 (m, 4H), 1.65-1.68 (m, 1H), 1.38-1.48 (m, 2H), 1.16-1.25 (m, 1H).

Step 3: Synthesis of Compound 30

A four-necked reactor equipped with a thermometer was charged with 85 mg (1.73 mmol) of the intermediate i synthesized by the step 2, 1.27 g (4.33 mmol) of 4-(6-acryloyl-hex-1-yloxy)benzoic acid (manufactured by DKSH Japan K.K.), 106 mg (0.865 mmol) of 4-(dimethylamino)pyridine, and 10 ml of N-methylpyrrolidone under a nitrogen stream to prepare a homogeneous solution. After the addition of 995 mg (5.19 mmol) of WSC to the solution, the mixture was stirred at 25° C. for 18 hours. After completion of the reaction, the reaction mixture was added to 100 ml of water, and extracted with 200 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a white solid. The white solid was purified by silica gel column chromatography (toluene:ethyl acetate=90:10 (volume ratio)) to obtain 1.17 g of a compound 30 as a white solid (yield: 73.8%).

The structure of the target product was identified by $^1$H-NMR.

$^1$H-NMR (500 MHz, CDCl$_3$, TMS, δ ppm): 8.28 (s, 1H), 8.21 (d, 2H, J=9.0 Hz), 8.20 (d, 2H, J=9.0 Hz), 7.87 (d, 1H, J=2.5 Hz), 7.62 (d, 1H, J=7.5 Hz), 7.56 (d, 1H, J=8.0 Hz), 7.31 (d, 1H, J=8.5 Hz), 7.25-7.29 (m, 2H), 7.11 (dd, 1H, J=7.5 Hz, 8.0 Hz), 7.012 (d, 2H, J=9.0 Hz), 7.008 (d, 2H, J=9.0 Hz), 6.41 (dd, 2H, J=1.5 Hz, 17.5 Hz), 6.13 (dd, 2H, J=10.5 Hz, 17.5 Hz), 5.83 (dd, 2H, J=1.5 Hz, 10.5 Hz), 4.74 (tt, 1H, J=4.0 Hz, 12.5 Hz), 4.19 (t, 4H, J=7.0 Hz), 4.08 (t, 2H, J=6.5 Hz), 4.07 (t, 2H, J=6.5 Hz), 2.14-2.22 (m, 2H), 1.84-1.89 (m, 6H), 1.71-1.77 (m, 6H), 1.44-1.59 (m, 9H), 1.26-1.34 (m, 2H), 0.72-0.80 (m, 1H).

Example 69

Synthesis of Compound 31

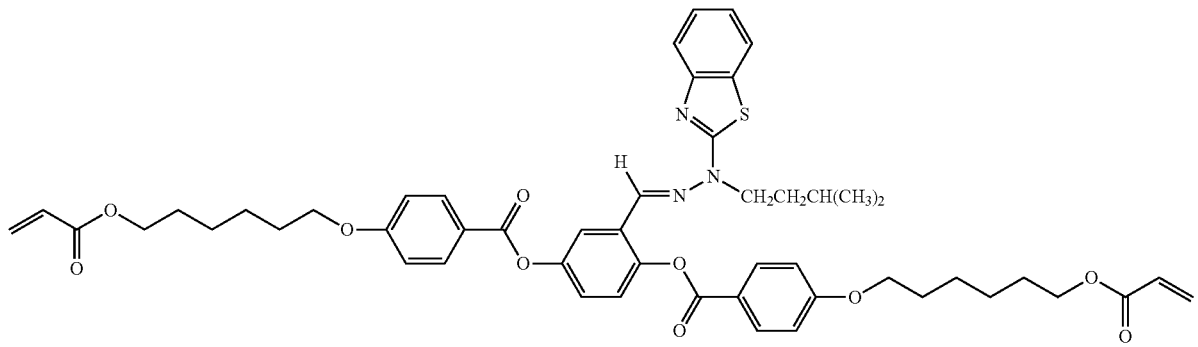

Compound 31

Step 1: Synthesis of Intermediate j

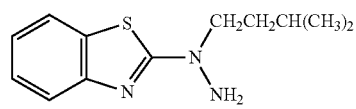

Intermediate j

A four-necked reactor equipped with a thermometer was charged with 3.00 g (18.2 mmol) of 2-hydrazinobenzothiazole and 20 ml of THF under a nitrogen stream to prepare a homogeneous solution. 11.4 ml (18.2 mmol) of lithium hexamethyldisilazane (26% THF solution) was slowly added dropwise to the solution at 0° C., and the mixture was stirred at 0° C. for 30 minutes. After the addition of 2.9 ml (21.8 mmol) of 1-iodo-3-methylbutane to the solution, the mixture was stirred at 25° C. for 6 hours. After completion of the reaction, the reaction mixture was added to 100 ml of water, and extracted with 150 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=75:25 (volume ratio)) to obtain 2.07 g of an intermediate j as a white solid (yield: 48.2%).

The structure of the target product was identified by $^1$H-NMR.

$^1$H-NMR (500 MHz, CDCl$_3$, TMS, δ ppm): 7.59 (d, 1H, J=8.5 Hz), 7.53 (d, 1H, J=8.0 Hz), 7.27 (dd, 1H, J=7.8 Hz, 8.0 Hz), 7.06 (dd, 1H, J=7.8 Hz, 8.5 Hz), 4.21 (s, 2H), 3.75 (t, 2H, J=7.5 Hz), 1.63-1.70 (m, 1H), 1.60 (dt, 2H, J=7.0 Hz, 7.5 Hz), 0.97 (d, 6H, J=6.5 Hz).

Step 2: Synthesis of Intermediate k

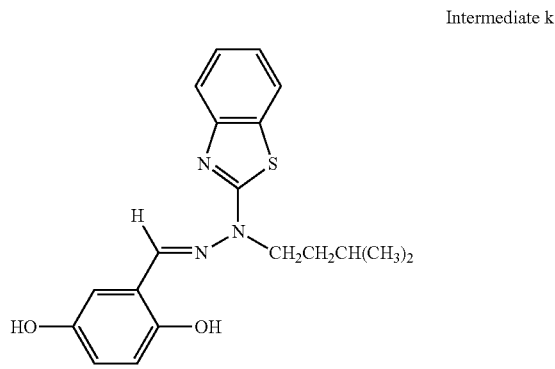

Intermediate k

A four-necked reactor equipped with a thermometer was charged with 1.21 g (8.78 mmol) of 2,5-dihydroxybenzaldehyde, 2.07 g (8.78 mmol) of the intermediate j synthesized by the step 1, and 15 ml of 2-propanol under a nitrogen stream to prepare a homogenous solution. The solution was stirred at 80° C. for 1.5 hours. After completion of the reaction, the reaction mixture was cooled to 20° C., and a solid that had precipitated was filtered off. The solid was washed with 2-propanol, and dried using a vacuum dryer to obtain 1.36 g of an intermediate k as a white solid (yield: 43.6%).

The structure of the target product was identified by $^1$H-NMR.

$^1$H-NMR (500 MHz, DMSO-d$_6$, TMS, δ ppm): 9.38 (s, 1H), 8.97 (s, 1H), 8.12 (s, 1H), 7.83 (d, 1H, J=8.0 Hz), 7.59 (d, 1H, J=8.0 Hz), 7.33 (dd, 1H, J=7.5 Hz, 8.0 Hz), 7.18 (d, 1H, J=3.0 Hz), 7.16 (dd, 1H, J=7.5 Hz, 8.0 Hz), 6.75 (d, 1H, J=9.0 Hz), 6.70 (dd, 1H, J=3.0 Hz, 9.0 Hz), 4.34 (t, 2H, J=7.5 Hz), 1.63-1.74 (m, 1H), 1.55 (dt, 2H, J=7.0 Hz, 7.5 Hz), 0.99 (d, 6H, J=6.5 Hz).

Step 3: Synthesis of Compound 31

A four-necked reactor equipped with a thermometer was charged with 1.36 g (3.83 mmol) of the intermediate k synthesized by the step 2, 2.80 g (9.58 mmol) of 4-(6-acryloylhex-1-yloxy)benzoic acid (manufactured by DKSH Japan K.K.), 234 mg (1.92 mmol) of 4-(dimethylamino)pyridine, and 20 ml of N-methylpyrrolidone under a nitrogen stream to prepare a homogeneous solution. After the addition of 2.20 g (11.5 mmol) of WSC to the solution, the mixture was stirred at 25° C. for 5 hours. After completion of the reaction, the reaction mixture was added to 200 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a white solid. The white solid was purified by silica gel column chromatography (toluene:ethyl acetate=90:10 (volume ratio)) to obtain 1.61 g of a compound 31 as a white solid (yield: 46.5%).

The structure of the target product was identified by $^1$H-NMR.

$^1$H-NMR (500 MHz, CDCl$_3$, TMS, δ ppm): 8.21 (d, 2H, J=9.0 Hz), 8.19 (d, 2H, J=9.0 Hz), 7.90 (s, 1H), 7.76 (s, 1H), 7.61-7.64 (m, 2H), 7.30 (dd, 1H, J=7.5 Hz, 8.0 Hz), 7.24-7.27 (m, 2H), 7.12 (dd, 1H, J=7.5 Hz, 8.0 Hz), 7.01 (d, 2H, J=9.0 Hz), 7.00 (d, 2H, J=9.0 Hz), 6.42 (dd, 2H, J=1.5 Hz, 17.5 Hz), 6.14 (dd, 2H, J=10.5 Hz, 17.5 Hz), 5.83 (dd, 2H, J=1.5 Hz, 10.5 Hz), 4.18-4.22 (m, 6H), 4.08 (t, 2H, J=6.5 Hz), 4.07 (t, 2H, J=6.5 Hz), 1.84-1.89 (m, 4H), 1.70-1.77 (m, 4H), 1.48-1.59 (m, 11H), 0.78 (d, 6H, J=6.0 Hz).

Example 70

Synthesis of Compound 32

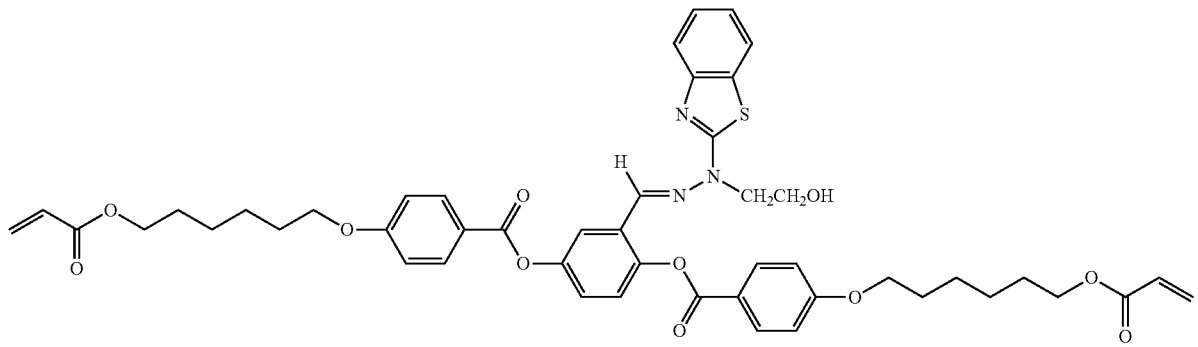

Compound 32

Step 1: Synthesis of Intermediate 1

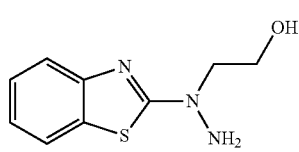

Intermediate 1

A four-necked reactor equipped with a thermometer was charged with 8.00 g (0.11 mol) of 2-hydrazinoethanole and 30 ml of methanol under a nitrogen stream to prepare a homogeneous solution. A solution prepared by dissolving 2.0 g (26.28 mmol) of 2-chlorobenzothiazole in 30 ml of methanol was slowly added to the above solution at 25° C. The mixture was refluxed for 3 hours. After completion of the reaction, the reaction mixture was cooled to 20° C., added to 500 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a white solid. The white solid was recrystallized from ethyl acetate to obtain 0.6 g of an intermediate 1 (yield: 10.9%).

The structure of the target product was identified by $^1$H-NMR.

$^1$H-NMR (500 MHz, DMSO-$d_6$, TMS, δ ppm): 7.66 (dd, 1H, J=1.0 Hz, 8.0 Hz), 7.34 (dd, 1H, J=1.0 Hz, 7.5 Hz), 7.20 (ddd, 1H, J=1.0 Hz, 7.5 Hz, 8.0 Hz), 6.98 (ddd, 1H, J=1.0 Hz, 7.5 Hz, 7.5 Hz), 5.37 (s, 2H), 4.86 (t, 1H, J=5.5 Hz), 3.78 (t, 2H, J=6.5 Hz), 3.72 (dt, 2H, J=6.5 Hz, 5.5 Hz).

Step 2: Synthesis of Compound 32

A four-necked reactor equipped with a thermometer was charged with 1.2 g (1.75 mmol) of the intermediate A synthesized by the step 1 of Example 1, 20 ml of THF, and 0.55 g (2.63 mmol) of the intermediate 1 synthesized by the step 1 under a nitrogen stream to prepare a homogeneous solution. After the addition of 41 mg (0.175 mmol) of (±)-10-camphorsulfonic acid to the solution, the mixture was stirred at 25° C. for 20 hours. After completion of the reaction, the reaction mixture was added to 300 ml of 10% sodium bicarbonate water, and extracted twice with 100 ml of ethyl acetate. The ethyl acetate layer was collected, and dried over anhydrous sodium sulfate, and sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=8:2 (volume ratio)) to obtain 1.0 g of a compound 32 as a white solid (yield: 65.1%).

The structure of the target product was identified by $^1$H-NMR.

$^1$H-NMR (500 MHz, CDCl$_3$, TMS, δ ppm): 8.20-8.17 (m, 4H), 8.07 (s, 1H), 7.88 (d, 1H, J=2.5 Hz), 7.62-7.59 (m, 2H), 7.31-7.26 (m, 3H), 7.15-7.12 (m, 1H), 7.02 (dd, 4H, J=3.0 Hz, 9.0 Hz), 6.41 (dd, 2H, J=1.5 Hz, 17.0 Hz), 6.13 (dd, 2H, J=10.5 Hz, 17.0 Hz), 5.83 (dd, 2H, J=1.5 Hz, 10.5 Hz), 4.35 (t, 2H, J=5.0 Hz), 4.191 (t, 2H, J=6.5 Hz), 4.187 (t, 2H, J=6.5 Hz), 4.07 (t, 2H, J=6.5 Hz), 4.06 (t, 2H, J=6.5 Hz), 3.91 (t, 2H, J=5.0 Hz), 3.05 (s, 1H), 1.89-1.83 (m, 4H), 1.77-1.71 (m, 4H), 1.58-1.48 (m, 8H).

Example 71

Synthesis of Compound 33

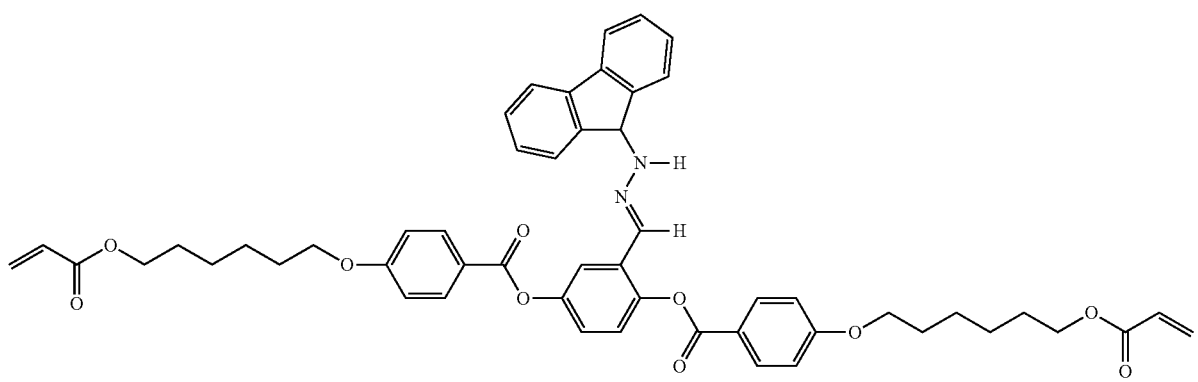

Compound 33

Step 1: Synthesis of Intermediate m

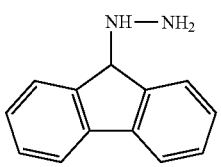

Intermediate m

A four-necked reactor equipped with a thermometer was charged with 8.2 g (0.163 mol) of hydrazine monohydrate and 80 ml of ethanol under a nitrogen stream to prepare a homogeneous solution. After the addition of 8.00 g (32.6 mmol) of 9-bromofluorene to the solution, the mixture was refluxed for 2 hours. After completion of the reaction, the reaction mixture was added to 800 ml of a saturated sodium hydrogen carbonate aqueous solution, and extracted with 300 ml of chloroform. The chloroform layer was washed twice with 300 ml of a saturated sodium hydrogen carbonate aqueous solution, and dried over anhydrous sodium sulfate, and sodium sulfate was filtered off. Chloroform was evaporated from the filtrate under reduced pressure using a rotary evaporator to obtain 7.5 g of a yellow oil including an intermediate m.

The yellow oil was used directly for the subsequent reaction without purification.

Step 2: Synthesis of Compound 33

A four-necked reactor equipped with a thermometer was charged with 4.0 g (5.82 mmol) of the intermediate A synthesized by the step 1 in Example 1 and 80 ml of THF under a nitrogen stream to prepare a homogeneous solution. After the addition of 4.6 g of the yellow oil (including the intermediate m) synthesized by the step 1 to the solution, the mixture was stirred at 25° C. for 2 hours. After completion of the reaction, THF was evaporated from the reaction mixture under reduced pressure using a rotary evaporator to obtain a yellow oil. The yellow oil was purified by silica gel column chromatography (toluene:ethyl acetate=95:5 (volume ratio)), and purified by recycling preparative gel permeation chromatography (recycling preparative GPC) (mobile phase: chloroform) to obtain 1.35 g of a compound 33 as a yellow solid (yield: 26.8%).

The $^1$H-NMR spectrum data of the compound 33 are shown below.

$^1$H-NMR (500 MHz, CDCl$_3$, TMS, δ ppm): 8.17 (d, 2H, J=9.0 Hz), 8.08 (d, 2H, J=9.0 Hz), 7.883-7.877 (m, 1H), 7.66 (s, 1H), 7.62-7.60 (m, 4H), 7.35 (d, 1H, J=7.5 Hz), 7.33 (d, 1H, J=7.5 Hz), 7.26 (dd, 1H, J=7.5 Hz, 1.0 Hz), 7.25 (dd, 1H, J=7.5 Hz, 1.0 Hz), 7.21-7.20 (m, 2H), 6.97 (d, 2H, J=9.0 Hz), 6.89 (d, 2H, J=9.0 Hz), 6.39 (dd, 1H, J=17.5 Hz, 1.5 Hz), 6.37 (dd, 1H, J=17.5 Hz, 1.5 Hz), 6.11 (dd, 1H, J=17.5 Hz, 10.5 Hz), 6.09 (dd, 1H, J=17.5 Hz, 10.5 Hz), 5.80 (dd, 1H, J=10.5 Hz, 1.5 Hz), 5.79 (dd, 1H, J=10.5 Hz, 1.5 Hz), 5.62 (d, 1H, J=9.5 Hz), 5.52 (d, 1H, J=9.5 Hz), 4.17 (t, 2H, J=6.5 Hz), 4.14 (t, 2H, J=6.5 Hz), 4.03 (t, 2H, J=6.5 Hz), 3.96 (t, 2H, J=6.5 Hz), 1.86-1.65 (m, 8H), 1.56-1.40 (m, 8H).

Example 72

Synthesis of Compound 34

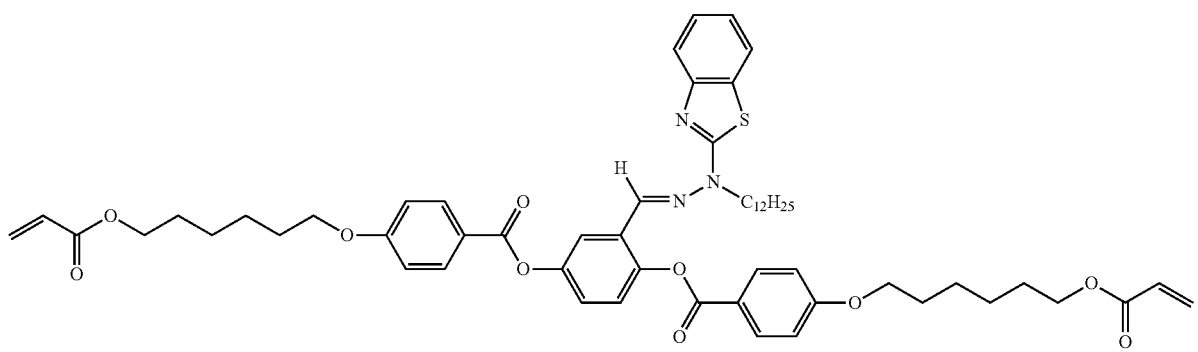

Compound 34

Step 1: Synthesis of Intermediate n

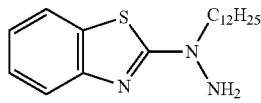

Intermediate n

A four-necked reactor equipped with a thermometer was charged with 3.00 g (18.2 mmol) of 2-hydrazinobenzothiazole and 45 ml of DMF under a nitrogen stream to prepare a homogeneous solution. After the addition of 11.9 g (36.4 mmol) of cesium carbonate and 6.45 g (21.8 mmol) of 1-iododecane to the solution, the mixture was stirred at 25° C. for 20 hours. After completion of the reaction, the reaction mixture was added to 200 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=95:5 (volume ratio)) to obtain 2.93 g of an intermediate n as a white solid (yield: 48.3%).

The structure of the target product was identified by $^1$H-NMR.

The $^1$H-NMR spectrum data of the intermediate n are shown below.

$^1$H-NMR (500 MHz, CDCl$_3$, TMS, δ ppm): 7.60 (dd, 1H, J=1.0 Hz, 8.0 Hz), 7.53 (dd, 1H, J=1.0 Hz, 8.0 Hz), 7.27 (ddd, 1H, J=1.0 Hz, 7.5 Hz, 8.0 Hz), 7.06 (ddd, 1H, J=1.0 Hz, 7.5 Hz, 8.0 Hz), 4.22 (s, 2H), 3.74 (t, 2H, J=7.5 Hz), 1.73 (tt, 2H, J=7.5 Hz, 7.5 Hz), 1.41-1.25 (m, 18H), 0.88 (t, 3H, J=7.0 Hz).

Step 2: Synthesis of Intermediate o

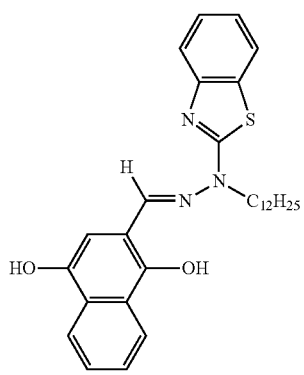

Intermediate o

A four-necked reactor equipped with a thermometer was charged with 564 mg (3.00 mmol) of 1,4-dihydroxynaphthalene-2-carboxaldehyde, 1.00 g (3.00 mmol) of the intermediate n synthesized by the step 1, and 10 ml of 2-propanol under a nitrogen stream. The mixture was refluxed for 1.5 hours. After completion of the reaction, the reaction mixture was cooled to 20° C., and a solid that had precipitated was filtered off. The solid was washed with 2-propanol, and dried using a vacuum dryer to obtain 975 mg of an intermediate o as a yellow solid (yield: 64.5%).

The structure of the target product was identified by $^1$H-NMR.

The $^1$H-NMR spectrum data of the intermediate o are shown below.

$^1$H-NMR (500 MHz, DMSO-$d_6$, TMS, δ ppm): 9.87 (s, 1H), 9.75 (s, 1H), 8.43 (s, 1H), 8.20-8.24 (m, 1H), 8.08-8.11 (m, 1H), 7.87 (dd, 1H, J=1.0 Hz, 8.0 Hz), 7.61 (dd, 1H, J=1.0 Hz, 8.0 Hz), 7.51-7.56 (m, 2H), 7.35 (ddd, 1H, J=1.0 Hz, 7.5 Hz, 8.0 Hz), 7.22 (s, 1H), 7.18 (ddd, 1H, J=1.0 Hz, 7.5 Hz, 8.0 Hz), 4.40 (t, 2H, J=7.5 Hz), 1.73 (tt, 2H, J=7.5 Hz, 7.5 Hz), 1.33-1.43 (m, 4H), 1.16-1.27 (m, 14H), 0.83 (t, 3H, J=7.0 Hz).

Step 3: Synthesis of Compound 34

A four-necked reactor equipped with a thermometer was charged with 975 mg (1.94 mmol) of the intermediate o synthesized by the step 2, 1.42 g (4.85 mmol) of 4-(6-acryloylhex-1-yloxy)benzoic acid (manufactured by DKSH Japan K.K.), 119 mg (0.97 mmol) of 4-(dimethylamino)pyridine, and 15 ml of N-methylpyrrolidone under a nitrogen stream to prepare a homogeneous solution. After the addition of 1.12 g (5.82 mmol) of WSC to the solution, the mixture was stirred at 25° C. for 4 hours. After completion of the reaction, the reaction mixture was added to 100 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=95:5 (volume ratio)) to obtain 1.21 g of a compound 34 as a yellow solid (yield: 59.3%).

The structure of the target product was identified by $^1$H-NMR.

The $^1$H-NMR spectrum data of the compound 34 are shown below.

$^1$H-NMR (500 MHz, CDCl$_3$, TMS, δ ppm): 8.33 (d, 2H, J=9.0 Hz), 8.32 (d, 2H, J=9.0 Hz), 8.05 (s, 1H), 7.88-7.93 (m, 3H), 7.63 (dd, 2H, J=1.0 Hz, 8.5 Hz), 7.51-7.54 (m, 2H), 7.30 (ddd, 1H, J=1.0 Hz, 8.0 Hz, 8.5 Hz), 7.12 (ddd, 1H, J=1.0 Hz, 8.0 Hz, 8.5 Hz), 7.06 (d, 4H, J=9.0 Hz), 6.42 (dd, 2H, J=1.5 Hz, 17.5 Hz), 6.14 (dd, 2H, J=10.5 Hz, 17.5 Hz), 5.84 (dd, 2H, J=1.5 Hz, 10.5 Hz), 4.17-4.22 (m, 6H), 4.11 (t, 2H, J=6.5 Hz), 4.10 (t, 2H, J=7.0 Hz), 1.85-1.89 (m, 4H), 1.73-1.78 (m, 4H), 1.47-1.63 (m, 10H), 1.19-1.33 (m, 18H), 0.88 (t, 3H, J=7.0 Hz).

Measurement of Phase Transition Temperature 10 mg of the compound (compounds 30 to 34) was weighed, and placed in a solid state between two glass substrates provided with a polyimide alignment film subjected to a rubbing treatment. The substrates were heated from 30° C. to 200° C. on a hot plate, and then cooled to 30° C. A change in structure during a change in temperature was observed using a polarizing optical microscope ("ECLIPSE LV100POL" manufactured by Nikon Corporation). The phase transition temperature measurement results are shown in Table 6. In Table 6, "C", "N", and "I" are the same as defined above.

TABLE 6

| | Polymerizable compound | Phase transition temperature |
|---|---|---|
| Example 68 | Compound 30 | C ⇌(94° C. / 30° C. or less) N ⇌(105° C. / 100° C.) I |
| Example 69 | Compound 31 | C ⇌(98° C. / 30° C. or less) N ⇌(72° C.) I |
| Example 70 | Compound 32 | C ⇌(115° C. / 30° C. or less) N ⇌(88° C.) I |
| Example 71 | Compound 33 | C ⇌(67° C. / 30° C. or less) N ⇌(70° C. / 34° C.) I |
| Example 72 | Compound 34 | C ⇌(123° C. / 67° C.) I |

Examples 73 to 76

1.0 g of the corresponding compound among the compounds 30 to 33 obtained in Examples 68 to 71, 30 mg of Adekaoptomer N-1919 (photoinitiator), and 100 mg of a 1% cyclopentanone solution of KH-40 (surfactant) were dissolved in 2.3 g of cyclopentanone. The solution was filtered through a disposable filter having a pore size of 0.45 μm to obtain a polymerizable composition (polymerizable compositions 39 to 42).

Example 77

0.5 g of the compound 34 obtained in Example 72, 0.5 g of the compound 1 obtained in Example 1, 30 mg of Adekaoptomer N-1919 (photoinitiator), and 100 mg of a 1% cyclopentanone solution of KH-40 (surfactant) were dissolved in 2.3 g of cyclopentanone. The solution was filtered through a disposable filter having a pore size of 0.45 μm to obtain a polymerizable composition (polymerizable composition 43).

Measurement 5 of Retardation and Evaluation 5 of Wavelength Dispersion

The retardation was measured, and the wavelength dispersion was evaluated using the polymerizable compositions 39 to 43 in the same manner as in the section "Measurement 1 of retardation and evaluation 1 of wavelength dispersion". The drying temperature, the alignment temperature, the thickness, the retardation (Re), and the values α and β are shown in Table 7.

TABLE 7

|  | Polymerizable composition | Polymerizable compound 1 | | Polymerizable compound 2 | | Drying temperature (° C.) | Alignment temperature (° C.) | Film thickness (μm) | Re (548.5 nm) | α | β |
| --- | --- | --- | --- | --- | --- | --- | --- | --- | --- | --- | --- |
|  |  | Compound | Content (%) | Compound | Content (%) |  |  |  |  |  |  |
| Example 73 | 39 | Compound 30 | 100 | — | — | 110 | 23 | 1.583 | 146.46 | 0.934 | 0.981 |
| Example 74 | 40 | Compound 31 | 100 | — | — | 100 | 23 | 1.573 | 137.60 | 0.900 | 0.993 |
| Example 75 | 41 | Compound 32 | 100 | — | — | 120 | 23 | 1.867 | 171.92 | 0.954 | 0.985 |
| Example 76 | 42 | Compound 33 | 100 | — | — | 110 | 23 | 1.446 | 93.01 | 1.011 | 0.989 |
| Example 77 | 43 | Compound 34 | 50 | Compound 1 | 50 | 110 | 23 | 1.720 | 110.88 | 0.809 | 1.004 |

As is clear from the results shown in Table 7, it was confirmed that optically anisotropic articles (polymers) were obtained in Examples 73 to 77. The values α and β were almost identical when using the optically anisotropic articles obtained in Examples 73 to 77.

The invention claimed is:

1. A polymerizable compound represented by a formula (I),

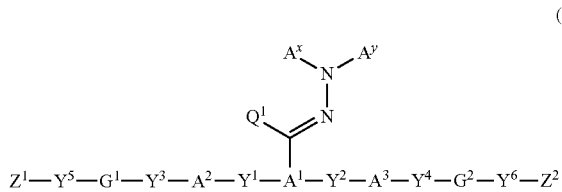

$$Z^1—Y^5—G^1—Y^3—A^2—Y^1—A^1—Y^2—A^3—Y^4—G^2—Y^6—Z^2$$ (I)

wherein $Y^1$ to $Y^6$ are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, $R^1$ is a hydrogen atom or an alkyl group having 1 to 6 carbon atoms, $G^1$ and $G^2$ are independently a substituted or unsubstituted divalent aliphatic group having 1 to 20 carbon atoms that optionally includes —O—, —S—, —O—C(=O)—, —C(=O)—O—, —NR$^2$—C(=O)—, —C(=O)—NR$^2$—, —NR$^2$—, or —C(=O)—, provided that a case where the aliphatic group includes two or more adjacent —O— or —S— is excluded, $R^2$ is a hydrogen atom or an alkyl group having 1 to 6 carbon atoms, $Z^1$ and $Z^2$ are independently an alkenyl group having 2 to 10 carbon atoms that is substituted with a halogen atom, or unsubstituted, $A^x$ is an organic group having 2 to 30 carbon atoms that includes at least one aromatic ring selected from a group consisting of an aromatic hydrocarbon ring and an aromatic hetero ring, $A^y$ is a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, —C(=O)—R$^3$, —SO$_2$—R$^6$, or an organic group having 2 to 30 carbon atoms that includes at least one aromatic ring selected from a group consisting of an aromatic hydrocarbon ring and an aromatic hetero ring, provided that the aromatic ring included in $A^x$ and $A^y$ is substituted or unsubstituted, and $A^x$ and $A^y$ optionally bond to each other to form a ring, $R^3$ is a substituted or unsubstituted alkyl group having 1 to 20 carbon atoms, a substituted or unsubstituted alkenyl group having 2 to 20 carbon atoms, or a substituted or unsubstituted cycloalkyl group having 3 to 12 carbon atoms, $R^6$ is an alkyl group having 1 to 20 carbon atoms, an alkenyl group having 2 to 20 carbon atoms, a phenyl group, or a 4-methylphenyl group, $A^1$ is a substituted or unsubstituted trivalent aromatic group, $A^2$ and $A^3$ are independently a substituted or unsubstituted divalent aromatic group having 6 to 30 carbon atoms, and $Q^1$ is a hydrogen atom, or a substituted or unsubstituted alkyl group having 1 to 6 carbon atoms.

2. The polymerizable compound according to claim 1, wherein a total number of π electrons included in $A^x$ and $A^y$ is 4 to 24.

3. The polymerizable compound according to claim 1, wherein $A^x$ is a substituted or unsubstituted group among groups represented by the following structural formulas,

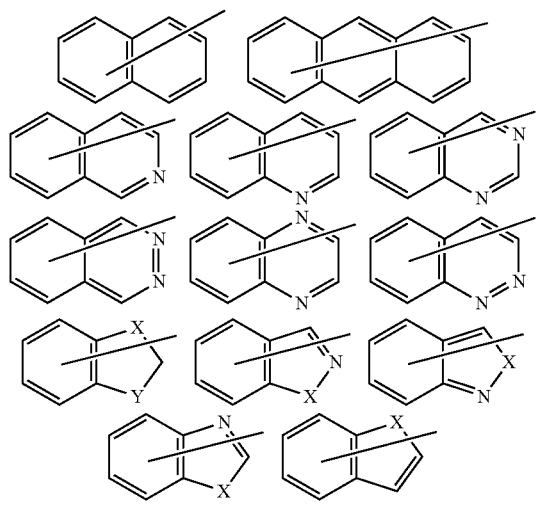

wherein X is NR$^5$, an oxygen atom, a sulfur atom, —SO—, or —SO$_2$—, provided that a case where oxygen atoms, sulfur atoms, —SO—, or —SO$_2$— are situated at adjacent positions is excluded, and $R^5$ is a hydrogen atom or an alkyl group having 1 to 6 carbon atoms.

4. The polymerizable compound according to claim 1, wherein $A^y$ is a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, a group represented by —C(=O)—$R^3$ (wherein $R^3$ is a substituted or unsubstituted alkyl group having 1 to 12 carbon atoms, a substituted or unsubstituted alkenyl group having 2 to 12 carbon atoms, or a substituted or unsubstituted cycloalkyl group having 3 to 12 carbon atoms), or a group represented by —$SO_2$—$R^6$ (wherein $R^6$ is an alkyl group having 1 to 12 carbon atoms, an alkenyl group having 2 to 12 carbon atoms, a phenyl group, or a 4-methylphenyl group).

5. The polymerizable compound according to claim 1, wherein $A^1$ is a substituted or unsubstituted trivalent benzene ring group, or a substituted or unsubstituted trivalent naphthalene ring group, and $A^2$ and $A^3$ are independently a substituted or unsubstituted phenylene group, or a substituted or unsubstituted naphthylene group.

6. The polymerizable compound according to claim 1, wherein $Y^1$ to $Y^6$ are independently a chemical single bond, —O—, —O—C(=O)—, —C(=O)—O—, or —O—C(=O)—O—.

7. The polymerizable compound according to claim 1, wherein $Z^1$ and $Z^2$ are independently $CH_2$=CH—, $CH_2$=C($CH_3$)—, or $CH_2$=C(Cl)—.

8. The polymerizable compound according to claim 1, wherein $G^1$ and $G^2$ are independently a substituted or unsubstituted divalent aliphatic group having 1 to 12 carbon atoms that optionally includes —O—, —O—C(=O)—, —C(=O)—O—, or —C(=O)—, provided that a case where the aliphatic group includes two or more adjacent —O— is excluded.

9. The polymerizable compound according to claim 1, wherein $G^1$ and $G^2$ are independently a divalent alkylene group having 1 to 12 carbon atoms.

10. A polymerizable composition comprising at least one type of the polymerizable compound according to claim 1.

11. A polymerizable composition comprising the polymerizable compound according to claim 1, and an initiator.

12. A polymer obtained by polymerizing the polymerizable compound according to claim 1.

13. The polymer according to claim 12, the polymer being a liquid crystalline polymer.

14. An optically anisotropic article comprising the polymer according to claim 13.

15. The polymerizable compound according to claim 2, wherein $A^x$ is a substituted or unsubstituted group among groups represented by the following structural formulas,

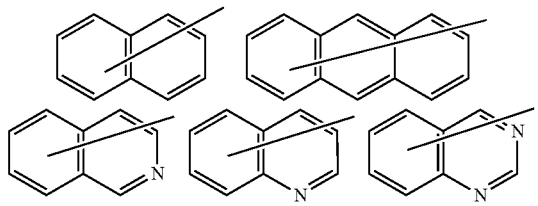

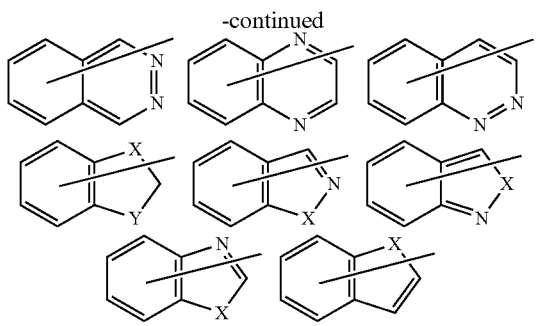

wherein X is $NR^5$, an oxygen atom, a sulfur atom, —SO—, or —$SO_2$—, provided that a case where oxygen atoms, sulfur atoms, —SO—, or —$SO_2$— are situated at adjacent positions is excluded, and $R^5$ is a hydrogen atom or an alkyl group having 1 to 6 carbon atoms.

16. The polymerizable compound according to claim 2, wherein $A^y$ is a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, a group represented by —C(=O)—$R^3$ (wherein $R^3$ is a substituted or unsubstituted alkyl group having 1 to 12 carbon atoms, a substituted or unsubstituted alkenyl group having 2 to 12 carbon atoms, or a substituted or unsubstituted cycloalkyl group having 3 to 12 carbon atoms), or a group represented by —$SO_2$—$R^6$ (wherein $R^6$ is an alkyl group having 1 to 12 carbon atoms, an alkenyl group having 2 to 12 carbon atoms, a phenyl group, or a 4-methylphenyl group).

17. The polymerizable compound according to claim 3, wherein $A^y$ is a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, a group represented by —C(=O)—$R^3$ (wherein $R^3$ is a substituted or unsubstituted alkyl group having 1 to 12 carbon atoms, a substituted or unsubstituted alkenyl group having 2 to 12 carbon atoms, or a substituted or unsubstituted cycloalkyl group having 3 to 12 carbon atoms), or a group represented by —$SO_2$—$R^6$ (wherein $R^6$ is an alkyl group having 1 to 12 carbon atoms, an alkenyl group having 2 to 12 carbon atoms, a phenyl group, or a 4-methylphenyl group).

18. The polymerizable compound according to claim 2, wherein $A^1$ is a substituted or unsubstituted trivalent benzene ring group, or a substituted or unsubstituted trivalent naphthalene ring group, and $A^2$ and $A^3$ are independently a substituted or unsubstituted phenylene group, or a substituted or unsubstituted naphthylene group.

19. The polymerizable compound according to claim 3, wherein $A^1$ is a substituted or unsubstituted trivalent benzene ring group, or a substituted or unsubstituted trivalent naphthalene ring group, and $A^2$ and $A^3$ are independently a substituted or unsubstituted phenylene group, or a substituted or unsubstituted naphthylene group.

20. The polymerizable compound according to claim 4, wherein $A^1$ is a substituted or unsubstituted trivalent benzene ring group, or a substituted or unsubstituted trivalent naphthalene ring group, and $A^2$ and $A^3$ are independently a substituted or unsubstituted phenylene group, or a substituted or unsubstituted naphthylene group.

* * * * *

UNITED STATES PATENT AND TRADEMARK OFFICE
CERTIFICATE OF CORRECTION

PATENT NO.        : 9,207,360 B2
APPLICATION NO.   : 14/114073
DATED             : December 8, 2015
INVENTOR(S)       : Sakamoto et al.

It is certified that error appears in the above-identified patent and that said Letters Patent is hereby corrected as shown below:

ON THE TITLE PAGE:

Item (73), Assignee, change "ZENO CORPORATION, Tokyo (JP)" to --ZEON CORPORATION, Tokyo (JP)--.

Signed and Sealed this
Tenth Day of May, 2016

Michelle K. Lee
*Director of the United States Patent and Trademark Office*